US012734135B2

(12) United States Patent
Fanca-Berthon et al.

(10) Patent No.: US 12,734,135 B2
(45) **Date of Patent: *Sep. 15, 2026**

(54) CURCUMINOID COMPOSITIONS

(71) Applicant: Givaudan France Naturals SAS, Avignon (FR)

(72) Inventors: Pascale Elizabeth Renée Fanca-Berthon, Le Thor (FR); Leila Denise Falcao, Avignon (FR); Mathieu Tenon, Malemort du comtat (FR); Maryline Vinal, Caumont sur Durance (FR); Simona Birtic, Cavaillon (FR)

(73) Assignee: Givaudan France Naturals SAS, Avignon (FR)

( * ) Notice: Subject to any disclaimer, the term of this patent is extended or adjusted under 35 U.S.C. 154(b) by 989 days.

This patent is subject to a terminal disclaimer.

(21) Appl. No.: 17/266,324

(22) PCT Filed: Aug. 5, 2019

(86) PCT No.: PCT/EP2019/071054

§ 371 (c)(1),
(2) Date: Feb. 5, 2021

(87) PCT Pub. No.: WO2020/030611

PCT Pub. Date: Feb. 13, 2020

(65) Prior Publication Data

US 2022/0280449 A1 Sep. 8, 2022

(30) Foreign Application Priority Data

Aug. 6, 2018 (GB) ..................................... 1812772
Feb. 19, 2019 (GB) ..................................... 1902276

(51) Int. Cl.

| | |
|---|---|
| ***A61K 31/12*** | (2006.01) |
| ***A23K 10/30*** | (2016.01) |
| ***A23K 20/111*** | (2016.01) |
| ***A23K 20/158*** | (2016.01) |
| ***A23K 20/163*** | (2016.01) |
| ***A23L 27/10*** | (2016.01) |
| ***A23L 29/25*** | (2016.01) |
| ***A23L 33/105*** | (2016.01) |
| ***A23L 33/115*** | (2016.01) |
| ***A61K 8/35*** | (2006.01) |
| ***A61K 8/9789*** | (2017.01) |
| ***A61K 9/16*** | (2006.01) |
| ***A61K 36/185*** | (2006.01) |

(52) U.S. Cl.

CPC .............. *A61K 31/12* (2013.01); *A23K 10/30* (2016.05); *A23K 20/111* (2016.05); *A23K 20/158* (2016.05); *A23K 20/163* (2016.05); *A23L 27/10* (2016.08); *A23L 29/25* (2016.08); *A23L 33/105* (2016.08); *A23L 33/115* (2016.08); *A61K 8/35* (2013.01); *A61K 8/9789* (2017.08); *A61K 9/1652* (2013.01); *A61K 36/185* (2013.01); *A23V 2002/00* (2013.01)

(58) Field of Classification Search

None

See application file for complete search history.

(56) References Cited

FOREIGN PATENT DOCUMENTS

| | | | |
|---|---|---|---|
| EP | 2671596 | A1 | 12/2013 |
| EP | 2721933 | A1 | 4/2014 |
| WO | 2018083677 | A1 | 5/2018 |

OTHER PUBLICATIONS

M. Kharat, G. Zhang, D. J McCLements; Stability of curcumin in oil-in-water emulsions: Impact of emulsifier type and concentration on chemical degradation, 2018, Food Research International, 111, 178-186 (Year: 2018).*

Bucurescu, A. et al., Microencapsulation of curcumin by a spray-drying technique using gum arabic as encapsulating agent and release studies, Jul. 12, 2018, Food and Bioprocess Tech, vol. 11, 1795-1806 (Year: 2018).*

Cano-Higuita, D.M. et al., Microencapsulation of turmeric oleoresin in binary and ternary blends of gum arabic, maltodextrin, and modified starch, Cienc. Agrotec., 2015, vol. 39, 173-182 (Year: 2015).*

Tippel, J. et al., Colour stability of lutein esters in liquid and spray dried delivery systems based on Quillaja saponins, Food Res. Int., 2016, vol. 87, 68-75 (Year: 2016).*

Sarika, P.R. et al., Curcumin loaded gum arabic aldehyde-gelatin nanogels for breast cancer therapy, Materials Science and Engineering C, 2016, vol. 65, 331-337 (Year: 2016).*

Mahesh Kharat, et al., Stability of curcumin in oil-in-water emulsions: Impact of emulsifier type and concentration on chemical degradation, Food Research International, May 16, 2018, 178-186, vol. 111, Elsevier Ltd.

Naturex SA and Biofortis Merieux NutriSciences, A Comparative Pharmacokinetic Study to Evaluate the Ability of a New Formulation to Enhance Curcuminoids Bioavailability (TURBIO), Identifier: NCT03621865, ClinicalTrials.gov, Aug. 9, 2018.

International Search Report for International Application No. PCT/EP2019/071054 dated Nov. 15, 2019.

(Continued)

*Primary Examiner* — Craig D Ricci

*Assistant Examiner* — Paul Hoerner

(74) *Attorney, Agent, or Firm* — Curatolo Sidoti & Trillis Co., LPA; Salvatore A. Sidoti; Floyd Trillis, III

(57) ABSTRACT

The present invention relates to compositions comprising curcuminoids; in particular, compositions comprising curcuminoids that are highly water soluble. The present invention also relates to processes for providing such compositions and uses of such compositions.

16 Claims, 35 Drawing Sheets

(56) References Cited

OTHER PUBLICATIONS

Written Opinion for International Application No. PCT/EP2019/071054 dated Nov. 15, 2019.
Great Britain Search Report for Application No. 1812776.1 dated Jan. 31, 2019.
International Search Report for International Application No. PCT/EP2019/071055 dated Nov. 26, 2019.
Written Opinion of the International Searching Authority for International Application No. PCT/EP2019/071055 dated Nov. 26, 2019.

* cited by examiner

| | R | R' |
|---|---|---|
| Curcumin | $OCH_3$ | $OCH_3$ |
| Demethoxy-curcumin | H | $OCH_3$ |
| Bis-demethoxy-curcumin | H | H |

Figure 1

Figure 2:
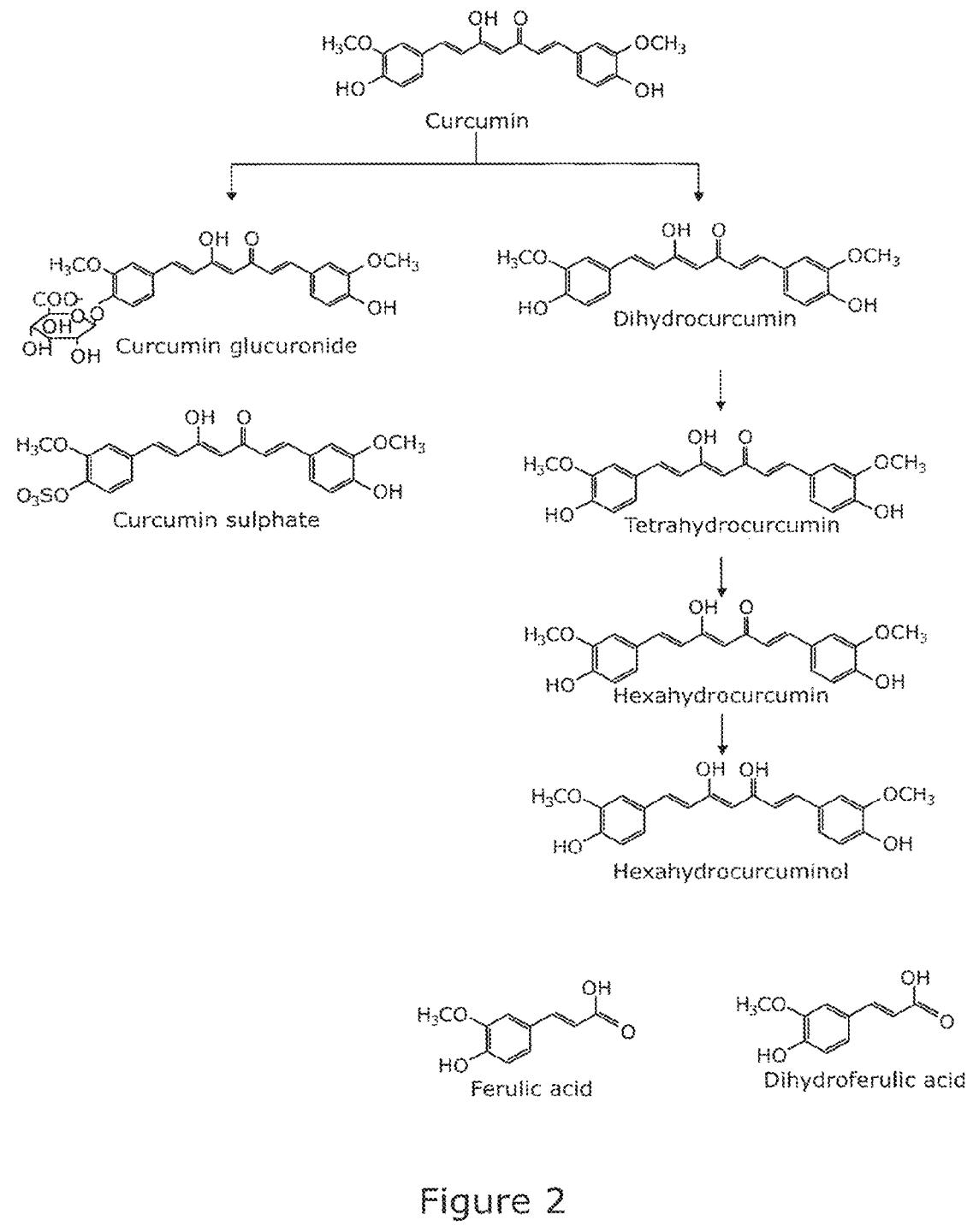

Curcumin

Curcumin glucuronide

Curcumin sulphate

Dihydrocurcumin

Tetrahydrocurcumin

Hexahydrocurcumin

Hexahydrocurcuminol

Ferulic acid

Dihydroferulic acid

Figure 3:
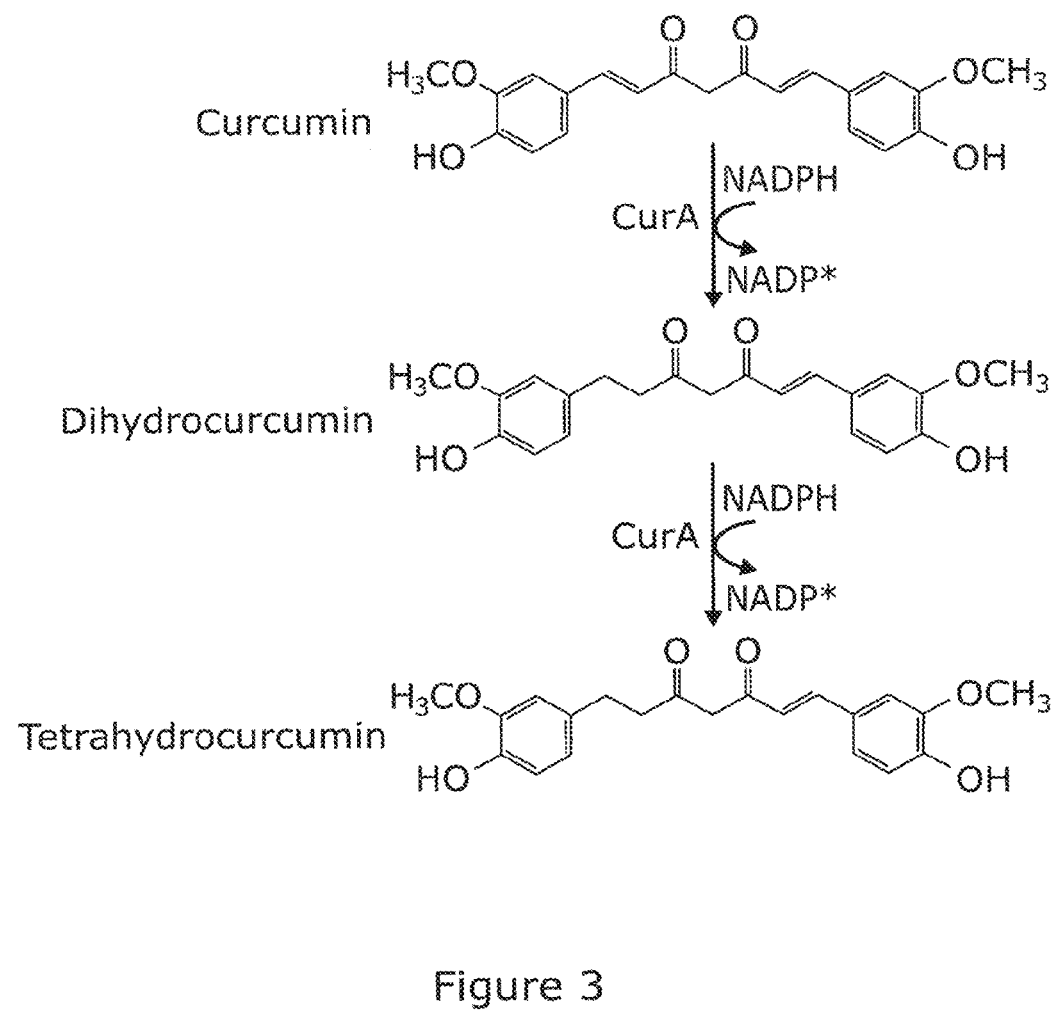

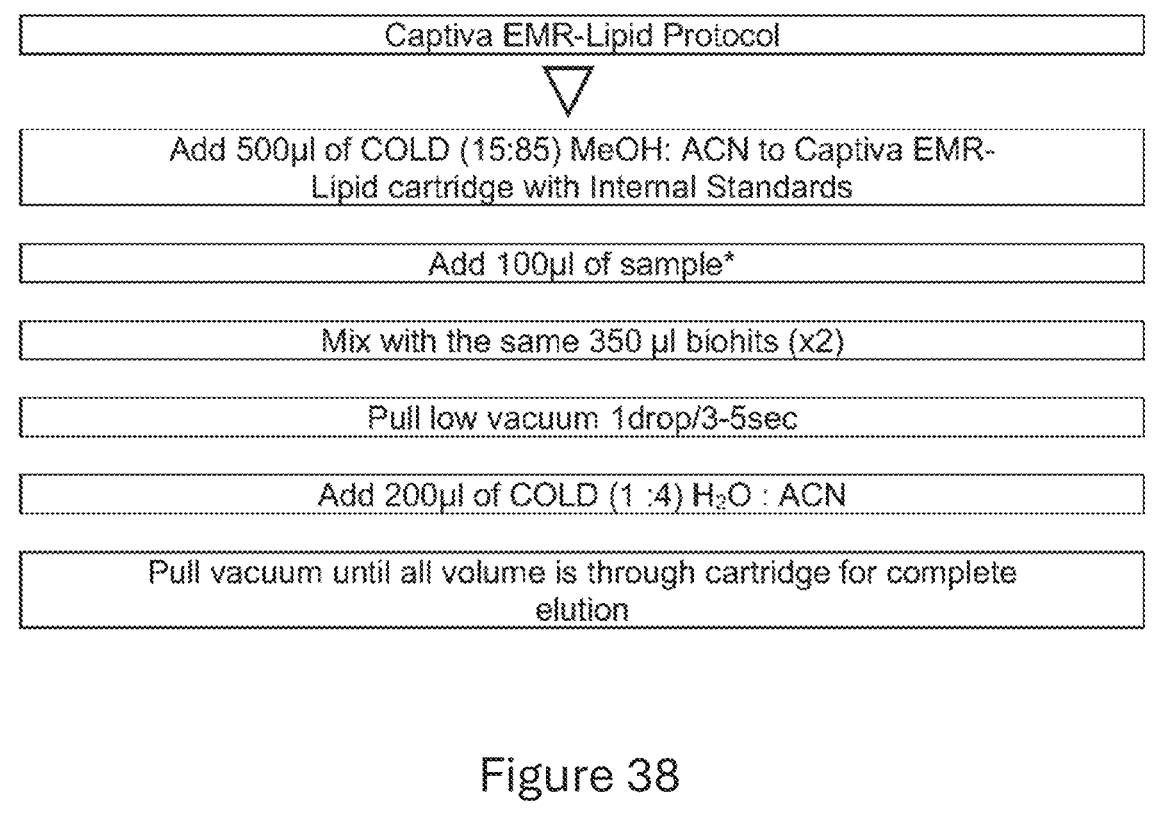

Captiva EMR-Lipid Protocol

Add 500µl of COLD (15:85) MeOH: ACN to Captiva EMR-Lipid cartridge with Internal Standards Add 100µl of sample*

Mix with the same 350 µl biohits (x2)

Pull low vacuum 1drop/3-5sec

Add 200µl of COLD (1 :4) $H_2O$ : ACN

Pull vacuum until all volume is through cartridge for complete elution

Figure 38

CURCUMINOID COMPOSITIONS

FIELD OF THE INVENTION

The present invention relates to compositions comprising curcuminoids; in particular, compositions comprising curcuminoids that are highly water soluble. The present invention also relates to processes for providing such compositions and uses of such compositions.

BACKGROUND OF THE INVENTION

The listing or discussion of an apparently prior-published document in this specification should not necessarily be taken as an acknowledgement that the document is part of the state of the art or is common general knowledge.

Turmeric and compounds isolated from turmeric, such as curcuminoids including curcumin, have been used for a long time to treat a variety of diseases and conditions. Curcuminoids are natural yellow-orange pigments and hydrophobic polyphenols derived from the rhizome of the herb *Curcuma longa*. They are commonly isolated from the spice and food-coloring agent turmeric.

Turmeric extract contains approximately 75-80% curcumin, 15-20% demethoxycurcumin (DMC), and 0-10% bisdemethoxycurcumin (BDMC) (see FIG. 1). Curcuminoids have a unique conjugated structure, a bis-α,β-unsaturated β-diketone (commonly called diferuloylmethane), which exhibits keto-enol tautomerism having a predominant keto form in acidic and neutral solutions and stable enol form in alkaline medium (Hoehle S I, Pfeiffer E, Sólyom A M, Metzler M. Metabolism of curcuminoids in tissue slices and subcellular fractions from rat liver. J Agric Food Chem. 2006 Feb. 8; 54(3):756-64).

While the exact mechanism by which curcumin is able to impart valuable health benefits remains unclear, the overall positive effect is quite pronounced in some cases.

Curcumin is a highly pleiotropic molecule that was first shown to exhibit antibacterial activity in 1949. Since then, this polyphenol has been shown to possess anti-inflammatory, hypoglycemic, antioxidant, wound-healing, and antimicrobial activities. Extensive preclinical studies and clinical trials over the past three decades have indicated curcumin's therapeutic potential against a wide range of human diseases (Gupta S C, Sung B, Kim J H, Prasad S, Li S, Aggarwal B B. Multitargeting by turmeric, the golden spice: From kitchen to clinic. Mol Nutr Food Res. 2013 September; 57(9):1510-28).

Although curcumin has shown efficacy against numerous human disorders, it is also known to have limited bioavailability due to poor absorption, rapid metabolism, and rapid systemic elimination.

Low serum levels, as well as limited tissue distribution and rapid metabolism, have been reported when curcumin is orally administrated. For example, it has been demonstrated that even after oral doses of up to 12 g, blood serum levels of curcumin did not exceed the low micromolar level. In one clinical study with 4-8 g of curcumin, the maximum serum concentration observed was 1.3 μg/mL, while several other clinical and animal studies reported serum levels in the lower nanogram per milliliter range (Anand P, Kunnumakkara A B, Newman R A, Aggarwal B B. Bioavailability of curcumin: problems and promises. Mol Pharm. 2007 November-December; 4(6):807-18).

Curcumin has been found to be poorly soluble in water. For example, the maximum solubility of curcumin in aqueous buffer (pH 5.0) was reported to be as low as 11 ng/ml (Tønnesen H H, Messon M, Loftsson T. Studies of curcumin and curcuminoids. XXVII. Cyclodextrin complexation: solubility, chemical and photochemical stability. Int J Pharm. 2002 Sep. 5; 244(1-2):127-35).

Curcumin is relatively stable at acidic pH but rapidly decomposes at pH above neutral and forms ferulic acid and feruloylmethane, the last one giving then vanillin (FAO 2004. CURCUMIN Chemical and Technical Assessment (CTA) First draft prepared by Ivan Stankovic. Chemical and Technical Assessment 61st JECFA).

Curcumin also exhibits very low intestinal absorption. The apparent permeability coefficients of curcumin were found extremely low in an in vitro human intestinal cell model (Papp value: 0.1×10-6 cm/s), which could predict, according to the correlation of Papp values determined in Caco-2 cells in vitro with human absorption in vivo, a low (0-20%) absorption in humans (Dempe J S, Scheerle R K, Pfeiffer E, Metzler M. Metabolism and permeability of curcumin in cultured Caco-2 cells. Mol Nutr Food Res. 2013 September; 57(9):1543-9).

Once absorbed, curcumin undergoes both phase I and phase II metabolism (see FIG. 2).

In phase I metabolism, curcumin and its two demethoxy congeners undergo successive reduction to their dihydro-, tetrahydro-, hexahydro-, and octahydro-metabolites in the liver as well as in the intestinal mucosa. In phase II metabolism, both curcumin and its reductives metabolites are conjugated with glucuronic acid and sulfate and form phase II metabolites.

Reduction and conjugation appear to be general metabolic pathways of curcuminoids, taking place in hepatic and intestinal tissues of rats and humans. Thus, biological effects elicited by curcumin in tissues other than gastrointestinal tract are believed to be more likely due to curcumin metabolites by several authors.

Curcumin has also been shown to be metabolized by intestinal microorganisms (see FIG. 3).

The microbial metabolism of curcumin was found to comprise a two-step reduction, with curcumin being converted successively into dihydrocurcumin and then tetrahydrocurcumin by an NADPH-dependent curcumin/dihydrocurcumin reductase (CurA) (Hassaninasab et al., 2011).

A recent study also reported that tetrahydroxycurcumin, but not curcumin, could accumulate in tissue in rats, suggesting that microbiota could be also considered as a potential actor in curcumin metabolism and bioavailability (Neyrinck A M, Alligier M, Memvanga P B, Névraumont E, Larondelle Y, Préat V, Cani P D, Delzenne N M. *Curcuma longa* extract associated with white pepper lessens high fat diet-induced inflammation in subcutaneous adipose tissue. PLoS One. 2013 Nov. 19; 8(11):e81252).

The rapid metabolism, poor water solubility, instability at neutral pH and upon exposure to light and/or oxygen, and poor uptake by tissues drastically limits the potential utility of curcuminoids, including the potential use of curcuminoids, such as curcumin in the treatment of conditions such as cancer.

Several phase I and phase II clinical trials have demonstrated promising effects of oral curcumin administration in patients with colorectal neoplasia, advanced pancreatic and breast cancer—either with or without additional chemotherapy. More specifically, curcumin displays anti-melanoma efficiency both in vitro and in vivo.

Despite the great therapeutic potential of curcumin in a variety of cancers (including melanoma), its clinical application has been strongly hindered due to a number of limiting characteristics including: rapid metabolism, poor water solubility, instability at neutral pH and upon exposure to light and/or oxygen, and poor uptake by tissues. The above characteristics drastically limit the potential utility of curcumin in the treatment of conditions such as cancer.

Due to poor water solubility and absorption characteristics, organic solvents are typically used to dissolve curcuminoids, such as curcumin. For example, solvents such as dimethylsulfoxide (DMSO). However, although the use of such solvents helps to solubilize curcumin and to improve availability, the use of organic solvents as a vehicle is controversial and undesirable, especially in an age where there is increasing consumer demand for natural ingredients.

Another possibility to aid the water solubility of curcumin is via emulsification. However, natural organic grade emulsifiers are rare and both synthetic emulsifiers, such as polysorbate 80, and natural emulsifiers, such as starch-based emulsifiers, are typically only capable of dispersing low levels (<7%) of curcumin in water.

Other strategies that have been explored in order to address the above shortcomings and to improve the therapeutic efficacy of curcumin include the use of polymeric nanoparticles, polymer micelles and methods including grafting curcumin to a hydrophilic polymer.

The present invention seeks to address the abovementioned problems associated with curcuminoid's poor solubility in water and provide a composition comprising curcuminoids that is both highly soluble in water and stable at physiological pH.

DISCLOSURE OF THE INVENTION

Composition

The present inventors have surprisingly found that a composition comprising at least about 20% curcuminoids by weight of the composition, gum arabic and an extract obtained from or obtainable from quillaja, wherein the composition comprises particles having an average diameter of from about 100 nm to about 10000 nm is highly water soluble and stable at physiological pH.

According to the present invention, there is provided a composition comprising:

(i) at least about 20% curcuminoids by weight of the composition;

(ii) gum arabic; and (iii) an extract obtained or obtainable from quillaja, wherein the composition comprises particles having an average diameter of from about 100 nm to about 10000 nm such as from about 100 nm to about 700 nm or from about 1000 nm to about 6000 nm.

According to the present invention, there is also provided a composition comprising:

(iv) at least about 20% curcuminoids by weight of the composition;

(v) gum arabic; and (vi) an extract obtained or obtainable from quillaja, wherein the composition comprises particles having an average diameter of from about 100 nm to about 700 nm.

Such compositions may be referred to hereinafter as the "composition of the invention".

The composition of the invention may be in the form of an emulsion or the composition of the invention may be in the form a solid, for example, in the form of a powder.

As used herein, the term "emulsion" refers to a type of colloid that is formed by combining two liquids that do not usually mix. Typically, one of the liquids will contain a dispersion of the other liquid.

Sometimes the terms "colloid" and "emulsion" are used interchangeably, but as used herein the term emulsion applies when both phases of a mixture are liquids. The particles in a colloid can be any phase of matter. So, an emulsion is a type of colloid, but not all colloids are emulsions.

A colloidal solution, occasionally identified as a colloidal suspension, is a mixture in which the substances are regularly suspended in a fluid.

Some compositions of the invention do not comprise fenugreek, for example, some compositions of the invention do not comprise fenugreek fibre (i.e. fibre obtained or obtainable from fenugreek).

The composition of the invention may comprise small amounts of polyols and/or low molecular weight sugars with preferably 1 or 2 monosaccharide units, such as less than 5% by weight of the composition or less than 2.5% by weight of the composition. Alternatively, the composition of the invention may be free of polyols and/or low molecular weight sugars such as those with 1 or 2 monosaccharide units, i.e. some compositions do not contain any polyols and/or low molecular weight sugars, such as those with 1 or 2 monosaccharide units.

In the composition of the invention, the particles may have an average diameter of from about 200 nm, 300 nm, 400 nm, 500 nm, 600 nm, 700 nm, 800 nm, 900 nm, 1000 nm, 1100 nm, 1200 nm, 1300 nm, 1400 nm or 1500 nm to about 9000 nm, 8000 nm, 7000 nm, 6000 nm, 5000 nm, 4000 nm, 3000 nm or 2000 nm, such as from about 1000 nm to about 6000 nm. The particles may also have an average diameter of from about 200 nm to about 600 nm, or from about 300 nm to about 500 nm or about 400 nm.

For example, where the composition is in the form of an emulsion, the composition may, for example, comprise particles having an average diameter of from about 550 nm to about 700 nm and particles having an average diameter of from about 100 nm to about 250 nm giving an average diameter of about 400 nm.

Where the composition is in the form of a solid, such as a powder, the composition may, for example, comprise particles having an average diameter of from about 1000 nm to about 6000 nm, such as from about 2000 nm to about 4000 nm.

The particles in the composition of the invention may be in the form of micelles.

In the composition of the invention, for example where the composition is in the form of a solid, the particles may be formed using such techniques known in the art, such as spray drying.

After the formation of the particles (for example, after drying, such as spray drying) the particles may be ground and/or milled (such as ball milled) to provide a more uniform size.

The size and morphology of loaded curcumin micelle were analyzed by dynamic light scattering (DLS), and zeta potential (Z-potential), and scanning electron microscopy (SEM). For DLS and zeta-potential analyses a Zetasizer Nano ZS (NanoZS90, Malvern Instrument Ltd., UK) with a He/Ne laser (A=633 nm) at a fixed scattering angle of 90$^{0}$ at temperature of (25±0.1° C.). For example, the size of the particles may be measured by method CQ-MO-304 as defined in the Examples below.

In the composition of the invention, the curcuminoids may be obtained from any source. However, it is preferred that the curcuminoids are obtained from a natural source, i.e. the curcuminoids are not synthetic, but are plant based.

The composition of the invention may comprise at least about 25% curcuminoids or at least about 30% curcuminoids by weight of the composition.

For example, in the composition of the invention the curcuminoids may be present in an amount from about 20% to about 60%, such as from about 25% to about 50%, or from about 28% to about 48% by weight of the composition.

The curcuminoids may be provided by extraction and optionally purification from the root (rhizome) of turmeric (*Curcuma longa*), oleoresin turmeric root, defatted oleoresin turmeric root and mixtures thereof, i.e. (i) the curcuminoids may be in the form of an extract or purified extract of turmeric comprising from about 30% to about 100% curcuminoids, such as from about 35%, 40%, 45%, 50%, 55%, 60%, 65%, 70%, 75%, 80%, 85% or 90% to about 95%, 90%, 85%, 80%, 75%, 70%, 65%, 60%, 55%, 50% or 45% curcuminoids based on the percentage of total curcuminoids in the extract.

Where the curcuminoids are provided as an extract of turmeric, the turmeric may be extracted using an alcohol-based extraction solvent, such as a water/alcohol mixture or an alcohol. For example, the alcohol-based extraction solvent may be water/methanol (i.e. a mixture of water and methanol) or water/ethanol (i.e. a mixture of water and ethanol) or methanol or ethanol.

Where the extraction solvent comprises a water/alcohol mixture the ratio of water to alcohol may be from about 25:75 to about 1:99, such as from about 20:80 to about 5:95 or about 10:90. For example, the extraction solvent may be water/ethanol in a ratio of from about 25:75 to about 1:99, such as from about 20:80 to about 5:95 or about 10:90.

The turmeric extract may then be further purified to provide an extract of curcuminoids comprising from about 30% to about 100% curcuminoids, such as from about 35%, 40%, 45%, 50%, 55%, 60%, 65%, 70%, 75%, 80%, 85% or 90% to about 95%, 90%, 85%, 80%, 75%, 70%, 65%, 60%, 55%, 50% or 45% curcuminoids based on the percentage of total curcuminoids in the extract.

The purification of the extract may be performed using such techniques known in the art. Typically, the extract is purified using an alcohol-based solvent, such as 100% methanol or 100% ethanol.

The turmeric extract may optionally be dried to remove any excess solvent.

Where the curcuminoids are provided in the form of a turmeric extract as previously defined, the composition may comprise from about from about 30% to about 50% turmeric extract, such as from about 35% to about 45% by weight of the composition. For example, the composition may comprise from about 35% (i.e. 35%) to about 45% turmeric extract by weight of the composition, where the turmeric extract comprises from about 85% to about 95% curcuminoids by weight of the turmeric extract, providing a composition that comprises from about 30% (i.e. 30%) to about 43% curcuminoids by weight of the composition.

The curcuminoids may be provided as a liquid or a powder, such as a powder. For example, a powdered turmeric extract.

As used herein, the term "curcuminoids" includes curcumin, demethoxycurcumin (DMC), and bisdemethoxycurcumin (BDMC). For example, the turmeric extract may comprise from about 70% to about 85% curcumin (such as from about 75% to about 80%), from about 10% to about 25% DMC (such as from about 15% to about 20%) and from about 0% to about 10% BDMC.

The gum arabic in the composition of the invention may be present in an amount from about 40% to about 65% by weight of the composition, such as from about 50 to about 60% by weight of the composition or about 58% by weight of the composition.

The extract obtained or obtainable from quillaja in the composition of the invention may be present in an amount from about 0.1% to about 5% by weight of the composition, such as from about 0.5% to about 3% or about 2% by weight of the composition.

As will be appreciated by the person skilled in the art, as used herein the term "obtainable from" means that the quillaja extract may be obtained from a plant of the *Quillaja* genus (such as *Quillaja saponaria molina*) or may be isolated from the plant of the *Quillaja* genus, or may be obtained from an alternative source, for example by chemical synthesis or enzymatic production. Whereas the term "obtained" as used herein, means that the extract is directly derived from the plant of the *Quillaja* genus.

The extract obtained or obtainable from quillaja in the composition of the invention may comprise at least 50% saponins, such as at least 60% saponins or at least 65% saponins by weight of the quillaja extract. For example, the quillaja used in the composition of the invention may comprise from about 50% to about 80% or from about 60% to about 75% saponins by weight of the quillaja extract.

The extract obtained from or obtainable from quillaja used in the process of the invention may be in any form, such as a liquid or a solid. For example, the quillaja extract may be used in the form of a solid, such as a powder.

When present in the composition of the invention, the quillaja water and/or other solvent, such as alcohol, may be added to the solid or liquid quillaja. For example, the quillaja may be present in the composition of the invention as an aqueous solution.

The composition of the invention may optionally comprise a plant and/or vegetable oil. For example, the composition of the invention may comprise plant and/or vegetable oils selected from the group consisting of coconut oil, corn oil, cottonseed oil, olive oil, palm oil, peanut oil (ground nut oil), rapeseed oil, including canola oil, safflower oil, sesame oil, soybean oil, sunflower oil, and mixtures thereof.

The plant and/or vegetable oil present in the composition of the invention may be present in an amount of from about 1% to about 20% plant and/or vegetable oil, such as from about 2.5% to about 10% or about 5% by weight of the composition.

Unless otherwise stated herein, the weight percentages listed are based on the total weight of (dry) composition obtained.

For the avoidance of doubt, preferences, options, particular features and the like indicated for a given aspect, feature or parameter of the invention should, unless the context indicates otherwise, be regarded as having been disclosed in combination with any and all other preferences, options particular features and the like as indicated for the same or other aspects, features and parameters of the invention.

The term "about" as used herein, e.g. when referring to a measurable value (such as an amount or weight of a particular component in the reaction mixture), refers to variations of ±20%, ±10%, ±5%, ±1%, ±0.5%, or, particularly, ±0.1% relative to the specified amount. For example, a variation of ±0.5% with regards to the percentage of a component in the composition of the invention, means a variation of 0.5% relative to the percentage given, i.e. ±0.5% of 10% would mean a variation from 9.5% to 10.5%.

The composition of the invention may be provided in a solid or liquid form, preferably a solid form, such as a powder. By solid form, it is included that the compound may be provided as an amorphous solid, or as a crystalline or part-crystalline solid.

The composition of the invention is typically highly water soluble and/or stable at a pH of 4 or more, such as a pH from about 4 to about 7.

By the term water soluble we mean that at least about 50%, such as at least about 60%, 70%, 80%, 90% or 95% of the composition will dissolve in water at room temperature, i.e. a temperature of about 25° C.

Compositions and Administration

According to the present invention, the composition of the invention may be provided in the form of a nutraceutical formulation, a dietary or food product for humans or animals (such as functional food formulations, i.e. food, drink, feed or pet food or a food, drink, feed or pet food supplements), a herbicide, a nutritional supplement, a fragrance or flavouring, a pharmaceutical or veterinary formulation, an oenological or cosmetic formulation or may form a part of a nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation.

For example, the present invention provides a nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation consisting of, consisting essentially of (i.e. at least 90% w/w of the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation is the composition of the invention, such as at least 95%, or 99% or 99.5%) or comprising the composition of the invention.

The present invention also provides the use of a composition of the invention in a nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation.

Where the composition of the invention is in the form of a nutraceutical formulation, a dietary or food product for humans or animals (such as functional food formulations, i.e. food, drink, feed or pet food or a food, drink, feed or pet food supplements), a herbicide, a nutritional supplement, a fragrance or flavouring, a pharmaceutical or veterinary formulation, an oenological or cosmetic formulation or may form a part of a nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation, may optionally further comprise a pharmaceutically/veterinary ingredients, such as excipients or carriers or (function) food acceptable ingredients and mixtures thereof as appropriate.

For the avoidance of doubt, in this specification when we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only.

It is also intended that the terms "comprise" or "comprises" or "comprising" may be replaced with "consist" or "consisting" or "consisting essentially of" throughout the application as required.

As used herein, references to pharmaceutically acceptable excipients may refer to pharmaceutically acceptable adjuvants, diluents and/or carriers as known to those skilled in the art.

Food acceptable ingredients include those known in the art (including those also referred to herein as pharmaceutically acceptable excipients) and that can be natural or non-natural, i.e. their structure may occur in nature or not. In certain instances, they can originate from natural compounds and be later modified (e.g. maltodextrin).

By "pharmaceutically/nutraceutically acceptable" we mean that the additional components of the composition are sterile and pyrogen free. Such components must also be "acceptable" in the sense of being compatible with the composition of the invention and not deleterious to the recipients thereof. Thus, "pharmaceutically acceptable" includes any compound(s) used in forming a part of the formulation that is intended to act merely as an excipient, i.e. not intended to have biological activity itself. Thus, the pharmaceutically acceptable excipient is generally safe, non-toxic, and neither biologically nor otherwise undesirable.

Where the composition of the invention forms part of a nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation, the composition of the invention is present in the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation in an amount from about 1 to about 99% by weight of the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation, such as from about 10%, 20%, 30%, 40%, 50%, 60%, 70%, 80% or 90% to about 90%, 80%, 70%, 60%, 50%, 40%, 30%, or 20% by weight of the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation.

Administration

The skilled person will understand that the composition of the invention, either where the composition is in the form of nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation or where the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation comprises the composition of the invention, the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation may be administered to a patient or subject (e.g. a human or animal patient or subject) by any suitable route, such as by the oral, rectal, nasal, pulmonary, buccal, sublingual, transdermal, intracisternal, intraperitoneal, and parenteral (including subcutaneous, intramuscular, intrathecal, intravenous and intradermal) route.

In particular, compositions of the invention and nutraceutical formulations, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation comprising the composition of the invention may be administered orally. In such instances, pharmaceutical compositions according to the present invention may be specifically formulated for administration by the oral route.

Pharmaceutical formulations for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art.

Liquid dosage forms for oral administration include solutions, emulsions, aqueous or oily/oil based suspensions, syrups and elixirs.

Nutraceutical formulations, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation described herein, such as those intended for oral administration, may be prepared according to methods known to those skilled in the art, such as by bringing the components of the composition into admixture.

Such nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulations as described herein may contain one or more additional components selected from the group consisting of food ingredients, such as sweetening agents, flavouring agents, colouring agents and preserving agents. Tablets may contain the active ingredient(s) in admixture with non-toxic pharmaceutically acceptable excipients (or ingredients) which are suitable for the manufacture of tablets. These excipients (or ingredients) may, for example, be: inert diluents, such as calcium carbonate, sodium carbonate, lactose, calcium phosphate or sodium phosphate; granulating and disintegrating agents, for example, corn starch, maltodextrin or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Suitable pharmaceutical carriers include inert solid diluents or fillers, sterile aqueous solutions and various organic solvents. Examples of solid carriers are lactose, terra alba, sucrose, cyclodextrin, maltodextrin, talc, gelatine, agar, pectin, acacia, magnesium stearate, stearic acid, arabic gum, modified starch and lower alkyl ethers of cellulose. Examples of liquid carriers are syrup, peanut oil, olive oil, phospholipids, fatty acids, fatty acid amines, polyoxyethylene and water. Moreover, the carrier or diluent may include any sustained release material known in the art, such as glyceryl monostearate or glyceryl distearate, alone or mixed with a wax.

Depending on the disorder, and the patient, to be treated, as well as the route of administration, compositions of the invention may be administered at varying doses (i.e. therapeutically effective doses, as administered to a patient in need thereof). In this regard, the skilled person will appreciate that the dose administered to a mammal, particularly a human, in the context of the present invention should be sufficient to effect a therapeutic response in the mammal over a reasonable timeframe. One skilled in the art will recognize that the selection of the exact dose and formulation and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Typically, the composition of the invention or the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation is administered to provide curcuminoids in an amount of from about 100 mg/day to about 2000 mg/day, or from about 500 mg/day to about 1500 mg/day, or about 1000 mg/day, such as from about 300 mg/day to about 1000 mg/day. For example, the composition or the nutraceutical formulation, a dietary or food product for humans or animals (such as functional food formulations, i.e. food, drink, feed or pet food or a food, drink, feed or pet food supplements), a nutritional supplement, a fragrance or flavouring, a pharmaceutical or veterinary formulation, an oenological or cosmetic formulation may provide curcuminoids in an amount of from about 1 to about 10 mg/kg of body weight, such as from about 2.5 to about 7.5 mg/kg of body weight or about 5 mg/kg.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Process for the Preparation of Compositions of the Invention

The present invention provides a process for the preparation of a composition of the invention as previously defined, wherein the process comprises the steps of:

(i) preparing an aqueous solution of curcuminoids;

(ii) mixing the aqueous solution from (i) with an aqueous gum arabic solution, and extract obtained or obtainable from quillaja, and optionally the plant and/or vegetable oil, to provide an emulsion; and optionally (iii) drying the product of (ii) to provide a composition comprising particles having an average diameter of from about 100 nm to about 10000 nm, such as from about 100 nm to about 700 nm or from about 1000 nm to about 6000 nm.

For example, the present invention provides a process for the preparation of a composition of the invention as previously defined, wherein the process comprises the steps of:

(i) preparing an aqueous solution of curcuminoids;

(ii) mixing the aqueous solution from (i) with an aqueous gum arabic solution, and extract obtained or obtainable from quillaja, and optionally the plant and/or vegetable oil, to provide an emulsion; and (iii) drying the product of (ii) to provide a composition comprising particles having an average diameter of from about 100 nm to about 10000 nm such as from about 100 nm to about 700 nm or from about 1000 nm to about 6000 nm.

Such processes are hereinafter referred to as the process of the invention.

In the process of the invention, the aqueous solution of gum arabic may be mixed with the aqueous solution of curcuminoids before mixing with the extract obtained or obtainable from quillaja and optionally the plant and/or vegetable oil, i.e. the process of the invention may comprise:

(i) preparing an aqueous solution of curcuminoids;

(ii) mixing the aqueous solution from (i) with an aqueous gum arabic solution;

(iii) mixing the extract obtained or obtainable from quillaja and optionally the plant and/or vegetable oil to the product of (ii) to provide an emulsion; and optionally (iv) drying the product of (iii) (such as by spray drying) to provide a composition comprising particles having an average diameter of from about 100 nm to about 10000 nm, such as from about 100 nm to about 700 nm or from about 1000 nm to about 6000 nm.

After drying, (such as spray drying) the particles may be ground and/or milled (such as ball milled) to provide a more uniform size.

In the process of the invention, the particles may have an average diameter from about 200 nm, 300 nm, 400 nm, 500 nm, 600 nm, 700 nm, 800 nm, 900 nm, 1000 nm, 1100 nm, 1200 nm, 1300 nm, 1400 nm or 1500 nm to about 9000 nm, 8000 nm, 7000 nm, 6000 nm, 5000 nm, 4000 nm, 3000 nm or 2000 nm, such as from about 1000 nm to about 6000 nm. The particles may also have an average diameter of from about 200 nm to about 600 nm, or from about 300 nm to about 500 nm or about 400 nm.

For example, where the composition of the invention is in the form of an emulsion (i.e. before the drying step), the composition may comprise particles having an average diameter of from about 550 nm to about 700 nm and particles having an average diameter of from about 100 nm to about 250 nm giving an average diameter of about 400 nm.

Where the composition is in the form of a solid, such as a powder (i.e. after the drying step), the composition may comprise particles having an average diameter of from about 1000 nm to about 6000 nm, such as from about 2000 nm to about 4000 nm.

The particles in the composition may be in the form of micelles.

In the process of the invention, the curcuminoids present in the aqueous solution of curcuminoids may be from any source as previously defined with respect to the composition of the invention.

Typically, in the process of the invention, the curcuminoids may have a purity (based on total curcuminoids) of from about 5% to about 100% by weight of the curcuminoids source, i.e. the turmeric or curcuminoid extract may comprise from about 30% to about 100% curcuminoids, such as from about 35%, 40%, 45%, 50%, 55%, 60%, 65%, 70%, 75%, 3080%, 85% or 90% to about 95%, 90%, 85%, 80%, 75%, 70%, 65%, 60%, 55%, 50% or 45% curcuminoids based on the percentage of total curcuminoids in the extract.

In the process of the invention, the curcuminoids may be mixed with water in a weight ratio of from about 2:1 (curcuminoids:water) to about 4:1, such as about 3:1, to provide the aqueous solution of curcuminoids.

Typically, in the process of the invention, the weight concentration of curcuminoids in the aqueous solution may be from about 1% to about 95%, such as from about 5% to about 80% or from about 7% to about 40%.

In the process of the invention, the aqueous gum arabic solution may be prepared by mixing gum arabic with water in a ratio of gum arabic:water of from about 2:1 to about 4:1, such as about 3:1.

The aqueous gum arabic solution may have a weight concentration of gum arabic of from about 30% to about 70%, such as from about 40% to about 60%.

Typically, the aqueous curcuminoids solution and aqueous gum arabic solution are mixed using agitation.

In the process of the invention, the plant and/or vegetable oil, may be from any plant and/or vegetable source. For example, the plant and/or vegetable oil may be sunflower oil.

Typically, in the process of the invention, the plant and/or vegetable oil may be present in an amount of from about 1% to about 10% plant and/or vegetable oil, such as from about 2.5% to about 7.5% or about 5%.

In the process of the invention, the extract obtained from or obtainable from quillaja may be as defined previously with respect to the composition of the invention.

The extract obtained from or obtainable from quillaja used in the process of the invention may be in any form, such as a liquid or a solid. For example, the quillaja extract may be used in the form of a solid, such as a powder.

Typically, in the process of the invention, the quillaja may be present in an amount of from 30 about 0.5% to about 5% quillaja, such as from about 1% to about 3%, or about 2%.

In the process of the invention, the plant and/or vegetable oil and quillaja extract may be mixed using agitation.

Mixing the aqueous solution of curcuminoids, aqueous gum arabic solution, plant and/or vegetable oil and quillaja as defined above provide an emulsion.

The resulting emulsion may be dried using such techniques as known in the art to provide a composition comprises particles (such as micelles) having an average diameter of from about 200 nm, 300 nm, 400 nm, 500 nm, 600 nm, 700 nm, 800 nm, 900 nm, 1000 nm, 1100 nm, 1200 nm, 1300 nm, 1400 nm or 1500 nm to about 9000 nm, 8000 nm, 7000 nm, 6000 nm, 5000 nm, 4000 nm, 3000 nm or 2000 nm, such as from about 1000 nm to about 6000 nm. The particles may also have an average diameter of from about 100 nm to about 700 nm, or from about 200 nm to about 600 nm, such as from about 300 nm to about 500 nm, or about 400 nm. Typically, the emulsion is spray dried.

The process of the invention may optionally include a step of removing additional solvent as required in order to provide a substantially dry product, i.e. a product where at least 90%, such as at least 95% or 99% of the water present has been removed.

Methods and Uses

The high water solubility and stability of the composition of the invention means that the composition of the invention can be used to improve bioaccessibility, bioavailability bioefficacy and/or bioactivity of curcuminoids in mammals.

The improved bioaccessibility, bioavailability, bioefficacy and/or bioactivity of curcuminoids allows for the composition of the invention to be used to prevent and/or treat diseases where in the past the poor aqueous solubility and stability of curcuminoids has been an issue.

Thus, the present invention provides a method for improving bioaccessibility, bioavailability bioefficacy and/or bioactivity of curcuminoids in mammals comprising the administration of said curcuminoids in the form of a composition of the invention as previously defined.

The method maybe referred to hereinafter as the "method of the invention".

The present invention also provides the use of a composition of the invention as previously defined for improving the bioaccessibility, bioavailability bioefficacy and/or bioactivity of curcuminoids in mammals.

The use maybe referred to hereinafter as the "use of the invention".

In the method or uses described herein the improvement in bioaccessibility, bioavailability bioefficacy and/or bioactivity of curcuminoids in mammals may be due to the composition providing improved gastrointestinal resistance of the curcuminoids and/or improved absorption of curcuminoids by intestinal cells and/or improved blood circulation.

In the methods or uses described herein the improvement in bioaccessibility, bioavailability bioefficacy and/or bioactivity of curcuminoids in mammals may be due to the composition providing improved water solubility and/or improved stability at a pH from about 4 to about 7.

Thus, the present invention provides a method for improving the water solubility and/or pH stability of curcuminoids, wherein the method comprises the administration of said curcuminoids in the form of a composition of the invention as previously defined.

The present invention also provides the use of a composition as previously defined for improving the water solubility and/or pH stability of curcuminoids.

In the methods or uses described herein, the curcuminoids may be selected from the group consisting of curcumin and its phase I or phase II metabolites, demethoxycurcumin and its phase I or phase II metabolites, bisdemethoxycurcumin and its phase I or phase II metabolites and mixtures thereof.

For example, the phase I and/or phase II metabolites may be selected from the group consisting of curcumin glucuronide, curcumin sulfate, DMC glucuronide, DMC sulfate, BDMC glucuronide, BDMC sulfate, tetrahydrocurcumin (THC), THC glucuronide, THC sulfate, hexahydrocurcumin (HHC), HHC glucuronide, HHC sulfate and mixtures thereof.

In the compositions, methods or uses described herein, the curcuminoids may be in their unmetabolized form, for example the forms or curcumin, DMC and BDMC that have not undergone glucuronide or sulfate addition.

In the methods and uses described herein, the mammal may be a human.

As used herein, the term "bioavailability" can be defined as the fraction of ingested component available at the site of action for utilization in normal physiological functions and is determined through in vivo assays (Guerra A, Etienne-Mesmin L, Livrelli V et al (2012) Relevance and challenges in modeling human gastric and small intestinal digestion. Trends Biotechnol 30:591-600). Bioavailability is the result of three main steps: digestibility and solubility of the element in the gastrointestinal tract; absorption of the element by the intestinal cells and transport into the circulation; and incorporation from the circulation to the functional entity or target (Wienk K J H, Marx J J M, Beynen A C (1999) The concept of iron bioavailability and its assessment. Eur J Nutr 38:51-75; Etcheverry P, Grusak M A, Fleige L E (2012) Application of in vitro bioaccessibility and bioavailability methods for calcium, carotenoids, folate, iron, magnesium, polyphenols, zinc, and vitamins B6, B12, D, and E. Front Physiol 3:1-21).

As used herein, the term "bioaccessibility" can be defined as the fraction of a compound that is released from its food matrix within the gastrointestinal tract and thus becomes available for intestinal absorption (typically established from in vitro procedures). It includes the sequence of events that take place during food digestion for transformation into potentially bioaccessible material but excludes absorption/assimilation through epithelial tissue and pre-systemic metabolism (both intestinal and hepatic). (Alegria A., Garcia-Llatas G., Cilla A. (2015) Static Digestion Models: General Introduction. In: Verhoeckx K. et al. (eds) The Impact of Food Bioactives on Health. Springer, Cham)

As used herein, the term "bioactivity" can be defined as how the nutrient or bioactive compound is transported and reaches the target tissue, how it interacts with biomolecules, the metabolism or biotransformation it may experience, and the generation of biomarkers and the physiological responses induced (Alegria A., Garcia-Llatas G., Cilla A. (2015) Static Digestion Models: General Introduction. In: Verhoeckx K. et al. (eds) The Impact of Food Bioactives on Health. Springer, Cham).

BRIEF DESCRIPTION OF FIGURES

Figure 1:
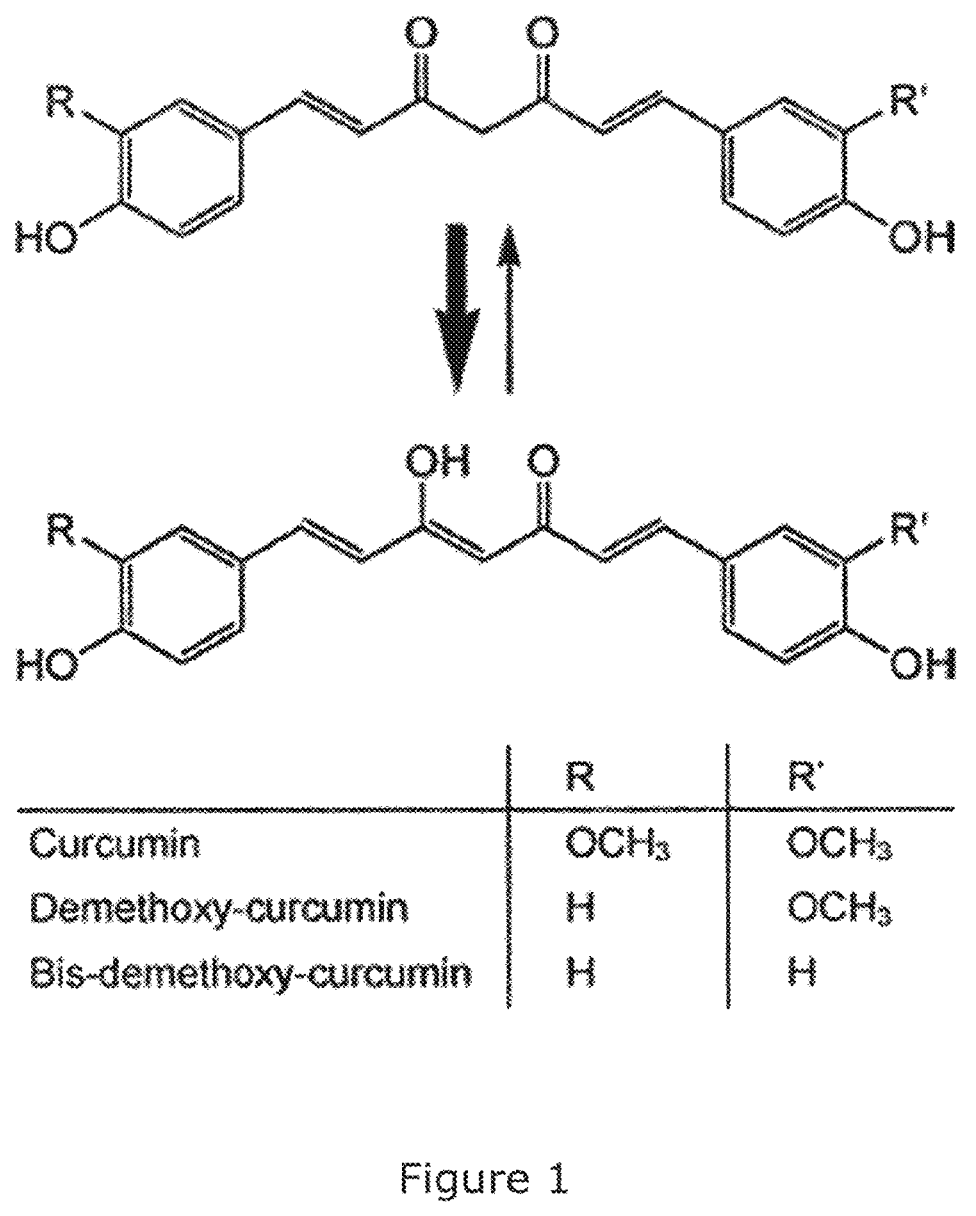

FIG. 1—Chemical structures of the curcuminoids from turmeric.

FIG. 2—Phase I and phase II metabolites of curcumin

FIG. 3—Bacterial metabolites of curcumin

FIG. 38—Flow chart of EMR-Lipid protocol for the human plasma treatment before injection.

EXAMPLES

The present invention will be further described by reference to the following, non-limiting examples.

Example 1—Preparation of Alkaline Organic Curcumin Solution

A mixture of curcuminoids in water was prepared using an organic purified curcuminoid extract (at least at 10% but preferably at 95% of purity (total curcuminoids)) in distilled water (3 volumes powder weight/water).

Example 2—Preparation of a Composition of the Invention

A 58% gum Arabic mixture (substrate) was prepared using distilled water (3 volumes powder weight/water). 500 ml of the aqueous gum arabic solution was added 500 ml of the curcuminoid solution prepared in Example 1 under agitation (5000 rpm) and to this was added 5% of organic sunflower oil and 2% of organic quillaja standardized in saponins.

The resulting mixture was agitated at 5000 rpm for ten minutes. The resulting emulsion was then spray dried.

Example 3—Characterization of a Composition of the Invention

The size and morphology of the composition of the invention was analyzed by dynamic light scattering (DLS), and zeta potential (Z-potential), and scanning electron microscopy (SEM). For DLS and zeta-potential analyses a Zetasizer Nano ZS (NanoZS90, Malvern Instrument Ltd., UK) with a He/Ne laser ($\lambda$=633 nm) at a fixed scattering angle of 90° at temperature of (25±0.1° C.) was used.

The samples used were in liquid emulsion form (last step before drying). The samples were suspended in demineralized water at a volume concentration of 0.4% and 1 minute of ultrasound was applied. DLS analysis was immediately performed at these samples (measure time=60 seconds). The analysis of zeta-potential was performed in a large pH range (from 2 to 11).

The samples were prepared and analyzed at different pHs as follows by the use of 0.1M HCl and 0.1M NaOH solutions. The 10 samples (pH=2, 3, 4, 5, 6, 7, 8, 9, 10 and 11) obtained were stored at room temperature (23° C.) (FIG. 4).

Figure 4:
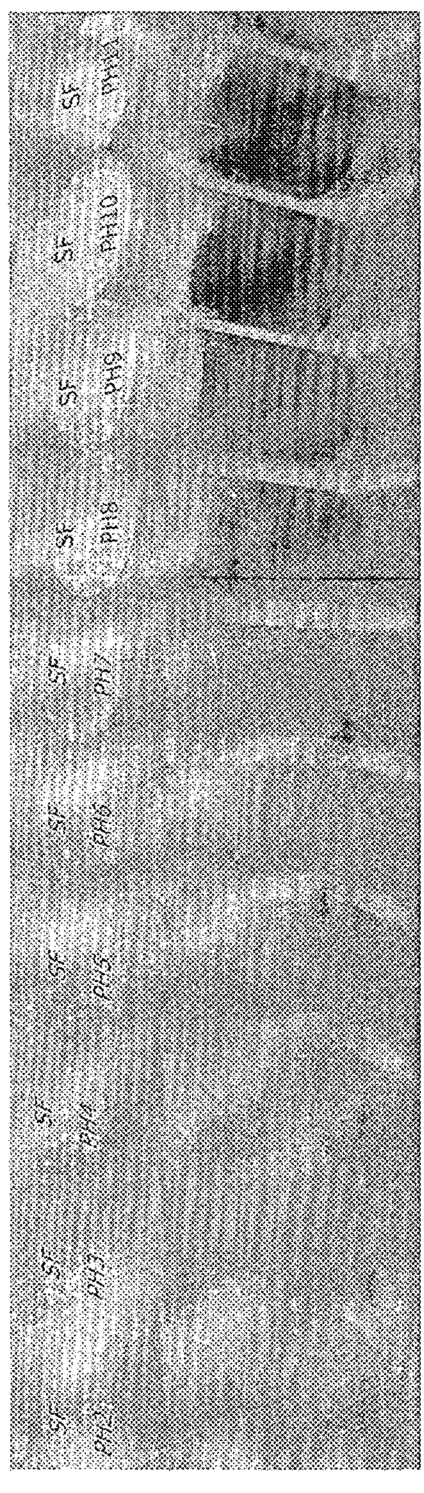
FIG. 4—the effect of pH on the composition of the invention colour dissolved in demineralized water (0.4%).

As shown in FIG. 4, the colour of the composition of the invention in water is driven by pH. The keto form (yellow) is the predominant form present in solution when pH range vary from acid to neutral (from 2- to 7). At pH 8 and 9 colour solution turns to orange, and at pH 10 and 11 a translucid reddish colour is predominant. The colour change is due to sequential deprotonation of hydroxyl-groups of curcumin molecule driven by pH increasing which gives a higher solubility and instability to curcumin.

Figure 5:
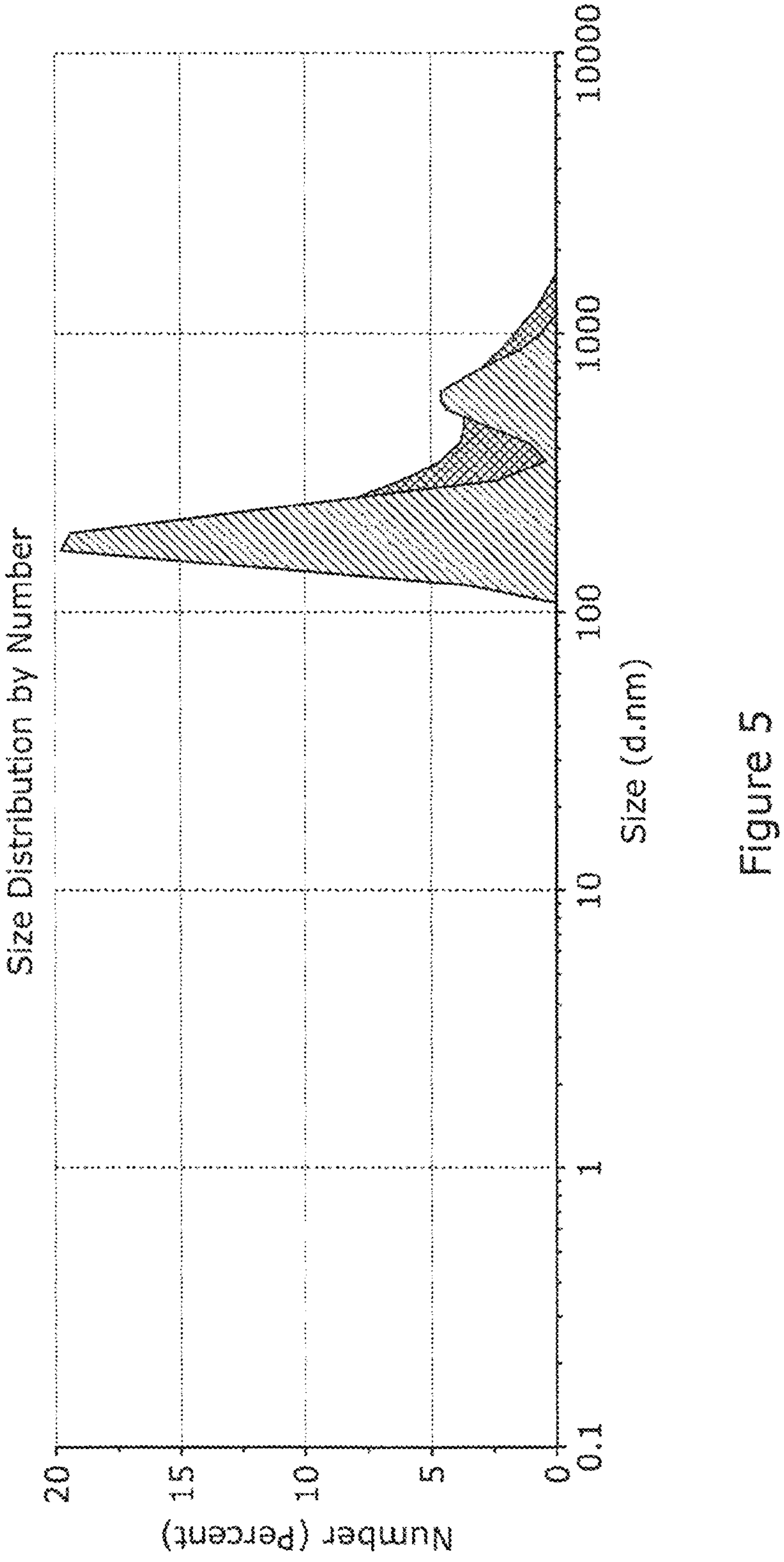
FIG. 5—the DLS profile of loaded of composition of the invention.

The DLS analysis results are showed in FIG. 5. There are two groups of particle size individuals. One centralized at 616±160 nm (20.8% of total individuals) and the most interesting one centralized at 188±42 nm (79.2% of the total individuals).

The mean hydrodynamic particle size of loaded curcumin in water solution (pH 5.4) was found to be 476.5 nm with a PDI (polydispersity index) of 0.337.

Figure 6:
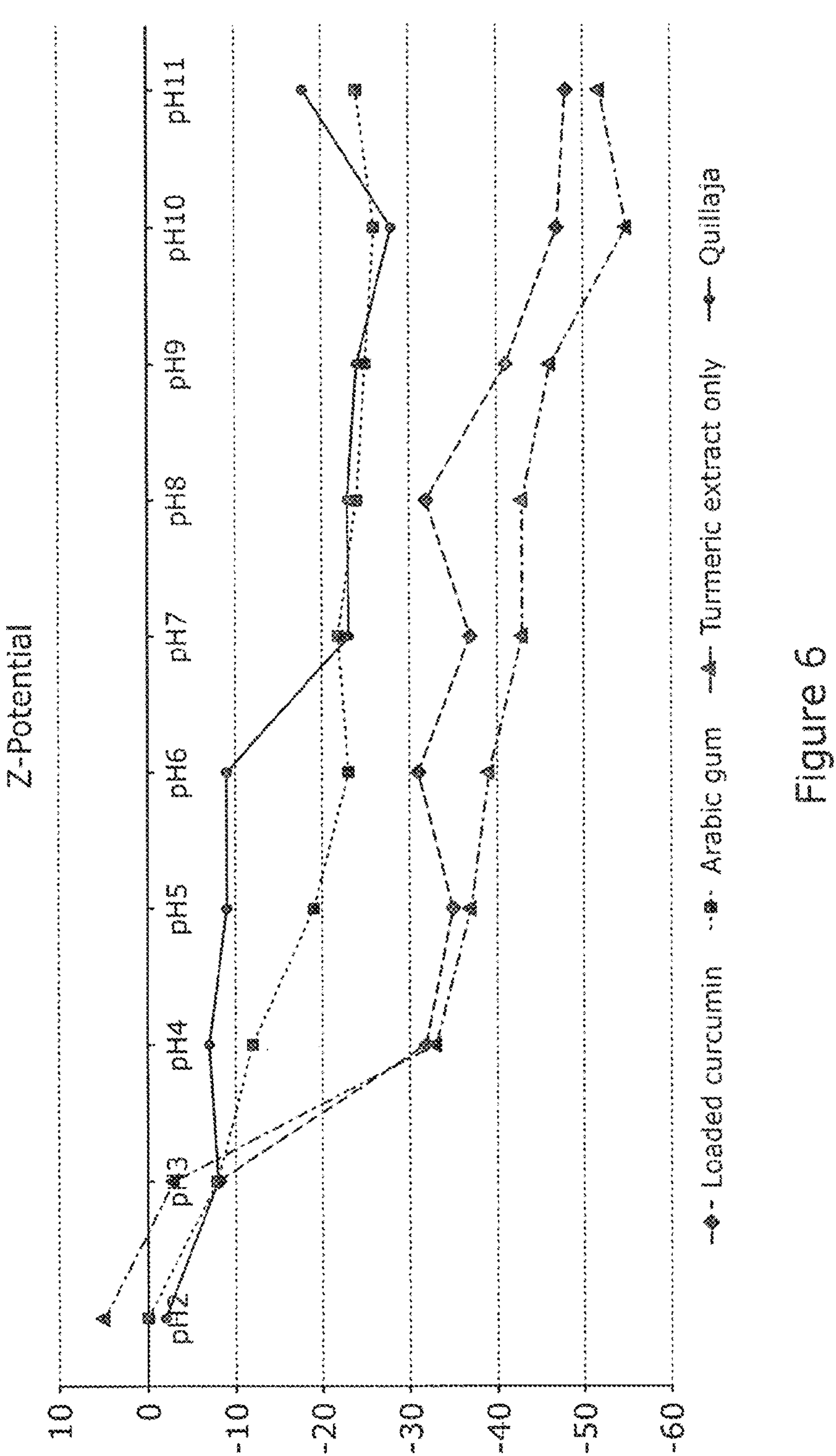
FIG. 6—The Z-potential of the composition of the invention and individual components of the composition in different pHs.

FIG. 6 shows the Z-potential of the composition of the invention at different pHs (from 2 to 11). The higher Z-potential, the more unstable mixture is. The composition of the invention has a negative Z-potential between pH 2 and pH 11. The particles are negatively charged in the aqueous phase. At pH 2 the Z-potential is close to 0 (isoelectric point: pH for which the potential is zero), where we have an instability zone of the emulsions.

Between pH 2 and pH 4, the Z-potential is relatively low (<25 mV) and at pH greater than or equal to 4, the sample enters a zone of stability. This stability is strongly confirmed from pH 5. A rapid shift in the isoelectric point was observed in pH 8.0 the zeta-potential of the loaded curcumin was surprisingly higher in pH range from 2 to 7. In the aqueous phase at pHs<4.0, loaded curcumin are usually at their lowest surface energy state. At pH 8.0, the loaded curcumin is likely to orient its low electronic charge side towards Arabic gum and expose its high electronic charge side to interact with water, which leads to an elevated zeta-potential.

FIG. 6 clearly shows that the claimed composition is stable when dispersed in an aqueous solution at pH greater than 4.

Example 4—Particle Size Distribution (PSD) of a Composition of the Invention Using CQ-MO-304

Materials and Reagents

Material—Mastersizer 3000 from Malvern Instrument, or equivalent;

- Hydro 2000SM sample dispersion unit, or equivalent (for liquid phase),
- Malvern AERO S sample dispersion unit, or equivalent (for solid phases).

Reagent—Water

Procedure

Analytical parameters

- background time: 10 seconds
- Measurement time@10 seconds
- Refractive index of distilled water: 1.33
- Result calculation: general purpose
- Pump/stir speed: 1800 RPM
- liquid dispersant: water
- solid dispersant: ambient air Specific parameters

- 100705 (refractive index: 1, adsorption: 1)
- 100019 (refractive index: 1, adsorption: 2)
- 3CAA0075 and 3CAA0076 (Composition of the invention)

A sample of the composition of the invention was mixed with distilled water and a sample was tested either using a Hydro 2000SM unit or Mastersizer 3000 (using a Scirocco 2000 unit).

Results

Several batches of the composition of the invention, obtained after drying and milling, were tested according to the above-mentioned method. The results are provided in Table 1 below.

TABLE 1

Particle Size Distribution of the composition of the invention (where (D90) corresponds to 90% of the particle size population, and (D4:3) corresponds to the volume moment mean of the particle size population).

| Ball Mill Reference | Product name | PS (D90) in μm | PS (D4:3) in μm |
|---|---|---|---|
| 3CAA0076 | Turmipure Enhanced 30%-Ball Milled | 3.3 | 1.7 |
| 3COA0004 | Organic Turmipure Enhanced 30%-Ball Milled | 3.4 | 1.6 |
| 3COA0004 | Organic Turmipure Enhanced 30%-Ball Milled | 3.5 | 2.1 |
| 3COA0004 | Organic Turmipure Enhanced 30%-Ball Milled | 2.6 | 1.6 |
| 3CAA0076 | Turmipure Enhanced 30%-Ball Milled | 2.4 | 1.4 |
| 3CAA0076 | Turmipure Enhanced 30%-Ball Milled | 3.5 | 1.8 |
| 3CAA0076 | Turmipure Enhanced 30%-Ball Milled | 3.2 | 1.5 |
| 3CAA0076 | Turmipure Enhanced 30%-Ball Milled | 3.1 | 1.5 |
| 3CAA0076 | Turmipure Enhanced 30%-Ball Milled | 2.7 | 1.3 |
| 3CAA0076 | Turmipure Enhanced 30%-Ball Milled | 3.1 | 1.5 |
| 3CAA0076 | Turmipure Enhanced 30%-Ball Milled | 3.5 | 1.7 |
| 3CAA0076 | Turmipure Enhanced 30%-Ball Milled | 2.7 | 1.4 |
| 3CAA0076 | Turmipure Enhanced 30%-Ball Milled | 4.4 | 2.0 |
| 3CAA0076 | Turmipure Enhanced 30%-Ball Milled | 3.1 | 1.5 |
| 3CAA0076 | Turmipure Enhanced 30%-Ball Milled | 3.4 | 1.6 |
| 3CAA0076 | Turmipure Enhanced 30%-Ball Milled | 3.2 | 1.6 |
| 3CAA0076 | Turmipure Enhanced 30%-Ball Milled | 3.9 | 1.7 |
| 3CAA0076 | Turmipure Enhanced 30%-Ball Milled | 3.9 | 1.8 |
| 3COA0004 | Organic Turmipure Enhanced 30%-Ball Milled | 2.9 | 1.4 |
| 3COA0004 | Organic Turmipure Enhanced 30%-Ball Milled | 3.1 | 1.4 |
| 3COA0004 | Organic Turmipure Enhanced 30%-Ball Milled | 3.1 | 1.5 |
| 3COA0004 | Organic Turmipure Enhanced 30%-Ball Milled | 3.3 | 1.5 |
| 3COA0004 | Organic Turmipure Enhanced 30%-Ball Milled | 3.2 | 1.5 |
| 3COA0004 | Organic Turmipure Enhanced 30%-Ball Milled | 3.4 | 1.6 |
| 3COA0004 | Organic Turmipure Enhanced 30%-Ball Milled | 3.2 | 1.6 |
| 3COA0004 | Organic Turmipure Enhanced 30%-Ball Milled | 3.1 | 1.4 |
| 3COA0004 | Organic Turmipure Enhanced 30%-Ball Milled | 3 | 1.5 |
| 3COA0004 | Organic Turmipure Enhanced 30%-Ball Milled | 3.2 | 1.5 |
| 3COA0004 | Organic Turmipure Enhanced 30%-Ball Milled | 2.9 | 1.5 |
| 3COA0004 | Organic Turmipure Enhanced 30%-Ball Milled | 3.2 | 1.5 |
| 3COA0004 | Organic Turmipure Enhanced 30%-Ball Milled | 3.2 | 1.5 |
| 3COA0004 | Organic Turmipure Enhanced 30%-Ball Milled | 3.1 | 1.7 |
| 3COA0004 | Organic Turmipure Enhanced 30%-Ball Milled | 2.9 | 1.4 |
| 3COA0004 | Organic Turmipure Enhanced 30%-Ball Milled | 2.96 | 1.41 |
| 3COA0004 | Organic Turmipure Enhanced 30%-Ball Milled | 3.39 | 1.59 |
| 3COA0004 | Organic Turmipure Enhanced 30%-Ball Milled | 3.2 | 1.5 |
| 3COA0004 | Organic Turmipure Enhanced 30%-Ball Milled | 3 | 1.4 |

Example 5—Morphology of a Composition of the Invention (by Scanning Electron Microscopy, SEM)

For SEM analysis samples were prepared as follow: The composition of the invention in powder form was deposited on the sample holder by simply dusting. It was followed by metallization of platinum/palladium deposits and then observation and shooting by scanning electron microscope equipped with X-ray detector in energy dispersion.

Figure 7:
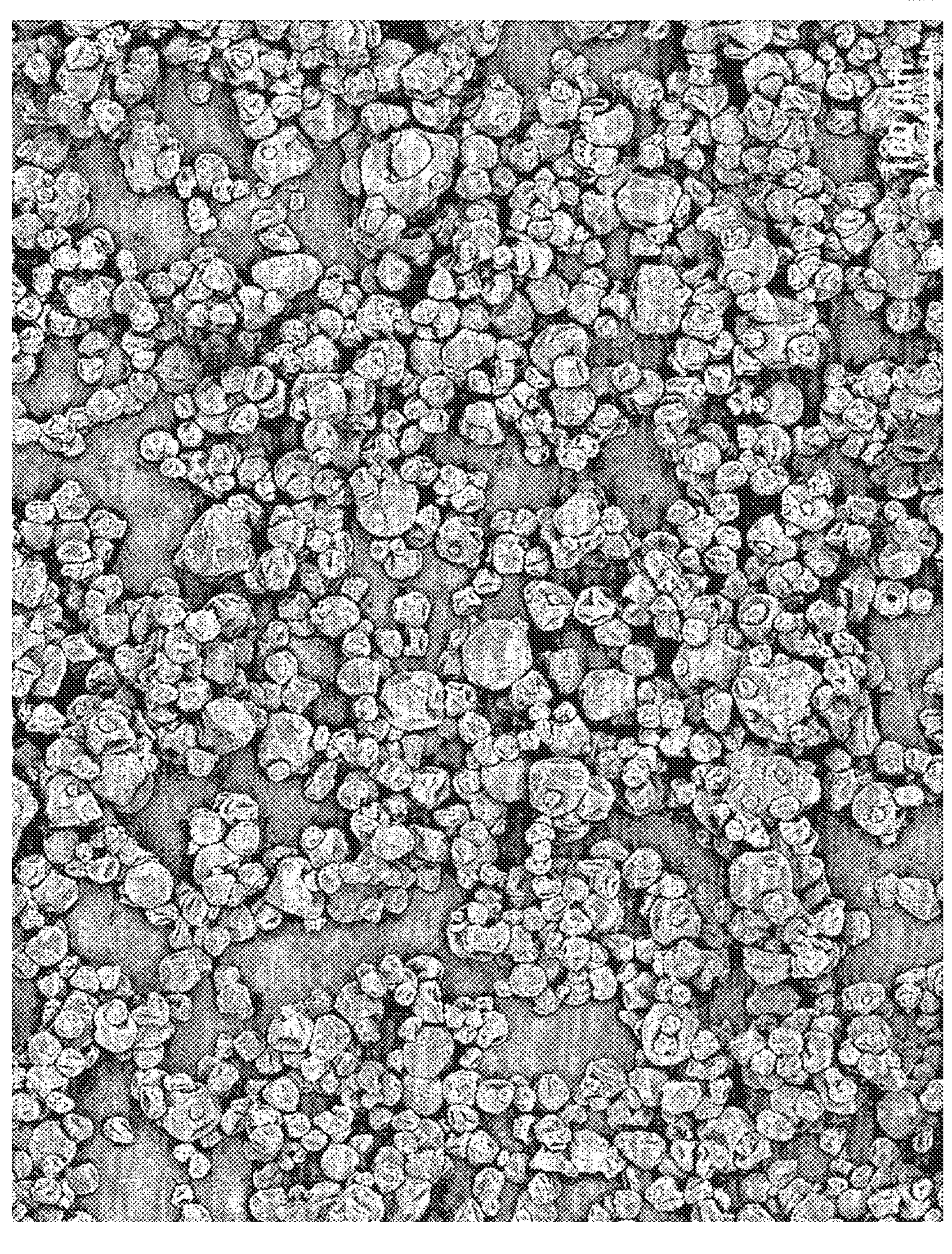
FIG. 7—Scanning electron microscopy (SEM) image of the composition of the invention at ×300.
Figure 8:
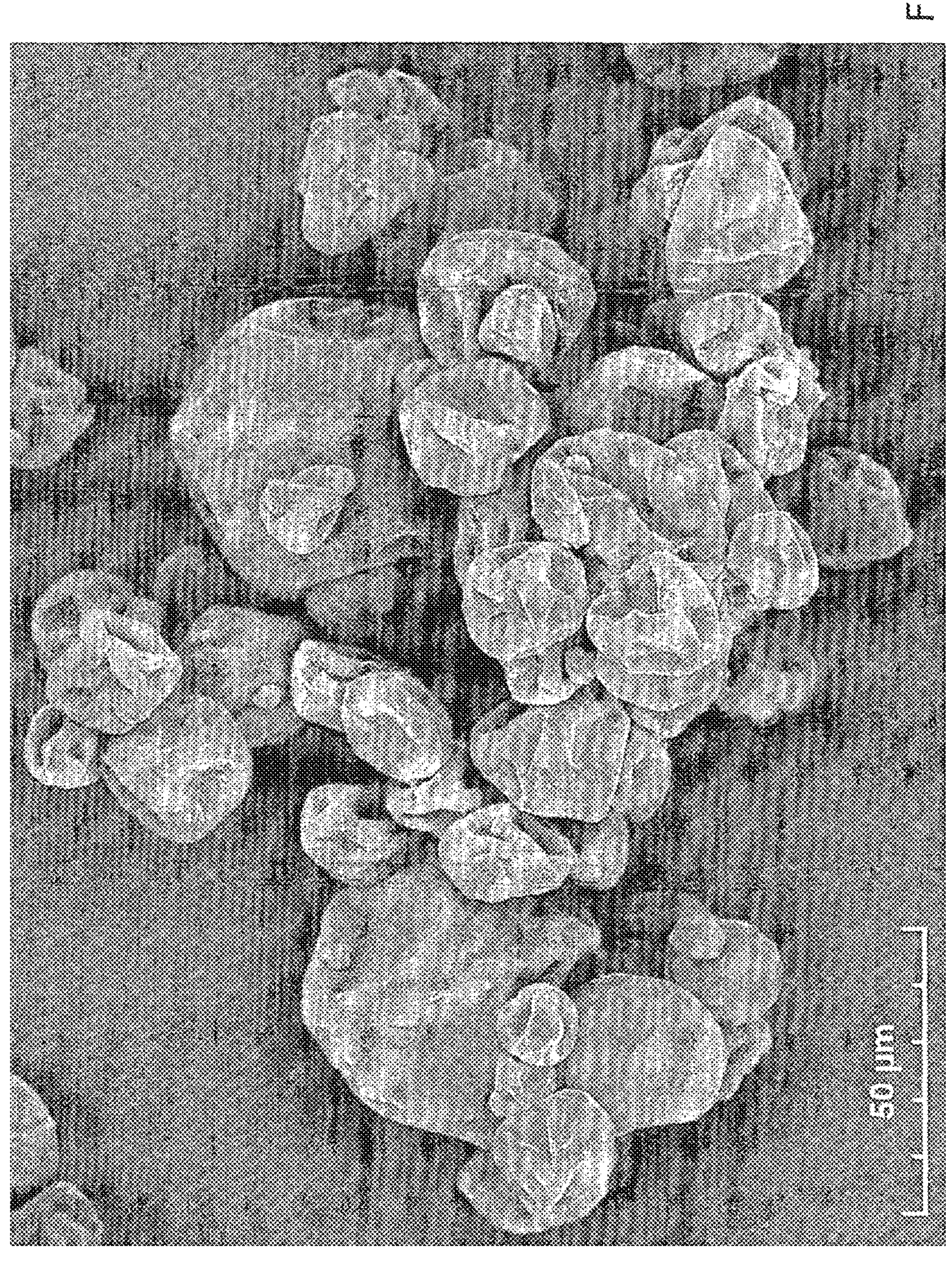
FIG. 8—Scanning electron microscopy (SEM) image of the composition of the invention at ×1300.
Figure 9:
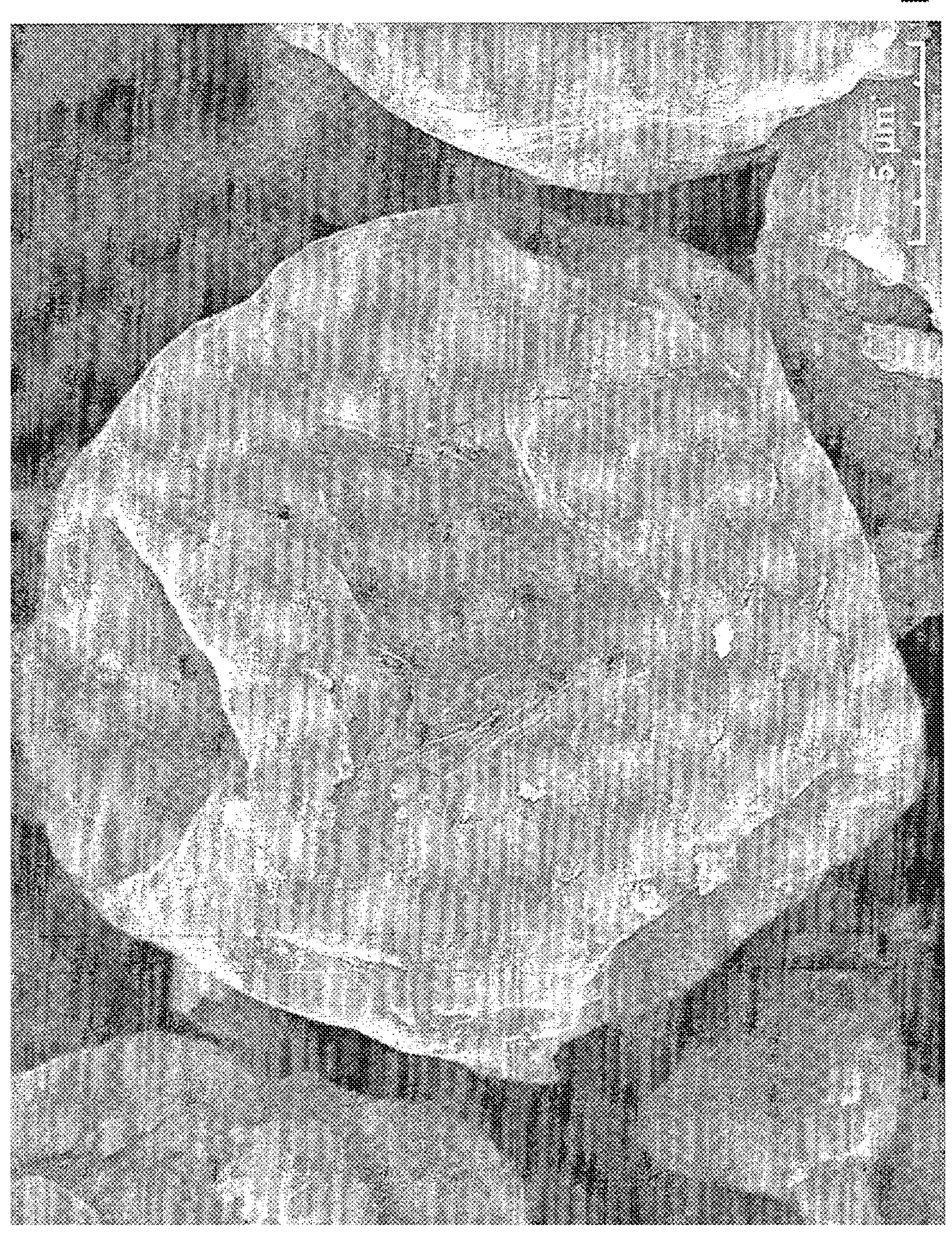
FIG. 9—Scanning electron microscopy (SEM) image of the composition of the invention at ×9200.
Figure 10:
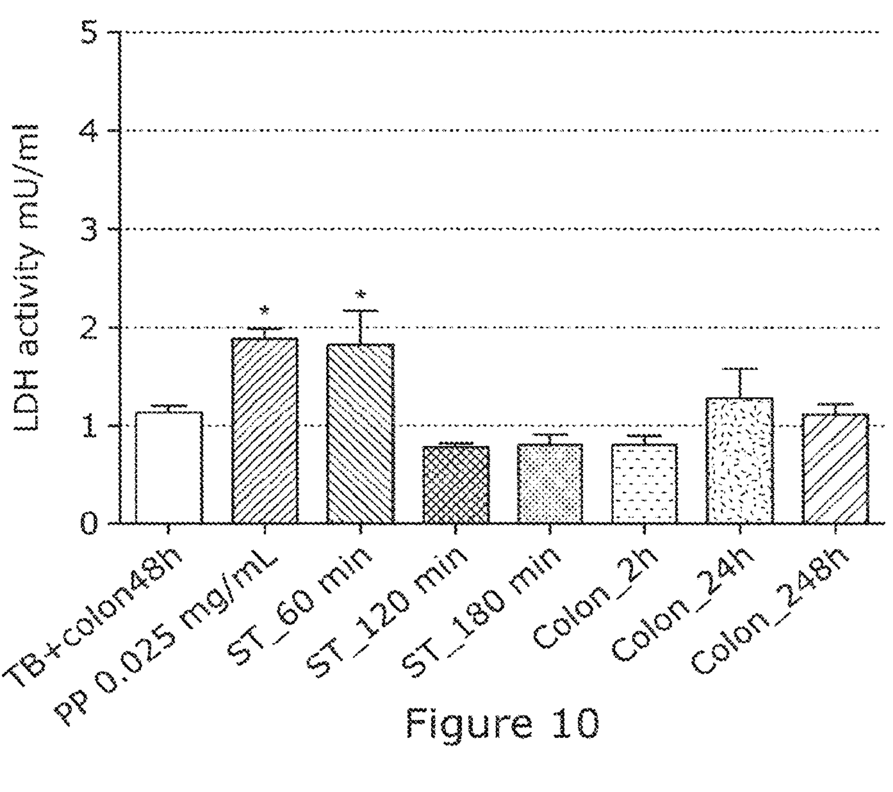
FIG. 10—LDH activity measured on the apical supernatant collected from the Caco-2 cells treated with samples coming from the different gastrointestinal tract compartments after 4 h of incubation, data from the standard curcumin extract. Bars depict Mean±SEM. PP: pure product; SI: small intestine; ST: stomach; TB: transport buffer. (*), () and (*) correspond to significances at $p<0.05$, $p<0.01$ and $p<0.001$, respectively, compared to TB+colon 48 h.
Figure 11:
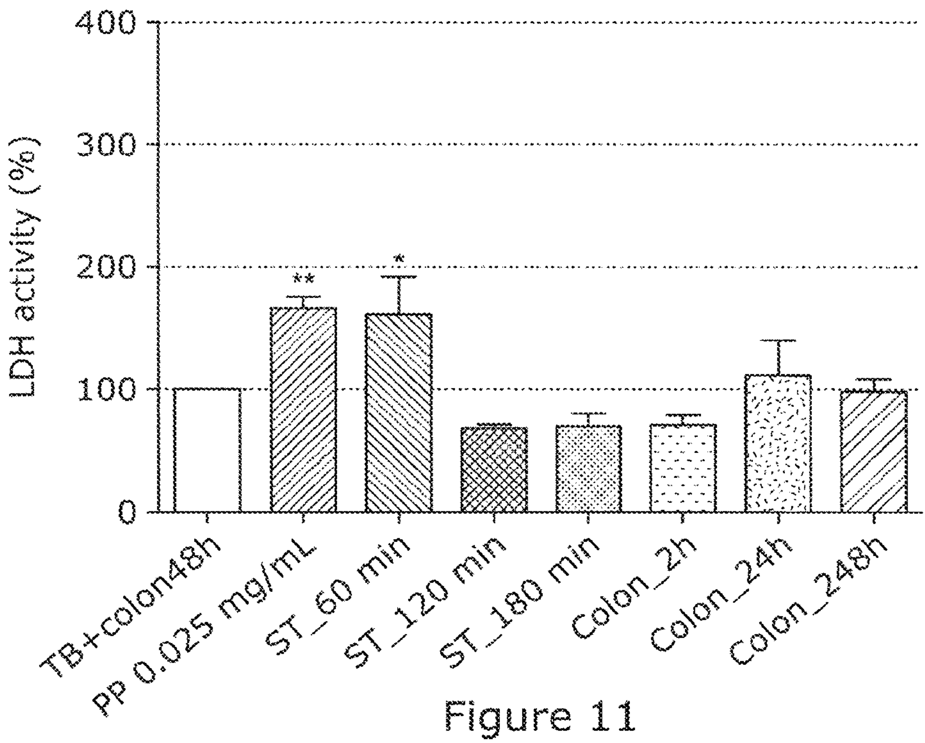
FIG. 11—LDH activity measured on the apical supernatant collected from the Caco-2 cells treated with samples coming from the different gastrointestinal tract compartments after 4 h of incubation, data from the standard curcumin extract with data normalized to the TB+colon 48 h sample (100%). Bars depict Mean±SEM. PP: pure product; SI: small intestine; ST: stomach; TB: transport buffer. (*), () and (*) correspond to significances at $p<0.05$, $p<0.01$ and $p<0.001$, respectively, compared to TB+colon 48 h.
Figures 12, 13:
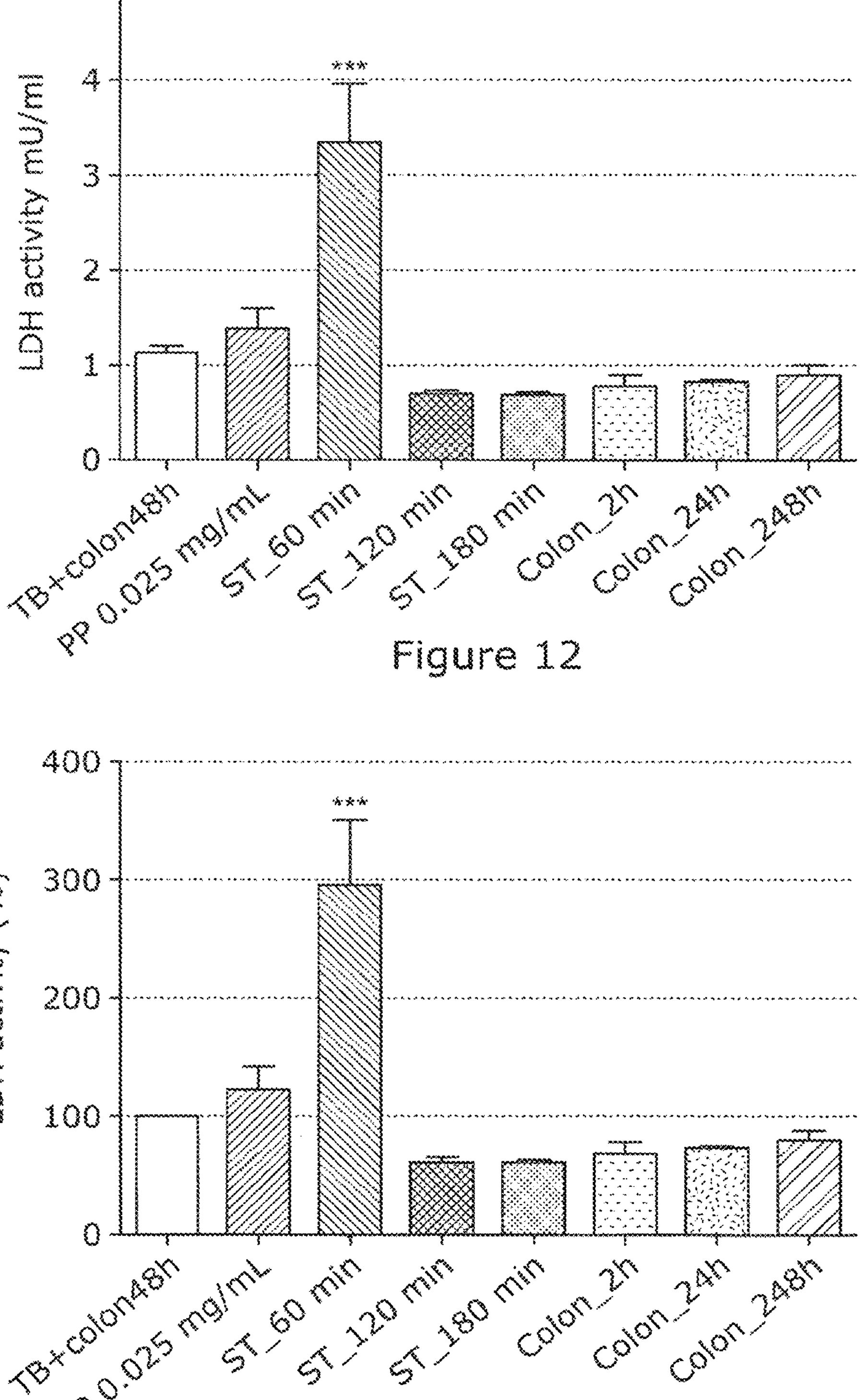
FIG. 12—LDH activity measured on the apical supernatant collected from the Caco-2 cells treated with samples coming from the different gastrointestinal tract compartments after 4 h of incubation, data from the turmeric phytosome formulation. Bars depict Mean±SEM. PP: pure product; SI: small intestine; ST: stomach; TB: transport buffer. (*), () and (*) correspond to significances at $p<0.05$, $p<0.01$ and $p<0.001$, respectively, compared to TB+colon 48 h.
FIG. 13—LDH activity measured on the apical supernatant collected from the Caco-2 cells treated with samples coming from the different gastrointestinal tract compartments after 4 h of incubation, data from the turmeric phytosome formulation with data normalized to the TB+colon 48 h sample (100%). Bars depict Mean±SEM. PP: pure product; SI: small intestine; ST: stomach; TB: transport buffer. (*), () and (*) correspond to significances at $p<0.05$, $p<0.01$ and $p<0.001$, respectively, compared to TB+colon 48 h.
Figure 14:
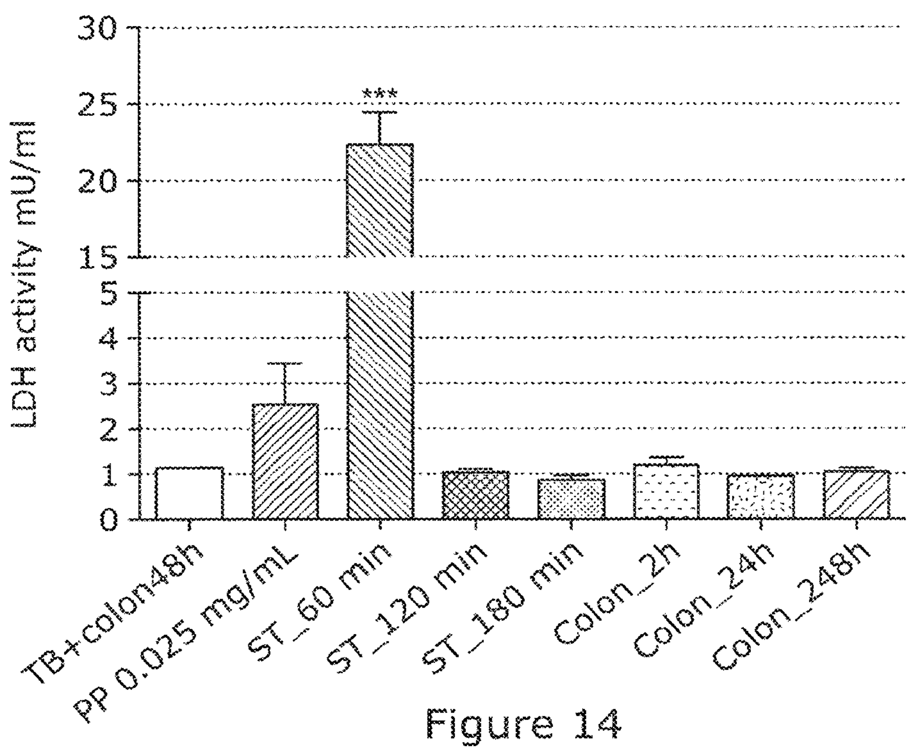
FIG. 14—LDH activity measured on the apical supernatant collected from the Caco-2 cells treated with samples coming from the different gastrointestinal tract compartments after 4 h of incubation, data from the quillaja based formulation. Bars depict Mean±SEM. PP: pure product; SI: small intestine; ST: stomach; TB: transport buffer. (*), () and (*) correspond to significances at $p<0.05$, $p<0.01$ and $p<0.001$, respectively, compared to TB+colon 48 h.
Figure 15:
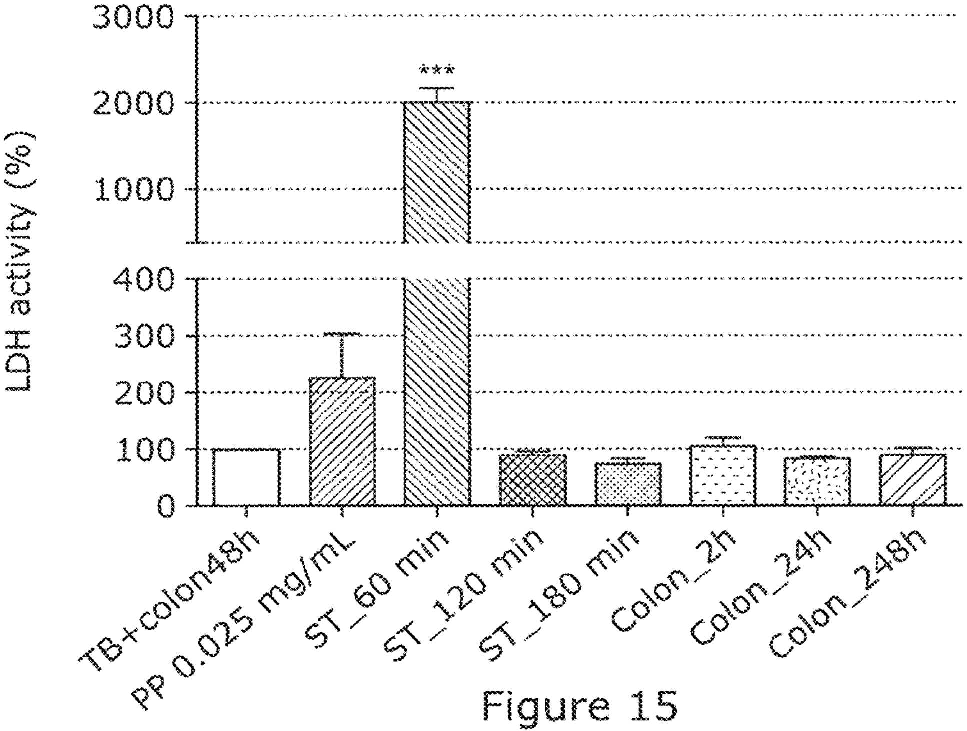
FIG. 15—LDH activity measured on the apical supernatant collected from the Caco-2 cells treated with samples coming from the different gastrointestinal tract compartments after 4 h of incubation, data from the quillaja based formulation with data normalized to the TB+colon 48 h sample (100%). Bars depict Mean±SEM. PP: pure product; SI: small intestine; ST: stomach; TB: transport buffer. (*), () and (*) correspond to significances at $p<0.05$, $p<0.01$ and $p<0.001$, respectively, compared to TB+colon 48 h.

The SEM images shown in FIGS. 7, 8 and 9 provide the visualization of the composition of the invention.

The composition of the invention shows conjugate self-assembled to spherical micelles with size of +/−170 nm. The roughly spherical morphology in SEM analysis corroborated the size measurement analysis done by dynamic light scattering technique.

From SEM, it can be seen that the particles in the composition of the invention have clearly shown outer coat of chitosan which was absent in uncoated lecithin nanoparticles. Curcumin was found to be well dispersed in the lecithin core of the nanoparticles. SEM measurements also corroborated evidence of roughly spherical geometry and the surface roughness indicate surface absorption. It suggests that the driving force of this type of adsorption is either direct electrostatic interaction or ion-ion interaction.

Example 6—Testing the Effect of a Composition of the Invention to Enhance the Bioavailability of Curcuminoids in an In-Vivo Model of the Human Gastrointestinal Tract and Intestinal Absorptive Cells The human gastrointestinal tract (GIT) is one of the major entry gates to the human body. Upon oral ingestion of foods, drinks or pharmaceuticals, the gut is the first site of contact between the ingested products and the host. In order to exert their biological activity, compounds have first to pass the stomach where the acid environment and the presence of digestive enzymes may lead to chemical or enzymatic modifications. After leaving the stomach, ingested compounds reach the small intestine, in which a major part of the host metabolic enzymes are secreted, possibly leading to further enzymatic modifications. The compound, in its original or modified form, may subsequently be absorbed and enter circulation, or may further pass through the intestine. Here, food compounds may have a local biological activity by coming into contact with the complex microbial community present in the terminal ileum (last portion of the small intestine) and the colon (Alegria et al, 2015).

Human studies are certainly one of the most representative ways to study the different intestinal processes. However, they are highly labor- and time-consuming, very costly and do not allow mechanistic studies.

In humans, the intestine can be considered a black box that allows quantifying the in- and output but investigating the underlying intestinal processes in their different compartments is difficult due to sampling issues. Moreover, ethical constraints limit the general application of human trials.

Therefore, well-designed in vitro simulation technologies offer a very useful alternative for human and animal studies. Being representative for specific processes, such models enable reproducible in-depth studies of these processes without ethical constraints. The easier setup and sampling allow medium to high throughput studies at lower costs. Nonetheless, the lack of a physiological host environment is the most important limitation of these models. However, the use of standardized in vitro cell cultures using human-derived cell lines provide a fast and reproducible way to study the ultimate effects of compounds on the intestinal mucosa. Furthermore, extensive in vitro investigation allows to carefully design subsequent animal or human studies, thereby saving time and money.

Carefully designed GIT-simulating in vitro approaches offer an excellent high-throughput screening setup to evaluate the putative metabolic fate of selected food ingredients at different concentrations. Such ingredients may be modified or modify the bacterial community in the gut, and therefore, reach the intestinal mucosa intact or in the form of a modified by-product. Oral bioavailability of dietary compounds is defined as the fraction of the administered dose able to be absorbed by the intestinal cells and that is available for use or storage.

Bioavailability of dietary compounds is dependent on many factors, namely on the nutritional and physiological status of the individual, on the conjugation of the compound with other nutrients and/or bile salts, on the enzymatic degradation of the compound by digestive enzymes, and on the capacity of the gut-associated bacteria to metabolize it. In vitro gastrointestinal model offers the possibility to screen a large set of molecules in a rapid and cost-effective way in short-term experiments.

The following approach allows to rapidly assess the intestinal fate of dietary compounds upon digestion and colon fermentation. This, associated with in vitro cell models that mimic the human intestinal epithelium, allow to investigate the bioavailability of the intact and modified compounds, thereby increasing both the scientific output and commercial relevance.

Firstly, short-term screening assays were performed as a tool to evaluate the digestive fate of curcumin-based formulations, with different solubility properties.

The results of these experiments were then applied to Caco-2 cells in vitro in order to investigate the bioavailable fraction of the different formulations, in comparison to their unmodified/undigested forms.

In addition, cellular toxicity was measured in order to compare the putative cytotoxic effects of the different digestive fractions.

The short-term screening assays consisted of the sequential incubation (stomach, small intestine, colon) of a representative dose(s) of the selected lead compounds under simulated conditions for the large intestine with a representative bacterial inoculum.

An intestinal suspension collected from the ascending colon compartment of the Simulator of the Human Intestinal Microbial Ecosystem (SHIME) was used (Van de Wiele et al, 2015).

This inoculum consists of a stable microbial community which is adapted, both in structure and activity, to the environmental conditions which are present in the proximal colon.

The following curcumin-based formulations/composition were evaluated:

1. A standard curcumin extract (*Curcuma longa*)—containing a mix of 3 curcuminoids (curcumin—75%, demethoxicurcumin (DMC)—15 to 20% and bidemethoxy-curcumin (BDMC)—5 to 10%).

2. A control formulation (Turmeric phytosome Thorne product with Meriva® which formulation comprises 18-22% curcuminoids, where the curcumin and soy lecithin present are formulated in a 1:2 weight ratio (Phytosome), and two parts of microcrystalline cellulose are then added to improve flowability, with an overall content of curcumin in the final product of around 20%.)

3. A composition as used in the methods/uses of the invention comprising 8.6% turmeric extract (with more than 6% curcuminoids), 15.9% sunflower oil, 2% quillaja extract, and 73.5% modified starch) (also referred to herein as Form I).

The short-term screening assay consisted on the sequential incubation of the three formulations under stomach, small intestine and colon conditions.

The formulations/compositions were tested to achieve a curcuminoids concentration of 0.5 g/L in the stomach compartment (the actual amount in mg was calculated based on the % of curcuminoids within each product—as shown in Table 2).

The different formulations/compositions were then incubated for 1 hour (h) at 37° C., pH 2.0, in the presence of pepsin.

The small intestine was then simulated by adding pancreatic enzymes and bile salts and samples were incubated at 37° C. for a total duration of 3 h.

Finally, in the third incubation stage, the colon was simulated by adding a representative fecal inoculum collected from the SHIME and a rich nutritional media. Colon incubations were carried out at 37° C., with shaking and under anaerobiosis, over a total duration of 48 h.

Each formulation/composition was tested in triplicate to control for biological variability.

Note that these experiments were designed in order to respect the specific residence times of food ingredients in the gastrointestinal tract. Considering the volumes within each compartment, the concentration of curcuminoids tested was: 0.5 g/L in the stomach, 0.35 g/L in the small intestine and 0.1 g/L in the colon. For the cell transport experiments these samples were diluted 10× more.

TABLE 2

Curcumin-based formulations/compositions tested and the respective curcuminoids percentage in the formulation/composition. The curcuminoids percentage was taken into account in order to calculate the amount in mg to be added to the stomach compartment. In bold is depicted the native form.

| | Curcuminoids content % | | | |
|---|---|---|---|---|
| Description | Curcumin | DMC | BDMC | Total |
| Standard Turmeric powder extract (95% curcuminoids) | 79.42 | 14.72 | 2.03 | 96.18 |
| Turmeric phytosome (Thorne product with Meriva ®) | 13.43 | 2.70 | 0.28 | 16.40 |
| A composition as used in the methods/uses of the invention comprising turmeric extract, sunflower oil, quillaja extract and modified starch | 5.50 | 0.77 | 0.08 | 6.35 |

Samples for each formulation/composition were collected at the following time points:

Stomach: 30 min and 60 min

Small intestine: 60, 120 and 180 min

Colon: 2, 4, 6, 24 and 48 hours

The samples were then analyzed for their curcuminoids content (curcumin, DMC and BDMC) using high pressure liquid chromatography (HPLC) coupled with mass spectrometry.

A calibration curve was prepared in the range 2-1000 ng/mL for each 3 curcuminoids (Phytolab, Vestenbergsgreuth, Germany) adding 54 ppb of curcumin-d6 (TLC pharmachem, Ontario, Canada) as an internal standard to ensure retention time stability and instrument correction variation. Acetonitrile was used as the diluent for each solution. For free curcuminoid determination, exactly 450 μL of internal standard solution (60 ng/mL) was loaded over 50 μL of plasma sample into Captiva 96 wells plate (ND lipids from Agilent). After mixing and filtration the eluate is ready to be injected into LC/MS system. Captiva ND Lipid plates are designed to effectively remove phospholipids from plasma. For the determination of total conjugated curcuminoid metabolites (glucuronide and sulfate metabolites), 100 μL of plasma sample was mixed with 100 μL of enzyme solution (either glucuronidase 1000 units/mL, Sigma #G7017; or sulfatase, Sigma #S9626, 100 units/mL) for 2 hours at 37° C. After this hydrolysis step, 50 μL of the solution is mixed with 450 μL of acetonitrile onto Captiva 96 wells plate as well. The sample procedure is the same than for free curcuminoids, mixing and filtering before injection.

LC/MS conditions were then as follows. The autosampler (5° C.) and LC system used was an Agilent Infinity 1290 integrated system. Agilent 6420 Triple quadrupole mass spectrometer was used during the study, with electrospray ionization. The metabolites were eluted from the BEH Shield RP 18 column (100×2.1, 1.7 μm; Waters) with a mobile phase consisting of 0.1% formic acid in water in HPLC grade (solvent A) and 0.1% formic acid in acetonitrile (solvent B), at a flow rate of 0.5 mL/min. The elution was in gradient from 40-80% B at 0-6 min. The injection volume was 2 μL for standard and samples. For each reference compound, a relevant transition of the precursor-to-product ions were detected with the utilization of the multiple reaction monitoring (MRM) mode. For each of the 3 analytes was determined in MS1 full scan tests and the product ions in MS/MS experiments. MRM transitions of each analyte were optimized using direct infusion and Optimizer B.08.00 workstation software solution (Agilent technologies, Santa Clara, CA, USA). See Table 2a for the optimal selected conditions. The mass spectrometer parameters were set as follows: ESI source both in negative and positive mode; drying gas (N2) flow rate, 10 L/min; gas temperature, 350° C.; nebulizer, 40 psi; and capillary, 4.0 kV. The MS system fully calibrated prior to running according to manufacturer's guidelines. Data analysis were carried out on Agilent MassHunter Quantitative/Qualitative analysis B.07.00 (Agilent technologies, Santa Clara, CA, USA).

TABLE 2a

Retention times (Tr), multiple reaction monitoring (MRM) transitions, and optimized tandem mass spectrometry (MS/MS) detection parameters of 3 curcuminoids and internal standard.

| Compounds | Rt (min) | ISTD? | Prec. Ion Q1 Mass (Da) | Prod. ions Q3 Mass (Da) | Dwell Time (ms) | Frag (V) | CE (V) | Polarity |
|---|---|---|---|---|---|---|---|---|
| Curcumine d6 | 3.25 | yes | 375.2 | 291.1 | 50 | 110 | 12 | positive |
| | | | | 180.1 | | 110 | 18 | |
| Curcumine | 3.29 | No | 369.1 | 285.1 | | 98 | 13 | |
| | | | | 177.1 | | 98 | 25 | |
| DMC | 3.49 | No | 339.1 | 255.1 | | 110 | 12 | |
| | | | | 177.1 | | 110 | 16 | |
| BDMC | 3.68 | No | 309.1 | 225.1 | | 110 | 12 | |
| | | | | 119.1 | | 110 | 36 | |

Table 3 depicts the concentration in curcuminoids obtained among the intestinal tract compartments during digestion.

Surprisingly the concentrations after digestion in the stomach after 60 min and the small intestine after 120 min and 180 min for the composition as used in the methods/uses of the invention were superior than the ones obtained for the standard turmeric powder extract, demonstrating a better resistance to digestion for the composition as used in the methods/uses of the invention in comparison to the standard extract. Also, the concentrations after digestion in the stomach after 60 min and the small intestine after 120 min and 180 min for the composition as used in the methods/uses of the invention were higher than the ones of the comparator Turmeric phytosome formulation, demonstrating a better resistance to digestion for the composition as used in the methods/uses of the invention in comparison to the Turmeric phytosome comparator.

Table 4 shows the percentage of curcuminoids that remained in the intestinal compartments after digestion according to the initial concentrations (0.5 g/l or 500 mg/l of curcuminoids in the stomach compartment at the beginning of the experiments). The results clearly show that surprisingly, curcuminoids coming from the composition as used in the methods/uses of the invention had a far better resistance to digestion in the stomach and small intestine in comparison to curcuminoids coming from the standard turmeric extract and composition as used in the methods/uses of the invention are more protected from degradation during digestion after oral consumption then curcuminoids from the standard extract or the Turmeric phytosome formulation and that there are much more curcuminoids accessible for absorption in the small intestine compartment after oral consumption of the composition as used in the methods/uses of the invention than oral consumption of the standard extract or the turmeric phytosome formulation.

TABLE 3

Concentration of curcuminoids in the different compartments of the gastro-intestinal tract during the digestion process for the three formulations

| Concentration after digestion | Standard Turmeric powder extract | | | | Turmeric phytosome (Thorne product with Meriva ®) | | | | The composition as used in the methods/uses of the invention | | | |
|---|---|---|---|---|---|---|---|---|---|---|---|---|
| (ppm or mg/l) | Curcumin | DMC | BDMC | Total | Curcumin | DMC | BDMC | Total | Curcumin | DMC | BDMC | Total |
| Initial | 412.915 | 76.511 | 10.573 | 500.000 | 409.451 | 82.165 | 8.384 | 500.000 | 433.018 | 60.678 | 6.304 | 500.000 |
| | 412.915 | 76.511 | 10.573 | 500.000 | 409.451 | 82.165 | 8.384 | 500.000 | 433.018 | 60.678 | 6.304 | 500.000 |
| | 412.915 | 76.511 | 10.573 | 500.000 | 409.451 | 82.165 | 8.384 | 500.000 | 433.018 | 60.678 | 6.304 | 500.000 |
| ST60 min | 239.880 | 45.610 | 6.523 | 292.013 | ND | | | | 398.600 | 81.901 | 11.880 | 492.381 |
| | 162.430 | 31.080 | 5.108 | 198.618 | | | | | 345.510 | 71.428 | 10.983 | 427.921 |
| | 125.390 | 27.570 | 4.564 | 157.524 | | | | | 426.930 | 88.494 | 12.595 | 528.019 |
| Mean | 175.900 | 34.753 | 5.399 | 216.052 | | | | | 390.347 | 80.608 | 11.819 | 482.774 |
| SD | 58.421 | 9.565 | 1.011 | 68.919 | | | | | 41.333 | 8.606 | 0.808 | 50.736 |
| SI 120 min | 36.417 | 8.723 | 3.772 | 48.912 | 107.857 | 23.464 | 5.250 | 136.571 | 325.371 | 58.626 | 11.509 | 395.506 |
| | 53.372 | 11.500 | 4.407 | 69.279 | 108.571 | 23.957 | 5.200 | 137.729 | 342.014 | 66.726 | 10.613 | 419.353 |
| | 39.145 | 9.041 | 3.940 | 52.126 | 109.286 | 31.286 | 6.957 | 147.529 | 312.314 | 61.350 | 9.924 | 383.588 |
| Mean | 42.978 | 9.755 | 4.040 | 56.772 | 108.571 | 26.236 | 5.802 | 140.610 | 326.567 | 62.234 | 10.682 | 399.482 |
| SD | 9.104 | 1.520 | 0.329 | 10.950 | 0.714 | 4.380 | 1.000 | 6.020 | 14.886 | 4.122 | 0.795 | 18.211 |
| SI 180 min | 36.188 | 8.150 | 3.699 | 48.037 | 110.000 | 24.564 | 5.057 | 139.621 | 276.500 | 54.060 | 9.117 | 339.677 |
| | 34.933 | 8.500 | 3.861 | 47.294 | 110.714 | 28.243 | 5.793 | 144.750 | 236.500 | 46.564 | 8.105 | 291.169 |
| | 40.275 | 9.211 | 4.433 | 53.919 | 61.329 | 29.569 | 6.604 | 97.501 | 301.729 | 58.411 | 10.343 | 370.483 |
| Mean | 37.132 | 8.620 | 3.998 | 49.750 | 94.014 | 27.459 | 5.818 | 127.291 | 271.576 | 53.012 | 9.188 | 333.776 |
| SD | 2.793 | 0.541 | 0.386 | 3.629 | 28.309 | 2.593 | 0.774 | 25.926 | 32.892 | 5.993 | 1.121 | 39.985 |
| Colon 2 h | 15.623 | 11.508 | 9.989 | 37.119 | 7.521 | 6.810 | 2.280 | 16.611 | 5.248 | 3.554 | 1.647 | 10.449 |
| | 12.307 | 9.337 | 7.965 | 29.609 | 8.137 | 9.334 | 4.403 | 21.873 | 5.783 | 3.660 | 1.497 | 10.939 |
| | 11.896 | 11.535 | 11.990 | 35.420 | 6.263 | 6.628 | 2.742 | 15.632 | 4.820 | 3.443 | 1.731 | 9.994 |
| Mean | 13.275 | 10.793 | 9.981 | 34.049 | 7.307 | 7.590 | 3.141 | 18.039 | 5.284 | 3.552 | 1.625 | 10.461 |
| SD | 2.043 | 1.261 | 2.013 | 3.938 | 0.955 | 1.512 | 1.116 | 3.357 | 0.482 | 0.108 | 0.119 | 0.473 |
| Colon 24 h | 11.364 | 5.136 | 1.785 | 18.284 | 7.815 | 4.405 | 1.171 | 13.391 | 4.408 | 1.744 | 0.551 | 6.703 |
| | 10.001 | 4.828 | 1.820 | 16.649 | 7.187 | 4.392 | 1.154 | 12.732 | 4.427 | 1.788 | 0.569 | 6.783 |
| | 9.297 | 4.358 | 1.249 | 14.903 | 0.896 | 0.734 | 0.218 | 1.847 | 4.073 | 1.460 | 0.292 | 5.824 |

TABLE 3-continued

Concentration of curcuminoids in the different compartments of the gastro-intestinal tract during the digestion process for the three formulations

| Concentration after digestion | Standard Turmeric powder extract | | | | Turmeric phytosome (Thorne product with Meriva ®) | | | | The composition as used in the methods/uses of the invention | | | |
|---|---|---|---|---|---|---|---|---|---|---|---|---|
| (ppm or mg/l) | Curcumin | DMC | BDMC | Total | Curcumin | DMC | BDMC | Total | Curcumin | DMC | BDMC | Total |
| Mean | 10.220 | 4.774 | 1.618 | 16.612 | 5.299 | 3.177 | 0.847 | 9.323 | 4.303 | 1.664 | 0.470 | 6.437 |
| SD | 1.051 | 0.392 | 0.320 | 1.691 | 3.826 | 2.116 | 0.545 | 6.483 | 0.199 | 0.178 | 0.155 | 0.532 |
| Colon 48 h | 6.469 | 2.303 | 0.549 | 9.320 | 5.158 | 2.926 | 0.727 | 8.811 | 2.453 | 0.870 | 0.199 | 3.521 |
| | 4.992 | 2.403 | 0.697 | 8.091 | 3.750 | 2.423 | 0.614 | 6.786 | 2.976 | 1.197 | 0.303 | 4.476 |
| | 6.383 | 2.858 | 0.837 | 10.077 | 4.438 | 2.488 | 0.609 | 7.535 | 3.285 | 1.192 | 0.315 | 4.792 |
| Mean | 5.948 | 2.521 | 0.694 | 9.163 | 4.448 | 2.612 | 0.650 | 7.711 | 2.905 | 1.086 | 0.272 | 4.263 |
| SD | 0.829 | 0.296 | 0.144 | 1.002 | 0.704 | 0.274 | 0.067 | 1.024 | 0.420 | 0.188 | 0.064 | 0.661 |

Each formulation was tested in triplicate; the results present the mean and SD of the 3 experiments. DMC: Demethoxycurcumin; BDMC: Bisdemethoxycurcumin; ND: Not determined; SD: Standard deviation; ST: Stomach; SI: Small Intestine

TABLE 4

Resistance to Gastro-intestinal (GIT) digestion: percentage of curcuminoids that remained in the intestinal compartments after digestion according to the initial concentration

| Resistance to GIT digestion (% of initial concentration) | Standard Turmeric powder extract | Turmeric phytosome (Thorne product with Meriva ®) | The composition as used in the methods/uses of the invention |
|---|---|---|---|
| Stomach 60 min | 43.21 ± 13.78% | ND | 96.55 ± 10.15% |
| SI 120 min | 11.35 ± 2.19% | 28.12 ± 1.20% | 79.90 ± 3.64% |
| SI 180 min | 9.9 5 ± 0.73% | 25.46 ± 5.19% | 66.76 ± 8.00% |
| Colon 2 h | 6.81 ± 0.79% | 3.61 ± 0.67% | 2.09 ± 0.09% |
| Colon 24 h | 3.32 ± 0.34% | 1.86 ± 1.30% | 1.29 ± 0.11% |
| Colon 48 h | 1.83 ± 0.20% | 1.54 ± 0.20% | 0.85 ± 0.13% |

The data shows mean ± SD of the percentage of curcuminoids concentration in the different compartments and the different times after digestion in comparison to the initial concentration.

The following samples were also collected for the transport experiments on Caco-2 cells:

Small intestine: 120 and 180 min

The pH of the samples to be applied to the cells was adjusted to 6.5 prior to use.

Caco-2 cells are widely used as a cellular model for intestinal function, as they are able to spontaneously differentiate into enterocyte-like cells in culture. When cultured in semi-permeable supports, these cells develop into a functional polarized monolayer that resembles the intestinal epithelia, with the presence of apical brush-border enzymes and microvilli. Therefore, because they acquire in culture morphological and functional characteristics of mature enterocytes, they are considered as the "gold standard" model for transport experiments (Sambuy et al, 2002).

Caco-2 cells (ATCC) were seeded in 12-transwell inserts (0.4 μm) at a density of 0.9×105 cells/cm$^2$, corresponding to 1×105 cells/insert. Cells were let differentiate until a functional monolayer was reached (21 days); the apical (600 μL) and the basolateral (1500 μL) media were replenished three times a week. On the day of the experiment, the barrier function was assessed by measuring the transepithelial electrical resistance (TEER) of the monolayer. Cells were washed with HBSS to remove traces of media, and 2 mL of transport buffer (TB) was added to the basolateral side. The samples collected from the short-term experiments were diluted in transport buffer at 1:10 (v/v) ratio and given apically to the cells (600 μL). All products were also tested unprocessed and the powders diluted in TB at a concentration of 0.025 mg/mL (the final theoretical concentrations of curcuminoids tested for all formulations can be seen in Table 2a). These dilutions were prepared from stock solutions (250 mg/mL) prepared in HBSS, except for the standard turmeric extract, which was dissolved in DMSO, due to its poor solubility. As control wells, we have used colon samples (48 h incubation) diluted 1:10 (v/v) in TB obtained by running during the short-term experiments a blank (no curcumin). The transport buffer (TB) consisted of HBSS (pH 7.4) supplemented with 10 mM HEPES, 25 mM D-Glucose and 1× antibiotic-antimycotic. Cells were incubated for a total duration of 4 h at 37° C.

The following samples were collected:

1. Diluted samples that were used to stimulate the cells (500 μL). These correspond to a 0 h time point, as it contains the diluted samples before being given to the cells unprocessed formulations diluted in TB at a concentration of 0.025 mg/mL were also shipped.

2. Samples from the apical side collected after 2 h and 4 h of incubation (250 μL each).

3. Samples from the basolateral side collected after 2 h (800 μL) and 4 h (1000 μL) of incubation.

4. Samples from the cells after 4 h of incubation. These correspond to the fraction which has been uptaken inside the cells. Briefly, ice-cold PBS 1× was added to the cells to terminate the transport. Then, the cells were washed once more with PBS 1× to remove traces of product which has not been internalized, and cells were permeabilized with a solution of PBS 1× containing 20% of ethanol and 0.1% Tween-20 (600 μL); after 20 min in this solution, the cells were collected into a 1.5 mL tube and disrupted and homogenized with the help of a syringe and a 21 G needle. The tubes were centrifuged and the supernatant transferred into a new tube (450 μL).

All samples were stored at −20° C. until HPLC analysis.

In order to evaluate the cytotoxicity of the different samples applied to Caco-2 cells, lactate dehydrogenase (LDH) released by Caco-2 cells on the apical side (after 4 h of incubation) was evaluated by using a LDH-Activity Kit. LDH is released into the supernatant by cells upon membrane injury, and is therefore a marker for cell death.

Statistical analysis was done using a one-way ANOVA followed by a Dunnett's post-hoc multiple comparison test. (*), () and (*) correspond to significances at $p<0.05$, $p<0.01$ and $p<0.001$, respectively.

As shown in FIG. 10 to 15, the control wells (TB+colon 48 h) show a LDH activity around 1.0. As it is possible to see, for all products, both the undigested form as well as the stomach samples collected after 60 min shown the highest LDH activity when compared to the control.

In contrast, both small intestine and colon samples show levels comparable to the control or lower. These results demonstrated that except from samples coming from the stomach, all samples exhibited no toxicity on Caco-2 cells and results of the assays testing transport and bioavailability of curcuminoids from the samples in Caco-2 cells could be exploited and judged as valid because obtained on viable cells.

Samples from the apical, basolateral and intracellular compartments of Caco-2 cells incubated with either undigested products or with samples coming from the small intestine (120 min or 180 min) were further analyzed for their curcuminoids content (curcumin, DMC and BDMC) and their relative metabolites content (Curcumin sulfate, curcumine glucuronide, DMC sulfate and DMC glucuronide, BDMC sulfate and BDMC glucuronide) as Caco-2 cells are known to express UDP-Glucuronosyltransferases and sulfotransferases (Siissalo S, Zhang H, Stilgenbauer E, Kaukonen A M, Hirvonen J, Finel M. The expression of most UDP-glucuronosyltransferases (UGTs) is increased significantly during Caco-2 cell differentiation, whereas UGT1A6 is highly expressed also in undifferentiated cells. Drug Metab Dispos. 2008 November; 36(11):2331-6) therefore being able to metabolize curcumin, DMC and BDMC in their glucuronide or sulfate metabolites (Dempe J S, Scheerle R K, Pfeiffer E, Metzler M. Metabolism and permeability of curcumin in cultured Caco-2 cells. Mol Nutr Food Res. 2013 September; 57(9):1543-9).

The apparent permeability coefficient ($P_{app}$) values for the apical to basolateral transition were calculated according to Artursson and Karlsson using the formula:

$$P_{app}\ [\text{cm/s}]=(Vapi/(A*t))*(Cbaso/Capi)$$

where Vapi is the volume of the apical compartment (0.6 mL), A is the surface area of the monolayer (1.131 $cm^2$), t is the time (s), Cbaso is the concentration (ppm) of the total curcuminoids and their metabolites in the basolateral compartment (sum of parent compound and metabolites), and Capi is the initial concentration (ppm) of total curcuminoids in the apical compartment.

The table 5 depicts the $P_{app}$ values for different time intervals after apical exposure of Caco-2 cells to the standard extract or the 2 different formulations (Turmeric phytosome or the composition as used in the methods/uses of the invention).

TABLE 5

$P_{app}$ values of total curcuminoids and their metabolites (expressed as $10^{-7}$ cm/s) calculated for different time intervals after apical exposure of Caco-2 cells to the standard extract or the 2 different formulations

| $P_{app}$ ($\times 10^{-7}$ cm/s) | After 2 h of incubation | After 4 h of incubation |
|---|---|---|
| Standard Turmeric powder extract | 2.13 ± 0.23 | 1.10 ± 0.07 |
| Turmeric phytosome (Thorne product with Meriva ®) | 9.94 ± 0.20 (4.7) | 5.33 ± 0.25 (4.8) |
| The composition as used in the methods/uses of the invention with turmeric extract, sunflower oil, quillaja extract and modified starch | 41.01 ± 1.37 (19.3) [4.1] | 22.33 ± 0.43 (20.3) [4.2] |

The data shows mean ± SD. The fold increase in $P_{app}$ relative to standard extract is shown into brackets ( ). The fold increase in $P_{app}$ relative to turmeric phytosome formulation is shown in square brackets [ ].

As shown in table 5, the apparent permeability coefficient ($P_{app}$) values for the apical to basolateral transition was surprisingly higher for the composition as used in the methods/uses of the invention then for the standard turmeric extract, with a fold increase of 19.3 and 20.3 in $P_{app}$ value relative to standard turmeric extract respectively at 2 h and 4 h.

The apparent permeability coefficient ($P_{app}$) value for the apical to basolateral transition was also higher for the Turmeric phytosome formulation, which was used as a positive control for an enhanced bioavailability formulation, then for the standard turmeric extract, with a fold increase of 4.7 and 4.8 in $P_{app}$ relative to standard turmeric extract respectively at 2 h and 4 h. But the results show that absorption of curcuminoids by Caco-2 absorptive cells was greater for the composition as used in the methods/uses of the invention ($P_{app}$ value 4.1-fold and 4.2-fold superior at 2 h and 4 h respectively) in comparison to the comparator turmeric phytosome formulation.

Table 6 depicts the $P_{app}$ values after apical exposure of Caco-2 cells to the small intestine digestion samples (120 or 180 min) of the standard extract or the 2 different formulations (Turmeric phytosome or the composition as used in the methods/uses of the invention) using the quantified concentrations of curcuminoids in the small intestine compartments at 120 min or 180 min as Capi. It reflects the absorption capacity of curcuminoids from the digested formulation by the cells. When standard extract or formulations have been digested in the stomach and small intestine compartments and therefore samples coming from the small intestine (120 min or 180 min) are used to measure the absorption of curcuminoids by Caco-2 cells, we demonstrated that absorption of curcuminoids by Caco-2 absorptive cells was greater for the composition as used in the methods/uses of the invention ($P_{app}$ value 1.8-fold and 16.4-fold higher for the small intestine sample at 120 min or 180 min respectively) in comparison to the turmeric phytosome formulation.

Table 7 depicts the $P_{app}$ values after apical exposure of Caco-2 cells to the small intestine digestion samples (120 or 180 min) of the standard extract or the 2 different formulations (Turmeric phytosome or the composition as used in the methods/uses of the invention) using the theoretical concentrations of curcuminoids in the small intestine compartments at 120 min or 180 min as Capi in order to take into account not only the absorptive capacity of the cells but also resistance to the digestive process. We demonstrated from those data that the level of curcuminoids that can reach the basolateral compartment (that mimics blood circulation) after gastrointestinal digestion and absorption by Caco-2 cells during 120 min and 180 min are much higher for the composition as used in the methods/uses of the invention in comparison to the standard turmeric extract turmeric ($P_{app}$ value 2.0-fold and 1.8-fold higher for the small intestine sample at 120 min or 180 min respectively) and in comparison to the phytosome formulation ($P_{app}$ value 3.4-fold and 7.1-fold higher for the small intestine sample at 120 min or 180 min respectively).

TABLE 6

$P_{app}$ values of total curcuminoids and their metabolites after apical exposure of Caco-2 cells to the small intestine digestion samples (120 or 180 min) of the standard extract or the 2 different formulations

| | After 2 h of incubation of | |
|---|---|---|
| $P_{app}$ ($\times 10^{-8}$ cm/s) | SI digestion samples 120 min | SI digestion samples 180 min |
| Standard Turmeric powder extract | 2.42 ± 1.09 | 7.19 ± 7.70 |
| Turmeric phytosome (Thorne product with Meriva ®) | 0.59 ± 0.08 | 0.19 ± 0.06 |
| The composition as used in the methods/uses of the invention with turmeric extract, sunflower oil, quillaja extract and modified starch | 1.08 ± 0.54 (1.8) | 3.08 ± 1.03 (16.4) |

The data shows mean ± SD. The fold increase in $P_{app}$ relative to turmeric phytosome formulation is shown into brackets ( ). The $P_{app}$ values are calculated using the quantified concentrations of curcuminoids in the small intestine compartments at 120 min or 180 min as Capi.

TABLE 7

$P_{app}$ values of total curcuminoids and their metabolites after apical exposure of Caco-2 cells to the small intestine digestion samples (120 or 180 min) of the standard extract or the 2 different formulations

| | After 2 h of incubation of | |
|---|---|---|
| $P_{app}$ ($\times 10^{-9}$cm/s) | SI digestion samples 120 min | SI digestion samples 180 min |
| Standard Turmeric powder extract | 2.59 ± 0.80 | 6.90 ± 0.74 |
| Turmeric phytosome (Thorne product with Meriva ®) | 1.54 ± 0.04 | 1.79 ± 0.02 |
| the composition as used in the methods/uses of the invention with turmeric extract, sunflower oil, quillaja extract and modified starch | 5.30 ± 2.44 (2.0) [3.4] | 12.65 ± 0.36 (1.8) [7.1] |

The data shows mean ± SD. The fold increase in $P_{app}$ relative to standard extract is shown into brackets ( ). The fold increase in $P_{app}$ relative to turmeric phytosome formulation is shown in square brackets [ ]. The $P_{app}$ values are calculated using the theoretical concentrations of curcuminoids in the small intestine compartments at 120 min or 180 min as Capi.

Example 6—Test the Effect of a Composition of the Invention to Enhance the Bioavailability of Curcuminoids Through Comparative Pharmacokinetic Studies In-Vivo in Mice In view of the results obtained in the in vitro model which showed that the composition as used in the methods/uses of the invention showed better resistance to gastrointestinal digestion and better absorption through intestinal cells, it is postulated that the composition as used in the methods/uses of the invention (i.e. a composition comprising 8.6% turmeric extract (comprising more than 6% curcuminoids), 15.9% sunflower oil, 2% quillaja extract, and 73.5% modified starch), will improve the bioavailability of curcuminoids in comparison to a standard turmeric extract in mice.

Therefore, a comparative pharmacokinetic study was conducted in mice.

Adult male C57Bl/6J Rj mice from Janvier Labs (St-Berthevin, France), at 5 weeks of age at receipt, were housed collectively in standard plastic cages (n=4/cage). All animals had ad libitum access to water and standard pellet food (pellet A04; SAFE, Villemoisson-sur-Orge, France), and were maintained in a temperature—(24.0 to 26.0° C.) and humidity-(40.0 to 50.0%) controlled room on a 12-h light (07:00 AM-07:00 PM)/12-h dark cycle.

All animals were acclimatized to their new environment for one week following receipt. In order to ensure both a correct acclimatization and a standard growth curve, the global food intake and the body weight of the animals were evaluated twice per week. Following this acclimatization period, mice were habituated to receive a daily per os administration of vehicle (Carboxymethylcellulose sodium salt 1% (w/v) dissolved in distillated water at room temperature, CMC; Ref #C4888, Batch number: SLBB5612V, SIGMA ALDRICH, St Quentin Fallavier, FRANCE) for six days before the treatment. During this habituation period, the global food intake and the body weight of the animals were measured daily. These measures allowed to be sure of an optimal habituation of the animals to both the injection procedures and the manipulation by the experimenters.

During the acclimatization and habituation periods, mice were allowed ad libitum access to a preweighed quantity of fresh food pellets (pellet A04; SAFE, Villemoisson-sur-Orge, France). The remaining food was weighed the next day of measure. Using a precision scale (THB-600G, PMC Millot; precision±0.01 g), the global food intake per cage (08:40-09:20 AM) was determined by subtracting the remaining food to the preweighed quantity of food. The mean daily food intake was obtained by dividing this value by the number of days separating two measures and by the number of animals of each cage. At each body weight measurement, mice were weighed in the morning (08:40-09:20 AM).

The day prior the treatment (last day of the habituation period), 120 mice were fasted in the evening (17:40-18:20 PM). The day after, mice (n=40 per formulation) received an acute treatment by oral gavage (30 ml/kg) in the morning (08:00-09:50 AM) with a standard turmeric powder extract, the Tumeric phytosome formulation as a comparator or the composition as used in the methods/uses of the invention (i.e. a composition comprising 8.6% turmeric extract (with more than 6% curcuminoids), 15.9% sunflower oil, 2% quillaja extract, and 73.5% modified starch).

An appropriate volume of Vehicle (CMC 1% dissolved in distilled water) was added in a suitable recipient under agitation and the pH was adjusted to 5.5. An appropriate amount of pre-weighted formulation was gradually added to the vehicle under constant agitation. Once homogeneous, the pH of the obtained suspension was measured and adjusted 5.5 if needed. In order to avoid any degradation of the curcuminoids, the final suspension was systematically administered in 1 h following preparation. Doses were calculated to fed animals with 300 mg/kg of total curcuminoids (see table 8). This dosage in mice is equivalent to 21.37 mg/kg in humans and 1282 mg assuming a 60 kg human—formula from (U.S. Department of Health and Human Services, Food and Drug Administration, Center for Drug Evaluation and Research (CDER). Guidance for Industry Estimating the Maximum Safe Starting Dose in Initial Clinical Trials for Therapeutics in Adult Healthy Volunteers. 2005); Human Equivalent Dose (mg/kg)=animal dose in mg/kg×(animal weight in kg/human weight in kg)$^{0.33}$. Doses were adjusted to the body weight measured just before fasting. In order to avoid any impact of feeding and drinking behavior on intestinal absorption after oral gavage with the formulation, animals were water- and food-deprived during the first 12 h following the treatment.

TABLE 8

Curcuminoids content of the standard turmeric extract and the 2 formulations and the respective concentration of the suspension used for product administration to mice at 300 mg/kg body weight of curcuminoids in the first in vivo study

| Formulation | Curcuminoids content (g/100 g) | C. ° of dosing solution (mg of formulation/ml) |
|---|---|---|
| Standard Turmeric powder extract (95% curcuminoids) | 96.18 | 10.40 |
| Turmeric phytosome (Thorne product with Meriva ®) | 16.40 | 60.98 |
| The composition as used in the methods/uses of the invention with turmeric extract, sunflower oil, quillaja extract and modified starch | 6.345 | 157.60 |

Blood was sampled at 0.5-, 1 h-, 2 h-, 4 h-, 6 h-, 8 h-, 12 h- or 24 h-post-dosing by cardiac puncture on anaesthetized mice (n=5/time point/formulation). Anesthesia was performed by intraperitoneal injection of a mixture of Ketamine/Xylazine (100 mg/kg and 15 mg/kg, respectively). For cardiac puncture, a 26 G syringe was inserted between the eighth and the tenth sternal rib, with an angle of 450 with the longitudinal axis formed by the body of the animal, in order to directly penetrate the left heart ventricle. Blood was then gently drawn to obtain a final volume of 0.6-1 ml. For the interests of the bioanalytical method, blood was thereafter transferred into an Eppendorf tube, mixed with heparin sulfate (200 U·l/ml of blood) and gently agitated. All samples were centrifuged during 15 minutes at 3000 g and 4° C. within 30 minutes after blood collection to isolate plasma. Plasma (supernatant) was aliquoted in a new 0.5 ml Eppendorf. The aliquots of plasma were frozen at −80° C. within 1 hour after centrifugation.

Plasmatic dosages of parent curcuminoids (curcumin, DMC or BDMC) and their relative metabolites (Curcumin glucuronide and sulfate, DMC glucuronide and sulfate, BDMC glucuronide and sulfate, THC, THC glucuronide and sulfate, HHC, HHC glucuronide and sulfate) were performed by a LC-MS-MS method. A calibration curve was prepared in the range 2-1000 ng/mL for each 5 curcuminoids (Phytolab, Vestenbergsgreuth, Germany) adding 54 ppb of curcumin-d6 (TLC pharmachem, Ontario, Canada) as an internal standard to ensure retention time stability and instrument correction variation. Acetonitrile was used as the diluent for each solution. For free curcuminoid determination, exactly 450 μL of internal standard solution (60 ng/mL) was loaded over 50 μL of plasma sample into Captiva 96 wells plate (ND lipids from Agilent). After mixing and filtration the eluate is ready to be injected into LC/MS system. Captiva ND Lipid plates are designed to effectively remove phospholipids from plasma. For the determination of total conjugated curcuminoid metabolites (glucuronide and sulfate metabolites), 100 μL of plasma sample was mixed with 100 μL of enzyme solution (either glucuronidase 1000 units/mL, Sigma #G7017; or sulfatase, Sigma #S9626, 100 units/ml) for 2 hours at 37° C. After this hydrolysis step, 50 μL of the solution is mixed with 450 μL of acetonitrile onto Captiva 96 wells plate as well. The sample procedure is the same than for free curcuminoids, mixing and filtering before injection.

LC/MS conditions were then as follows. The autosampler (5° C.) and LC system used was an Agilent Infinity 1290 integrated system. Agilent 6420 Triple quadrupole mass spectrometer was used during the study, with electrospray ionization. The metabolites were eluted from the BEH Shield RP 18 column (100×2.1, 1.7 μm; Waters) with a mobile phase consisting of 0.1% formic acid in water in HPLC grade (solvent A) and 0.1% formic acid in acetonitrile (solvent B), at a flow rate of 0.5 mL/min. The elution was in gradient from 40-80% B at 0-6 min. The injection volume was 2 μL for standard and samples. For each reference compound, a relevant transition of the precursor-to-product ions were detected with the utilization of the multiple reaction monitoring (MRM) mode. For each of the 5 analytes was determined in MS1 full scan tests and the product ions in MS/MS experiments. MRM transitions of each analyte were optimized using direct infusion and Optimizer B.08.00 workstation software solution (Agilent technologies, Santa Clara, CA, USA). See Table 9 for the optimal selected conditions. The mass spectrometer parameters were set as follows: ESI source both in negative and positive mode; drying gas (N2) flow rate, 10 L/min; gas temperature, 350° C.; nebulizer, 40 psi; and capillary, 4.0 kV. The MS system fully calibrated prior to running according to manufacturer's guidelines. Data analysis were carried out on Agilent MassHunter Quantitative/Qualitative analysis B.07.00 (Agilent technologies, Santa Clara, CA, USA).

For the three formulations/compositions tested, the kinetic of plasma concentration of each curcuminoid compound was determined between 0.5 and 12 h post-treatment by calculating the mean±SEM plasmatic concentration at each time point of blood collection. The pharmacokinetic parameters T1/2 (half-life), Cmax, Tmax, AUC(0-12 h) and AUC(0-∞) were determined from the 0-12 h kinetic by a non-compartmental analysis using PKSolver. PKSolver is a menu-driven add-in program for Microsoft Excel written in Visual Basic for Applications (VBA), for solving problems in pharmacokinetic (Zhang et al., 2010). The whole data are represented as mean±SEM. Statistical analyses were performed with the Statview 5.0.1 (Statview software, Cary, NC, USA) and the Excel 2013 programs. Data were analyzed by a Student's t-test at each time point. The risk a was fixed at 0.05.

TABLE 9

Retention times (Tr), multiple reaction monitoring (MRM) transitions, and optimized tandem mass spectrometry (MS/MS) detection parameters of curcuminoids, tetrahydrocurcumin and hexahydrocurcumin and internal standard.

| Compounds | Rt (min) | ISTD? | Prec. Ion Q1 Mass (Da) | Prod ions. Q3 Mass (Da) | Dwell Time (ms) | Frag (V) | CE (V) | Polarity |
|---|---|---|---|---|---|---|---|---|
| HHC | 1.07 | No | 373.2 | 179 | 200 | 118 | 12 | negative |
| THC | 2.04 | No | 371.1 | 235.1 | 200 | 100 | 10 | negative |
| | | | | 193.2 | | 100 | 21 | |
| Curcumine d6 | 3.25 | yes | 375.2 | 291.1 | 50 | 110 | 12 | positive |
| | | | | 180.1 | | 110 | 18 | |
| Curcumine | 3.29 | No | 369.1 | 285.1 | | 98 | 13 | |
| | | | | 177.1 | | 98 | 25 | |
| DMC | 3.49 | No | 339.1 | 255.1 | | 110 | 12 | |
| | | | | 177.1 | | 110 | 16 | |
| BDMC | 3.68 | No | 309.1 | 225.1 | | 110 | 12 | |
| | | | | 119.1 | | 110 | 36 | |

Figures 16, 17:
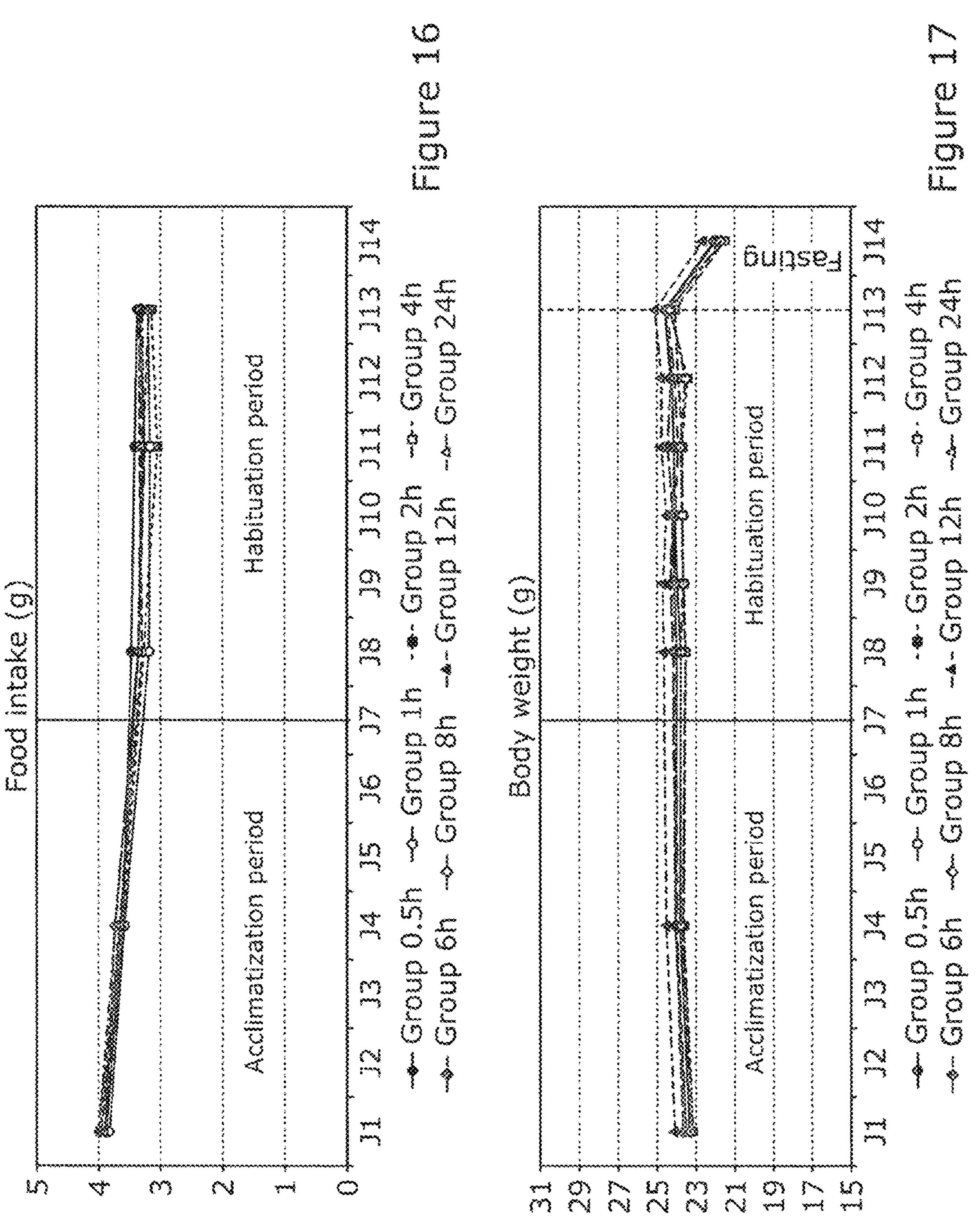
FIG. 16—Evolution of the food intake over the acclimatization and habituation periods of groups of mice sacrificed at the same time point. Mean daily food intake (g) of the different experimental groups during the acclimatization (J0-J7) and habituation (J8-J14) periods.
FIG. 17—Evolution of body weight over the acclimatization and habituation periods of groups of mice sacrificed at the same time point. Mean body weight (g) of the different experimental groups during the same periods. Data are represented as mean±SEM.

During the two successive periods of acclimatization (J1 to J7) and habituation (J8 to J14), the 24 h-food intake and the body weight of mice were regularly measured in order to ensure both a correct acclimatization and a standard growth curve before treatment. For the present study, mice were housed at four per cages, each of them being used for blood sampling at a same time point after treatment with one of the three formulations. As a consequence, the food intake and body weight data were first analyzed per group of 15 mice that have been sacrificed at a same time point (8 groups; 5 mice/time point/formulation). FIGS. 16 and 17 respectively depicts food intake and body weight of mice during the acclimatization and habituation period before treatment administration; the different groups showed classical body weight curve and food intake before treatment. It should be noted that the strong decrease in body weight observed in all groups at J15 (FIG. 17) resulted from the overnight fasting performed the night before treatment. These results confirmed that all mice used in this experiment had the same behavior and could be compared as expected.

Figure 18:
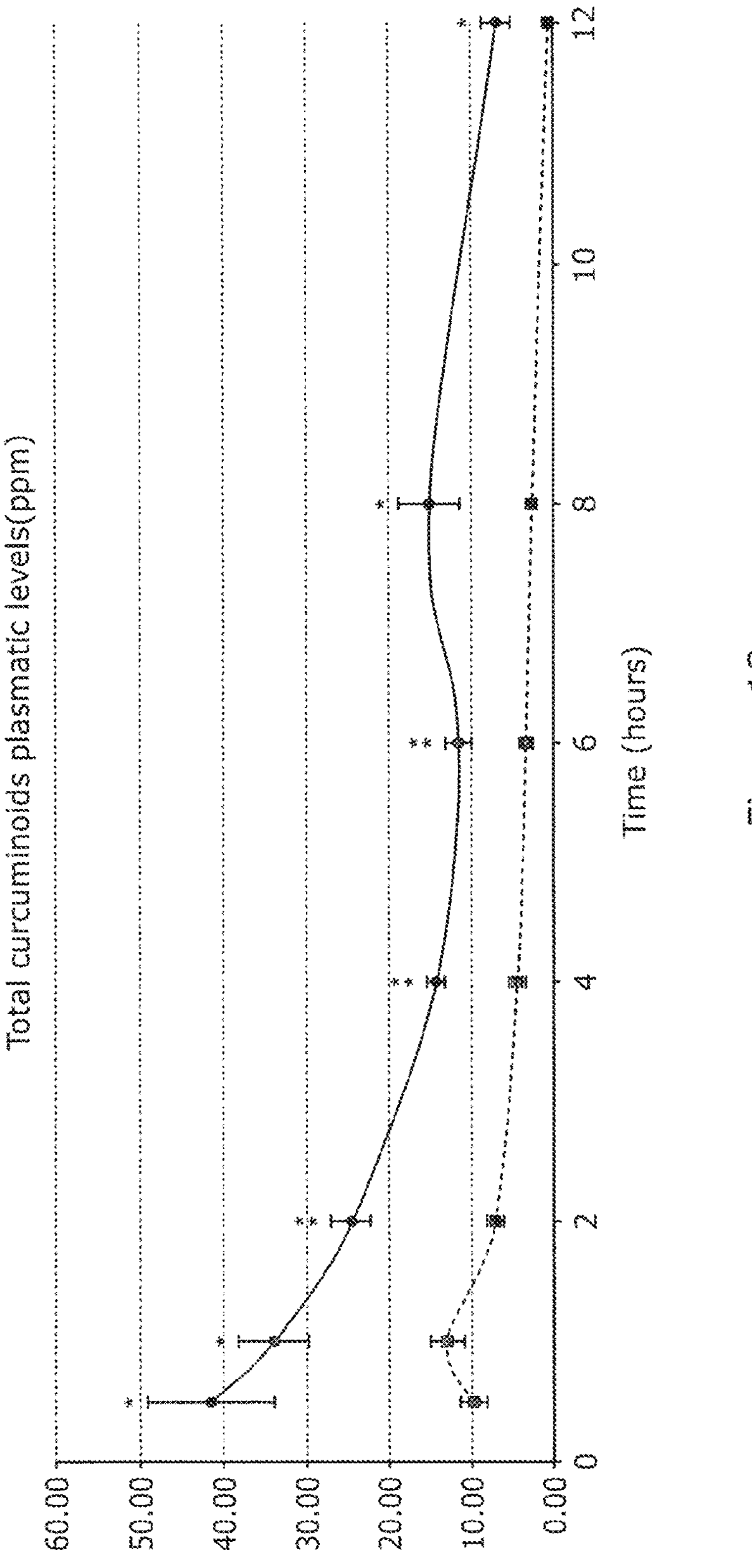
FIG. 18—Time-course of total curcuminoids levels (sum of curcumin, DMC, BDMC and their relative metabolites curcumin glucuronide and sulfate, DMC glucuronide and sulfate, BDMC glucuronide and sulfate, THC, THC glucuronide and sulfate, HHC, HHC glucuronide and sulfate) in mouse plasma after a single oral dose of Turmeric Phytosome formulation versus standard turmeric extract containing 300 mg/kg of curcuminoids. *, , *: The Turmeric Phytosome formulation significantly different (post-hoc t-test) at each time point from standard turmeric extract ($p<0.05$, $p<0.01$, $p<0.001$ respectively).

FIG. 18 depicts the pharmacokinetic profile with concentration of the total curcuminoids (sum of curcumin, DMC, BDMC and their relative metabolites curcumin glucuronide sulfate, DMC glucuronide and sulfate, BDMC glucuronide and sulfate, THC, THC glucuronide and sulfate, HHC, HHC glucuronide and sulfate) obtained at each time point in mice after oral administration (300 mg/kg bw of curcuminoids) of the Turmeric phytosome formulation and the standard extract formulation. The plasma concentration of total curcuminoids for the standard turmeric extract only reached a maximum of 12.9 ppm at 1 h and was below 10 ppm at all other time points although the turmeric phytosome formulation enabled plasma concentration of total curcuminoids to reach 41.5 ppm (μg/ml) after 30 min and was significantly superior to the one obtained for the standard at each time point except 24 h. Turmeric phystosome demonstrated a 3.2-fold increase in total curcuminoids Cmax, a 3.9-fold increase in AUC compared to standard turmeric extract. These results validated the use of the Turmeric phytosome formulation to enhance the bioavailability of curcuminoids and as a positive control and validated the relevance of our in vivo model to test the capacity of different formulations to enhance the bioavailability of curcuminoids against a standard turmeric extract.

A table containing the Mean values±SEM for each time point shown as Table 10. The numbers in brackets located next to these values indicate the number of sample which presented a positive value on the total number of samples. The result of statistical comparisons are also shown in the same table. Table 11 contains the PK parameters obtained from the non-compartmental analysis using PKSolver software. The percentage of variation between groups is also indicated (% Var°). Data are represented as mean±SEM.

| | Total curcuminoids plasmatic levels - Mean ± SEM | | |
|---|---|---|---|
| | Standard extract | Turmeric phytosome | P |
| 0.5 h | 9.71 ± 1.56 (5/5) | 41.53 ± 7.69 (5/5) | 0.0037 |
| 1 h | 12.95 ± 1.56 (5/5) | 34.00 ± 4.28 (5/5) | 0.0022 |
| 2 h | 7.10 ± 1.56 (4/4) | 24.69 ± 2.41 (5/5) | 0.0005 |
| 4 h | 4.33 ± 1.56 (4/4) | 14.31 ± 1.12 (5/5) | 0.0003 |
| 6 h | 3.22 ± 1.56 (5/5) | 11.59 ± 1.55 (5/5) | 0.0007 |
| 8 h | 2.63 ± 1.56 (5/5) | 15.03 ± 3.72 (5/5) | 0.0110 |
| 12 h | 0.55 ± 1.56 (4/4) | 6.86 ± 1.80 (5/5) | 0.0177 |
| 24 h | 1.30 ± 1.56 (4/4) | 1.44 ± 0.63 (5/5) | 0.8709 |

| | PK parameters - Total curcuminoids | | |
|---|---|---|---|
| | Standard extract | Turmeric phytosome | % Var° |
| t½ (h) | 2.688208 | 4.926631161 | 183.2682 |
| Tmax (h) | 1 | 0.5 | 50 |
| Cmax (ppm) | 12.95494767 | 41.52686492 | 320.5483 |
| AUC 0-t (ppm × h) | 49.29857342 | 193.9071934 | 393.3323 |
| AUC 0-inf (ppm × h) | 51.41308527 | 242.667998 | 471.9966 |

Tables 10 and 11: Showing the Mean values±SEM and the PK parameters obtained from the non-compartmental analysis using PKSolver software for each time point shown in FIG. 18.

Figure 19:
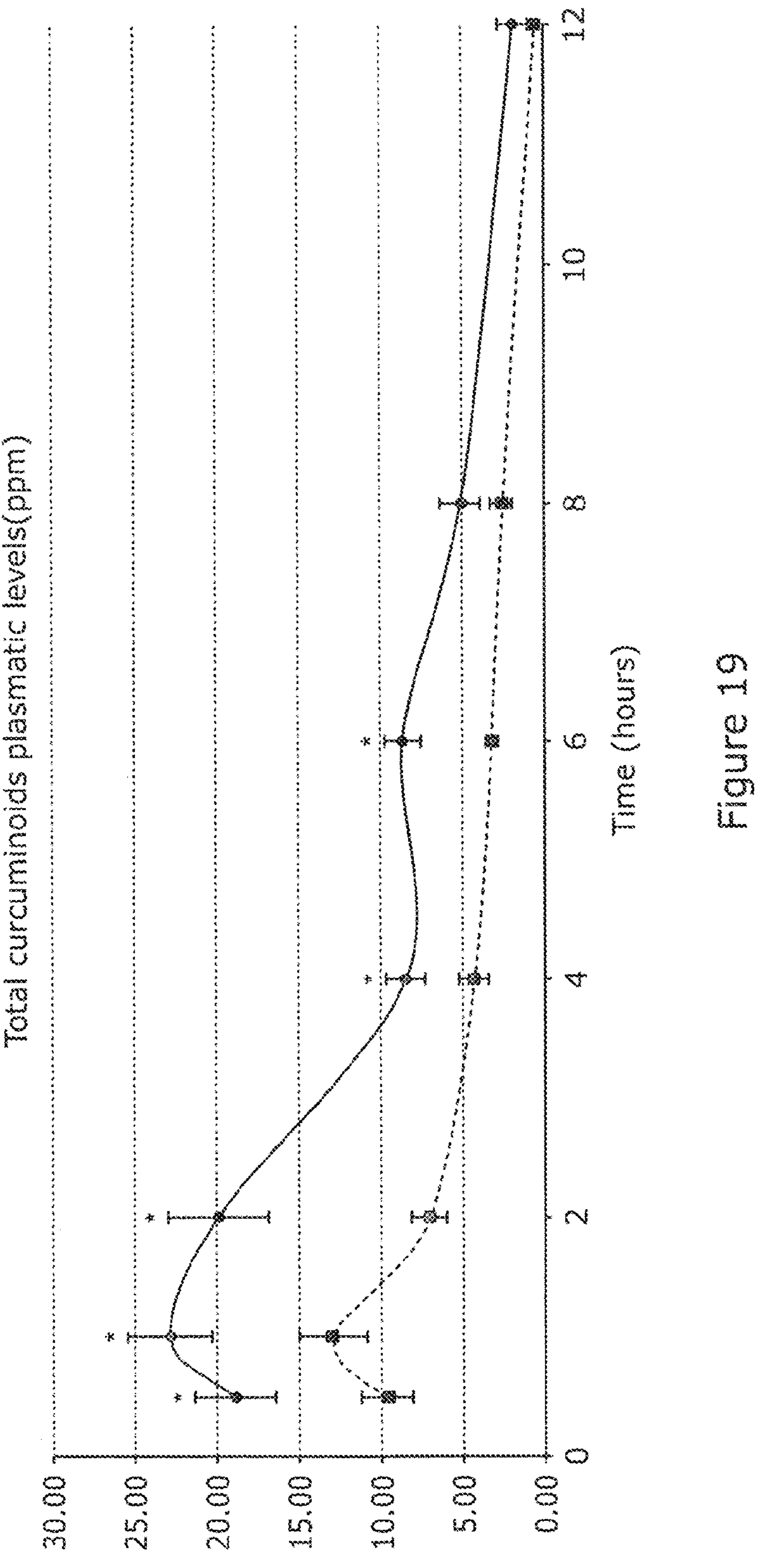
FIG. 19—Time-course of total curcuminoids levels (sum of curcumin, DMC, BDMC and their relative metabolites curcumin glucuronide and sulfate, DMC glucuronide and sulfate, BDMC glucuronide and sulfate, THC, THC glucuronide and sulfate, HHC, HHC glucuronide and sulfate) in mouse plasma after a single oral dose of the composition as used in the methods/uses of the invention versus standard turmeric extract containing 300 mg/kg of curcuminoids. *, , *: The composition as used in the methods/uses of the invention significantly different (post-hoc t-test) at each time point from standard turmeric extract ($p<0.05$, $p<0.01$, $p<0.001$ respectively).

FIG. 19 depicts the pharmacokinetic profile with concentration of the total curcuminoids (sum of curcumin, DMC, BDMC and their relative metabolites curcumin glucuronide sulfate, DMC glucuronide and sulfate, BDMC glucuronide and sulfate, THC, THC glucuronide and sulfate, HHC, HHC glucuronide and sulfate) obtained at each time pointin mice after oral administration (300 mg/kg bw of curcuminoids) of the mixture comprising curcumin, quillaja, oil and modified starch (Example 2 form 1) and the standard extract formulation. The results showed that the composition as used in the methods/uses of the invention could increase significantly total curcuminoids concentration from 0.5 h to 24 h in comparison to standard turmeric extract. The composition as used in the methods/uses of the invention demonstrated a 1.8-fold increase in total curcuminoids Cmax and a 2.2-fold increase in AUC.

A table containing the Mean values±SEM for each time point is shown as Table 12. The numbers in brackets located next to these values indicate the number of sample which presented a positive value on the total number of samples. The result of statistical comparisons are also shown in the same table. A table containing the PK parameters obtained from the non-compartmental analysis using PKSolver software is presented Table 13. The percentage of variation between groups is also indicated (% Var°). Data are represented as mean±SEM.

| | Total curcuminoids plasmatic levels - Mean ± SEM | | |
|---|---|---|---|
| | Standard extract | Test formulation | P |
| 0.5 h | 9.71 ± 1.56 (5/5) | 18.90 ± 2.45 (5/5) | 0.0133 |
| 1 h | 12.95 ± 1.56 (5/5) | 22.90 ± 2.45 (5/5) | 0.0171 |
| 2 h | 7.10 ± 1.56 (4/4) | 19.90 ± 2.45 (5/5) | 0.0093 |
| 4 h | 4.33 ± 1.56 (4/4) | 8.49 ± 2.45 (5/5) | 0.0302 |
| 6 h | 3.22 ± 1.56 (5/5) | 8.67 ± 2.45 (5/5) | 0.0012 |
| 8 h | 2.63 ± 1.56 (5/5) | 5.11 ± 2.45 (5/5) | 0.1123 |
| 12 h | 0.55 ± 1.56 (4/4) | 1.86 ± 2.45 (5/5) | 0.3241 |
| 24 h | 1.30 ± 1.56 (4/4) | 3.36 ± 2.45 (4/4) | 0.1759 |

| | PK parameters ± Total curcuminoids | | |
|---|---|---|---|
| | Standard extract | Test formulation | % Var° |
| t½ (h) | 2.688208 | 2.70737411 | 100.713 |
| Tmax (h) | 1 | 1 | 100 |
| Cmax (ppm) | 12.95494767 | 22.89919816 | 176.7603 |
| AUC 0-t (ppm × h) | 49.29857342 | 109.8465993 | 222.819 |
| AUC 0-inf (ppm × h) | 51.41308527 | 117.1097277 | 227.7819 |

Tables 12 and 13: Showing the Mean values±SEM and the PK parameters obtained from the non-compartmental analysis using PKSolver software for each time point shown in FIG. 19.

When looking at parent compounds specifically (curcumin, DMC and BDMC in their native form, i.e. unmetabolized), as shown in Table 14 that gives plasma concentration of parent curcuminoids for each time point after consumption of 300 mg/kg curcuminoids from standard turmeric extract, turmeric phytosome or the composition as used in the methods/uses of the invention, the composition as used in the methods/uses of the invention was the only one for which we were able to quantify a detectable amount of parent curcuminoids during the first 4 h post-dosing and therefore to calculate the AUC(0-12 h) and AUC(0-∞) (Table 15). A 10.9-fold increase in Cmax for parent curcuminoids were obtained for the composition as used in the methods/uses of the invention in comparison to the standard turmeric extract.

When looking at parent curcumin specifically (curcumin in its native form, i.e. unmetabolized), as shown in Table 16 that gives plasma concentration of parent curcumin for each time point after consumption of 300 mg/kg from standard turmeric extract, turmeric phytosome or the composition as used in the methods/uses of the invention, the composition as used in the methods/uses of the invention was the only one for which we were able to quantify a detectable amount of parent curcumin during the first 4 h post-dosing and therefore to calculate the AUC(0-12 h) and AUC(0-∞) (Table 16). A 521.8-fold increase in Cmax for parent curcumin was obtained for the composition as used in the methods/uses of the invention in comparison to the standard turmeric extract. Moreover, the composition as used in the methods/uses of the invention induced higher plasmatic level of parent curcumin than the turmeric phytosome formulation (1.8-fold increase in Cmax).

It can be concluded from this first in vivo experiment that the composition as used in the methods/uses of the invention with more than 6% curcuminoids, obtained with 8.6% turmeric extract, 15.9% sunflower oil, 2% quillaja extract, and 73.5% modified starch and prepared according to Form 1, is able to enhance the bioavailability of total curcuminoids and their metabolites but also the bioavailability of parent compounds in comparison to a standard turmeric extract.

It can be also concluded that the composition as used in the methods/uses of the invention could better improve the bioavailability of native curcumin than the turmeric phytosome formulation.

The composition as used in the methods/uses of the invention therefore represents an attractive way to enhance parent curcumin bioavailability without using soy-derived lecithin in the formulation as opposed to the Turmeric phytosome formulation. Also, as curcumin is considered as one of the most powerful active of turmeric in comparison to DMC and BDMC and their relative reduced, glucuronide or sulfate metabolites (Ireson C, Orr S, Jones D J, Verschoyle R, Lim C K, Luo J L, Howells L, Plummer S, Jukes R, Williams M, Steward W P, Gescher A. Characterization of metabolites of the chemopreventive agent curcumin in human and rat hepatocytes and in the rat in vivo, and evaluation of their ability to inhibit phorbol ester-induced prostaglandin E2 production. Cancer Res. 2001 Feb. 1; 61(3):1058-64; Anand P, Thomas S G, Kunnumakkara A B, Sundaram C, Harikumar K B, Sung B, Tharakan S T, Misra K, Priyadarsini I K, Rajasekharan K N, Aggarwal B B. Biological activities of curcumin and its analogues (Congeners) made by man and Mother Nature. Biochem Pharmacol. 2008 Dec. 1; 76(11):1590-611; Pal A, Sung B, Bhanu Prasad B A, Schuber P T Jr, Prasad S, Aggarwal B B, Bornmann W G. Curcumin glucuronides: assessing the proliferative activity against human cell lines. Bioorg Med Chem. 2014 Jan. 1; 22(1):435-9), the composition as used in the methods/uses of the invention represents a good solution to improve the biological efficacy of curcumin for different health conditions like joint health, inflammation, arthritis, atherosclerosis, liver steatosis, liver fibrosis, diabetes, cognition, mild cognitive impairment, irritable bowel syndrome.

TABLE 14 concentration of parent curcuminoids (sum of curcumin, DMC and BDMC) for each time point after consumption of 300 mg/kg curcuminoids from standard turmeric extract, turmeric phytosome or the composition as used in the methods/uses of the invention in the first in vivo study.

| | Parent curcuminoids plasmatic levels - Mean ± SEM | | |
|---|---|---|---|
| | Standard extract | Turmeric phytosome | The composition as used in the methods/uses of the invention |
| 0.5 h | 13.91 ± 10.05 (4/5) | 13.91 ± 10.05 (4/5) | 151.20 ± 96.93 (5/5) |
| 1 h | 0.00 ± 0.00 (0/5) | 0.00 ± 0.00 (0/5) | 6.95 ± 6.95 (1/5) |
| 2 h | 0.00 ± 0.00 (0/5) | 0.00 ± 0.00 (0/5) | 0.30 ± 0.30 (1/5) |

TABLE 14-continued concentration of parent curcuminoids (sum of curcumin, DMC and BDMC) for each time point after consumption of 300 mg/kg curcuminoids from standard turmeric extract, turmeric phytosome or the composition as used in the methods/uses of the invention in the first in vivo study.

| | Parent curcuminoids plasmatic levels - Mean ± SEM | | | | | |
|---|---|---|---|---|---|---|
| | Standard extract | | Turmeric phytosome | | The composition as used in the methods/uses of the invention | |
| 4 h | 0.00 ± 0.00 | (0/5) | 0.00 ± 0.00 | (0/5) | 2.55 ± 2.55 | (1/5) |
| 6 h | 0.00 ± 0.00 | (0/5) | 0.00 ± 0.00 | (0/5) | 0.00 ± 0.00 | (0/5) |

The numbers in brackets located next to these values indicate the number of sample which presented a positive value on the total number of samples

TABLE 15

PK parameters obtained from the non-compartmental analysis using PKSolver software for parent curcuminoids after consumption of 300 mg/kg curcuminoids from standard turmeric extract, turmeric phytosome or the composition as used in the methods/uses of the invention in the first in vivo study

| | PK parameters-parent curcuminoids | | |
|---|---|---|---|
| | Standard extract | Turmeric phytosome | The composition as used in the methods/uses of the invention |
| t½ (h) | / | / | 0.75 |
| Tmax (h) | 0.5 | 0.5 | 0.5 |
| Cmax (ppb) | 13.9 | 168.3 | 151.2 |
| AUC 0-t (ppb × h) | / | / | 83.8 |
| AUC 0-inf (ppb × h) | / | / | 86.5 |

TABLE 16 concentration of parent curcumin for each time point after consumption of 300 mg/kg curcuminoids from standard turmeric extract, turmeric phytosome or the composition as used in the methods/uses of the invention in the first in vivo study.

| | Parent curcumin plasmatic levels-Mean ± SEM | | | | | |
|---|---|---|---|---|---|---|
| | Standard extract | | Turmeric phytosome | | the composition as used in the methods/uses of the invention | |
| 0.5 h | 0.20 ± 0.20 | (1/5) | 59.30 ± 35.26 | (4/5) | 104.37 ± 64.37 | (5/5) |
| 1 h | 0.00 ± 0.00 | (0/5) | 0.00 ± 0.00 | (0/5) | 5.83 ± 5.83 | (1/5) |
| 2 h | 0.00 ± 0.00 | (0/5) | 0.00 ± 0.00 | (0/5) | 0.30 ± 0.30 | (1/5) |
| 4 h | 0.00 ± 0.00 | (0/5) | 0.00 ± 0.00 | (0/5) | 2.55 ± 2.55 | (1/5) |
| 6 h | 0.00 ± 0.00 | (0/5) | 0.00 ± 0.00 | (0/5) | 0.00 ± 0.00 | (0/5) |

The numbers in brackets located next to these values indicate the number of sample which presented a positive value on the total number of samples

TABLE 17

PK parameters obtained from the non-compartmental analysis using PKSolver software for parent curcumin after consumption of 300 mg/kg curcuminoids from standard turmeric extract, turmeric phytosome or the composition as used in the methods/uses of the invention in the first in vivo study

| | PK parameters-parent curcumin | | |
|---|---|---|---|
| | Standard extract | Turmeric phytosome | The composition as used in the methods/uses of the invention |
| t½ (h) | / | / | 0.82 |
| Tmax (h) | 0.5 | 0.5 | 0.5 |
| Cmax (ppb) | 0.2 | 59.3 | 104.4 |
| AUC 0-t (ppb × h) | / | / | 59.6 |
| AUC 0-inf (ppb × h) / | / | / | 62.6 |

Given the results obtained in the first in vivo study in mice, showing better bioavailability of total curcuminoids and parents curcuminoids and curcumin, we decided to test an optimized formulation with an higher curcuminoids content (12% curcuminoids) prepared according Form 2 with 14.4% turmeric extract, 26.8% sunflower oil, 2% quillaja extract, and 56.8% modified starch, for its capacity to improve the bioavailability of curcuminoids in comparison to a standard turmeric extract in a second comparative pharmacokinetic study in mice.

The same methodology (mice housing, acclimatization period, habituation period, curcuminoids and their metabolites quantification using LC/MS method) was used as described earlier in this Example, but with a higher number of animals per group and time (n=12/time point/formulation) and blood was sampled at 0.25-, 0.5-, 0.75-, 1 h-, 2 h-, or 8 h-post-dosing in order to specify the kinetic profile during the earliest phase after oral consumption (300 mg/kg bw) of curcuminoids coming from a standard turmeric extract (with 79.5, 15.0 and 3.0 g/100 g of curcumin, DMC and BDMC respectively and a total of 97.5 g curcuminoids/100 g), a Turmeric phytosome formulation (with 18.6, 2.6 and 0.2 g/100 g of curcumin, DMC and BDMC respectively and a total of 21.5 g curcuminoids/100 g) or the composition as used in the methods/uses of the invention prepared according to Form 2 (with 9.8, 1.6 and 0.2 g/100 g of curcumin, DMC and BDMC respectively and a total of 11.6 g curcuminoids/100 g).

Figure 20:
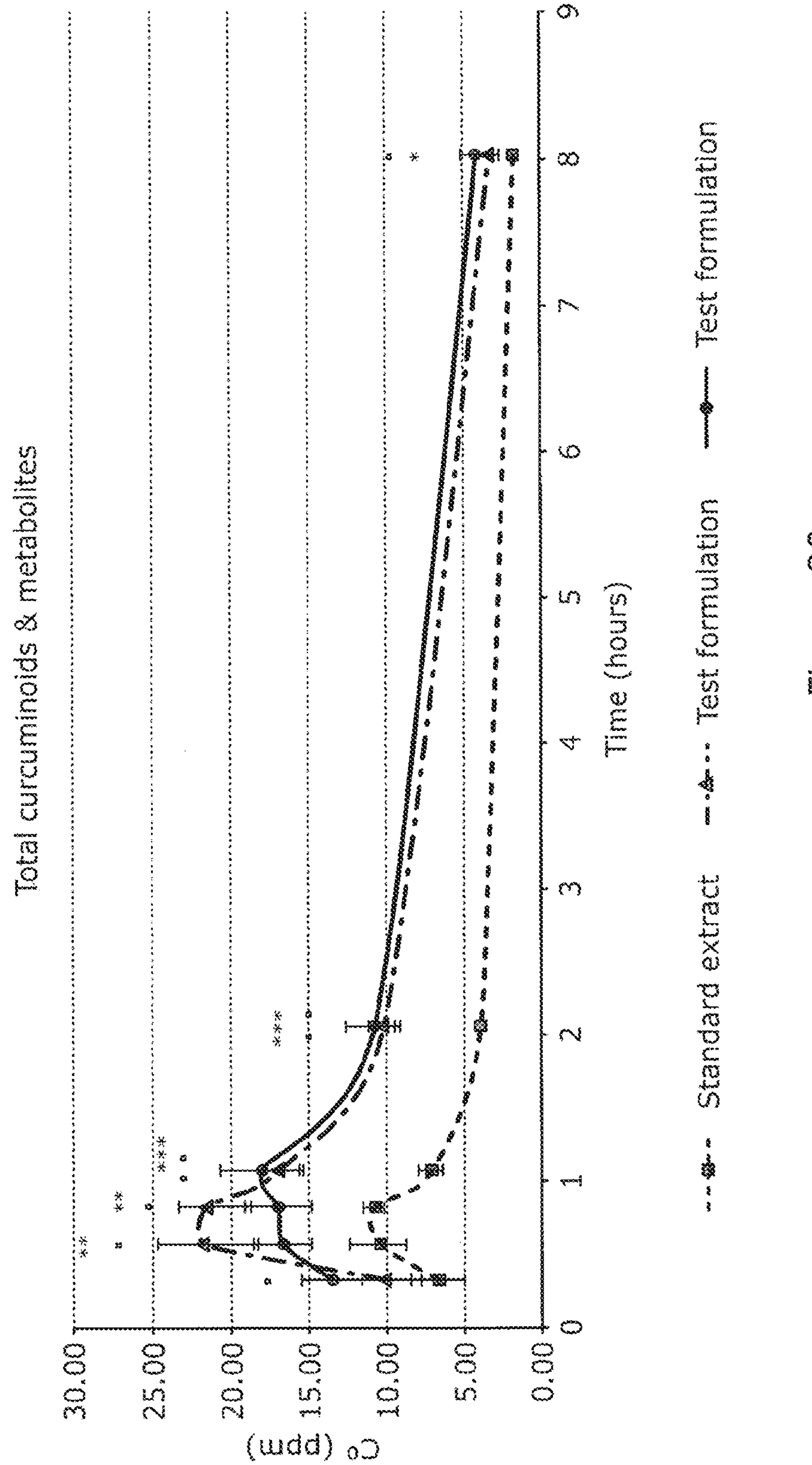
FIG. 20: Total curcuminoids and metabolites (sum of curcumin, DMC, BDMC and their relative metabolites curcumin glucuronide and sulfate, DMC glucuronide and sulfate, BDMC glucuronide and sulfate, THC, THC glucuronide and sulfate, HHC, HHC glucuronide and sulfate) concentration (ppm) as a function of time (h) after consumption of the different formulations (n=72 per formulation). □, □□: Turmeric Phytosome significantly different from standard turmeric extract ($p<0.05$, $p<0.01$ respectively); *, , *: The composition as used in the methods/uses of the invention significantly different from standard turmeric extract ($p<0.05$, $p<0.01$, $p<0.001$ respectively).

FIG. 20 depicts total curcuminoids and metabolites concentration as a function of time after consumption of the different formulations (n=72 per formulation). The results clearly showed a significant increase of curcuminoids and metabolites concentration for the Turmeric phytosome and the composition as used in the methods/uses of the invention in comparison to the standard turmeric extract. The total curcuminoids concentration was higher 0.5 h and 0.75 h after consumption of the composition as used in the methods/uses of the invention in comparison to the Turmeric phytosome formulation, showing surprisingly the better performance of the composition as used in the methods/uses of the invention in comparison to the Turmeric phytosome formulation in terms of improvement of total curcuminoids and metabolites bioavailability.

Figure 21:
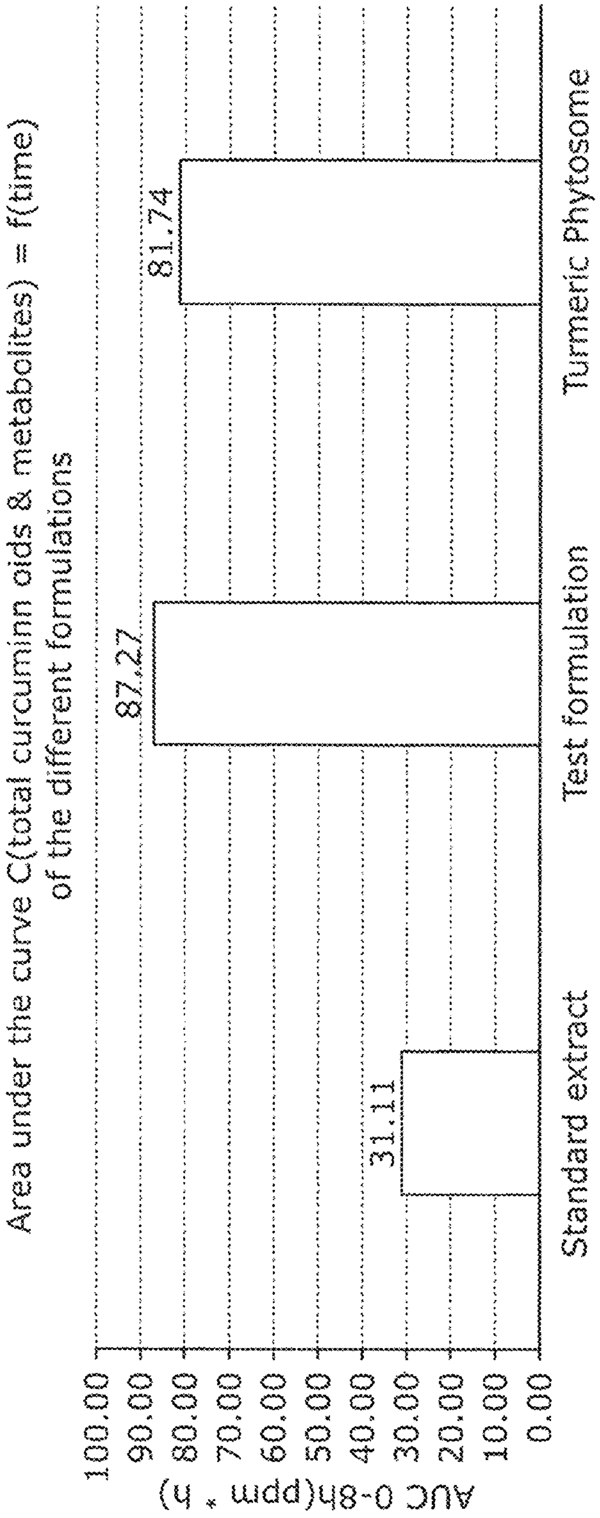
FIG. 21—Corresponding area under the curve AUC(0-8 h) of the different formulations.
Figure 22:
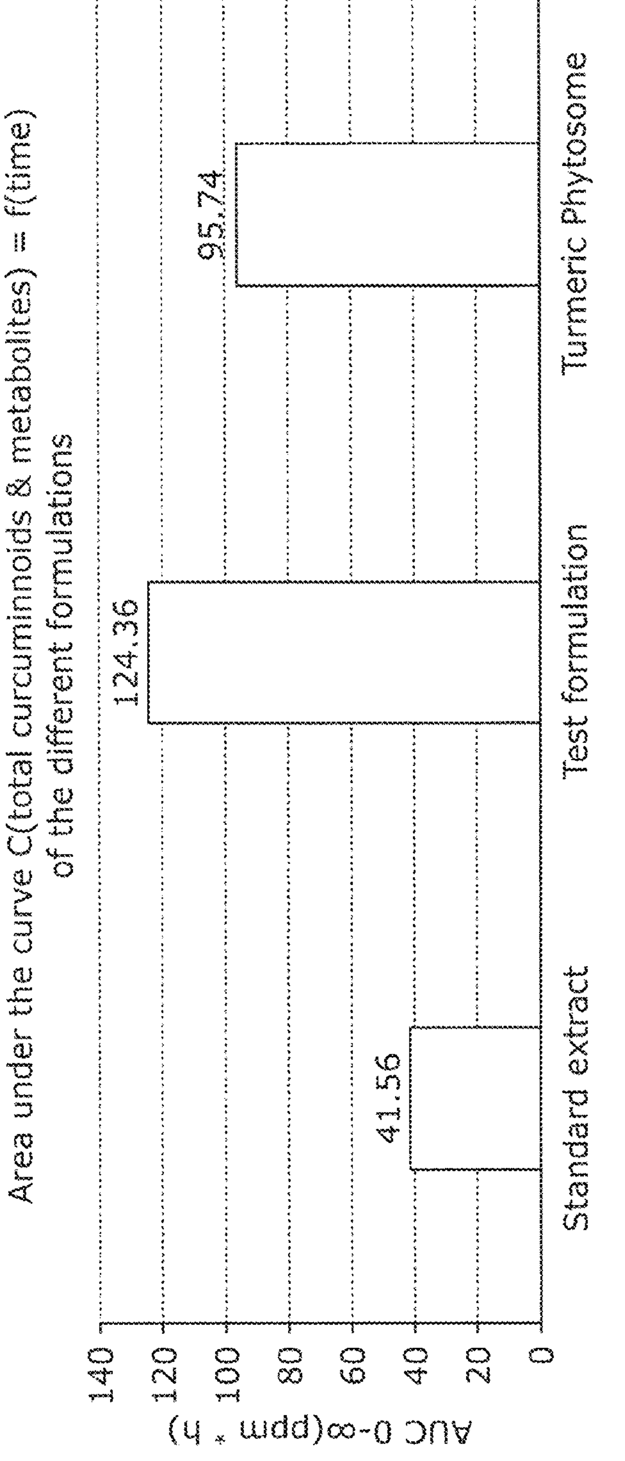
FIG. 22—Corresponding area under the curve AUC(0-∞) of the different formulations.
Figure 23:
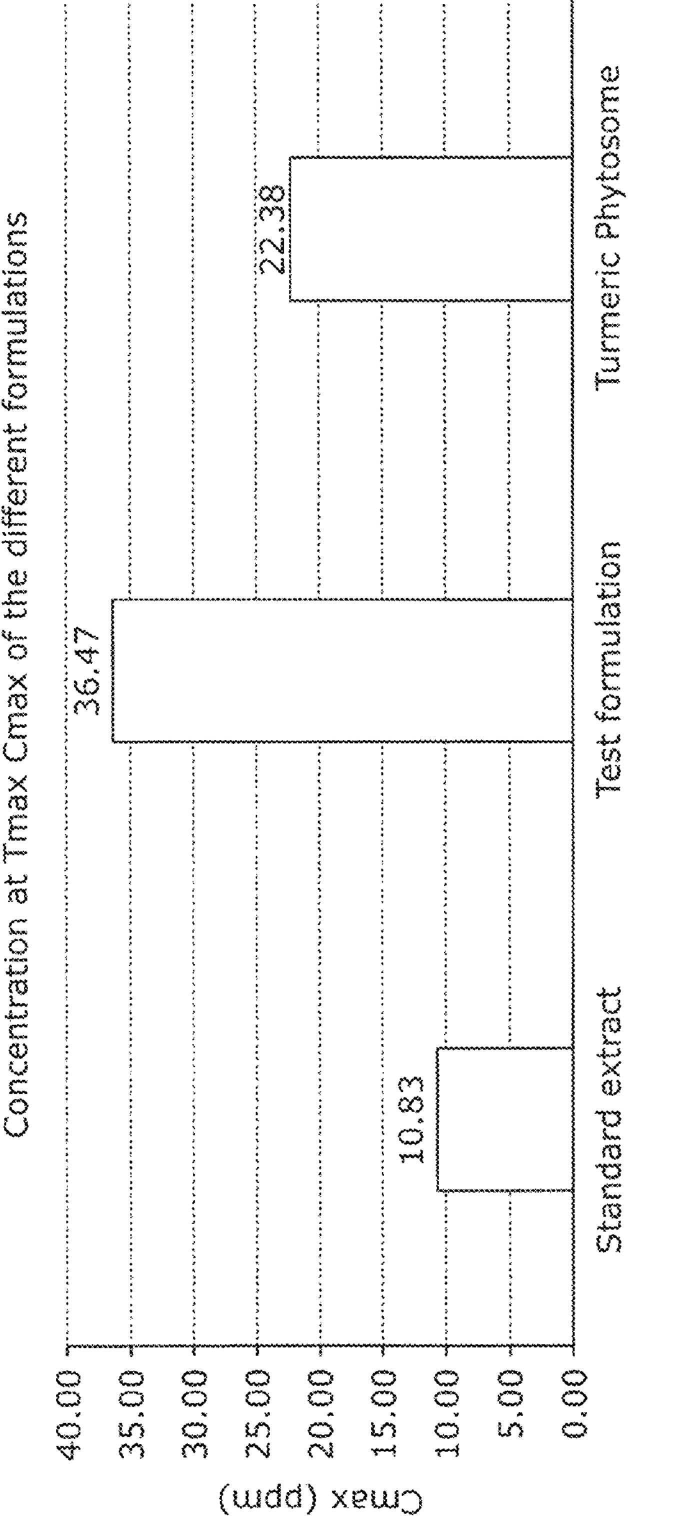
FIG. 23—Cmax (concentration at Tmax) of the different formulations.
Figure 24:
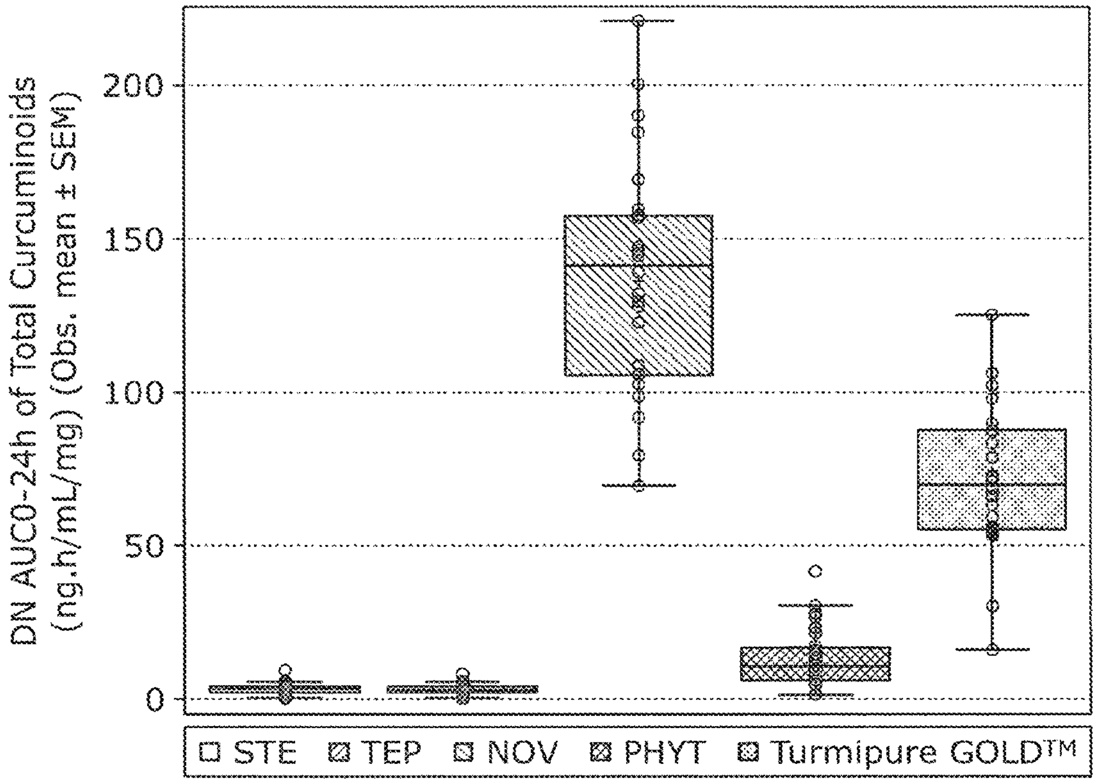
FIG. 24—Graphical representation of Dose-normalized of $AUC_{0-24h}$ for the ITT population.
Figure 25:
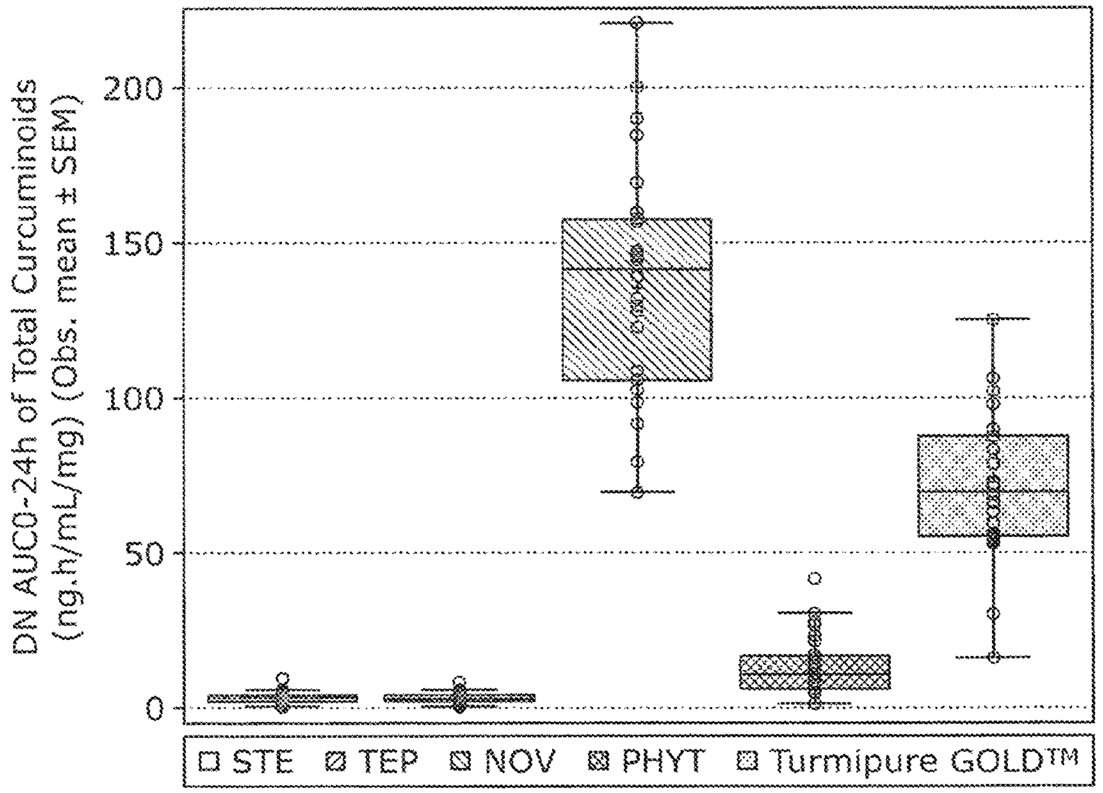
FIG. 25—Graphical representation of Dose-normalized of $AUC_{0-8h}$ for the ITT population.
Figure 26:
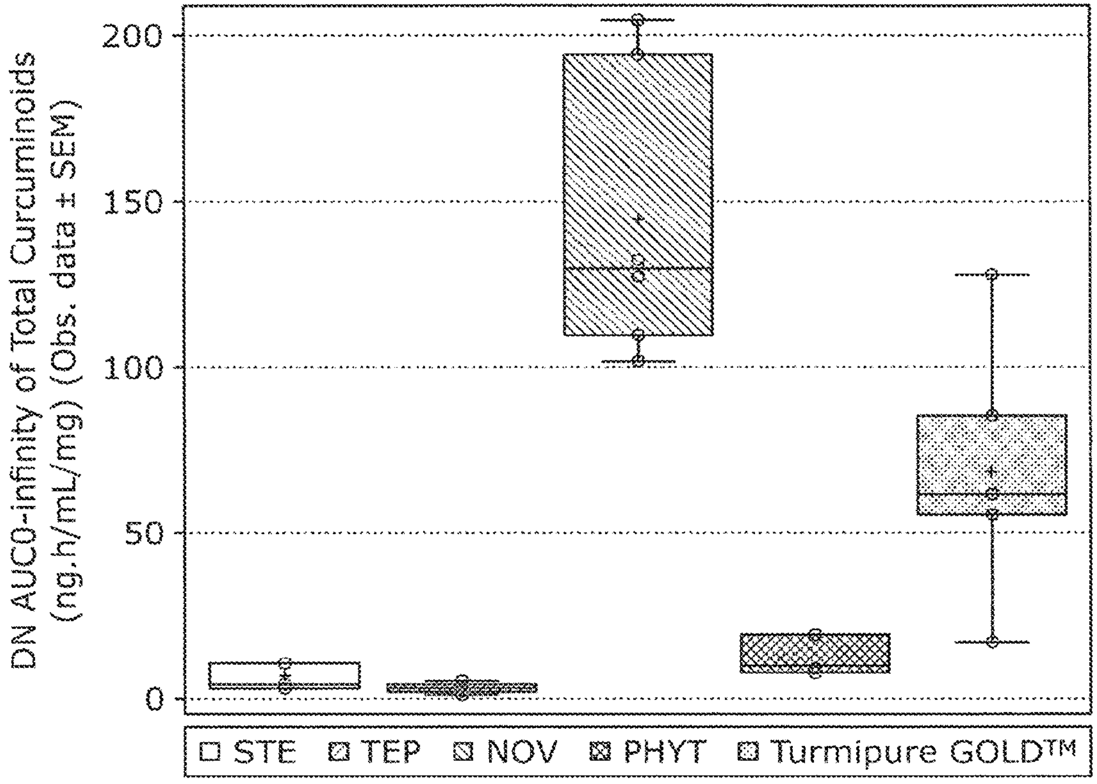
FIG. 26—Graphical representation of Dose-normalized of $AUC_{0-\infty}$ for the ITT population.
Figure 27:
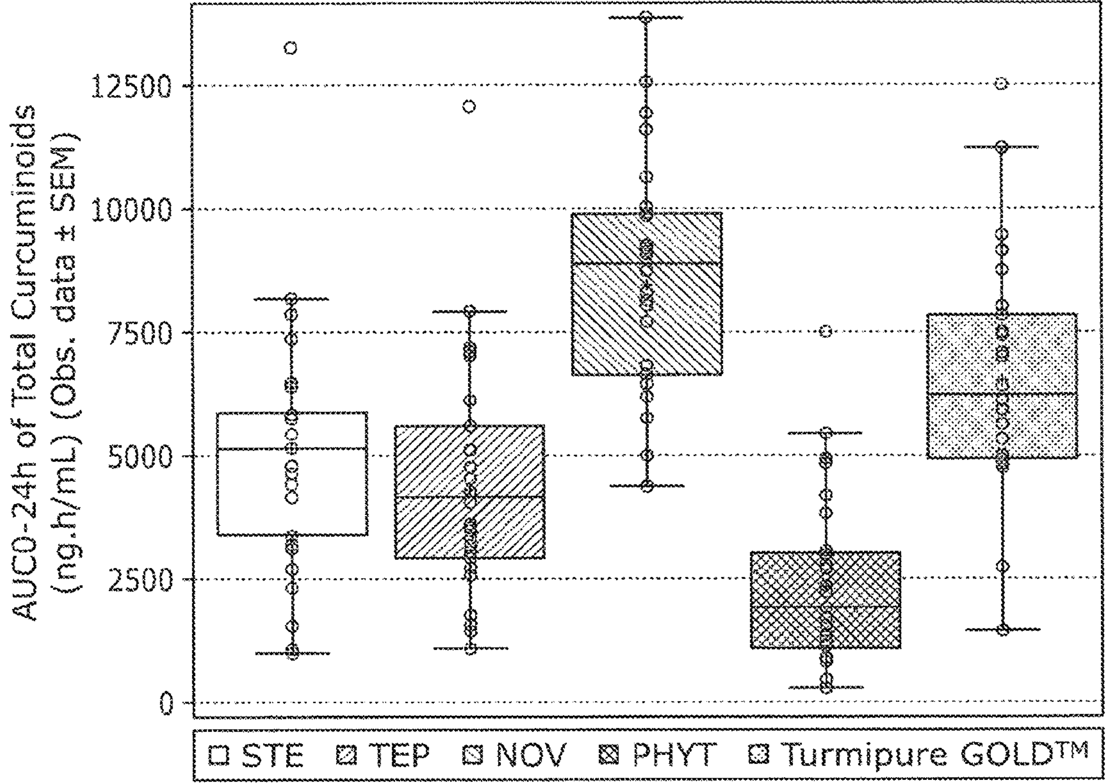
FIG. 27—Graphical representation of $AUC_{0-24}$ h for the ITT population.
Figure 28:
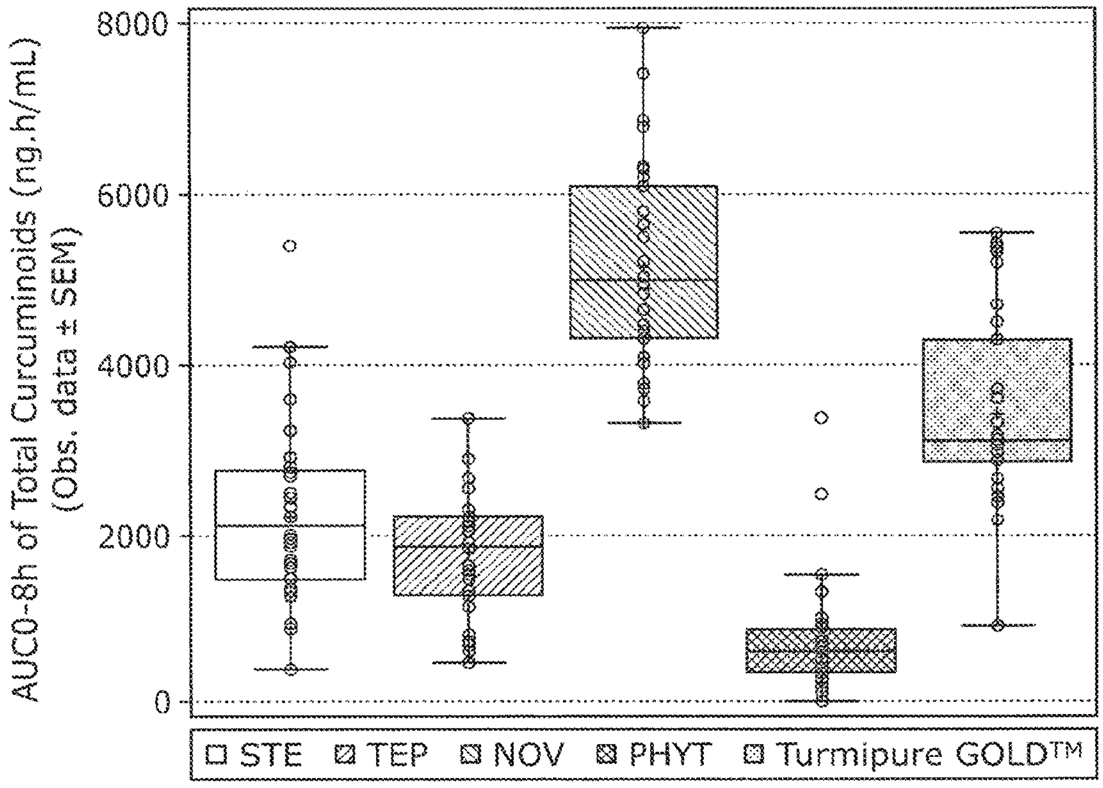
FIG. 28—Graphical representation of $AUC_{0-8h}$ for the ITT population.
Figure 29:
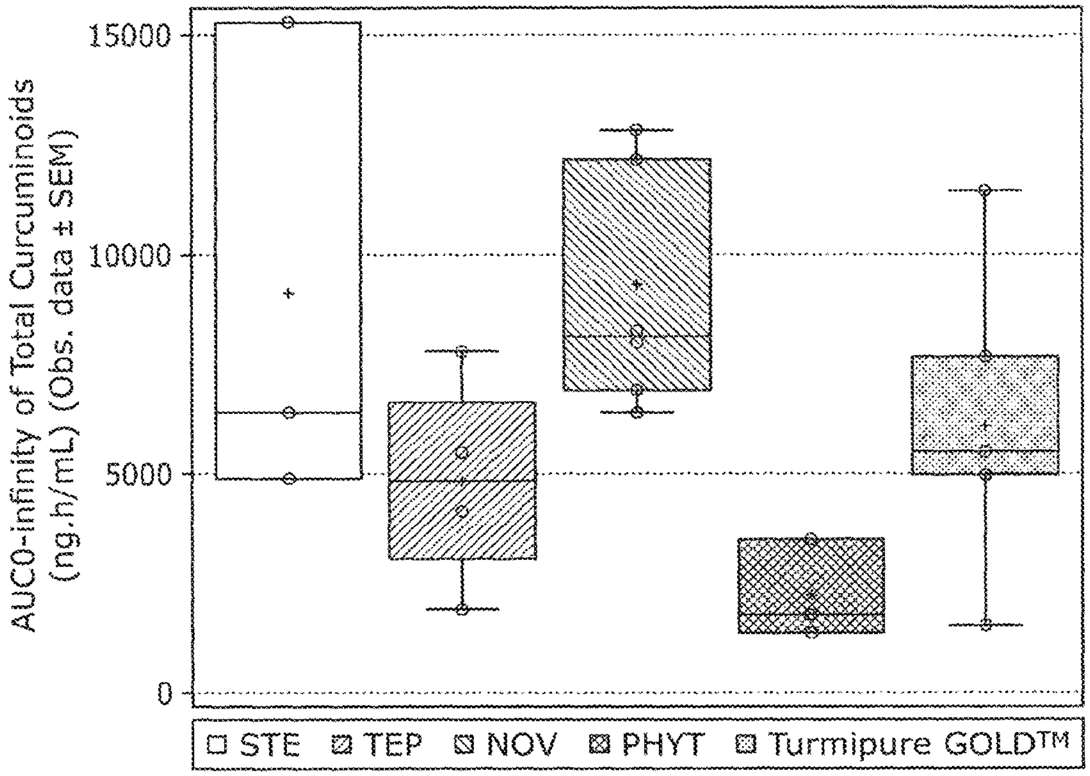
FIG. 29—Graphical representation of $AUC_{0-\infty}$ for the ITT population.
Figure 30:
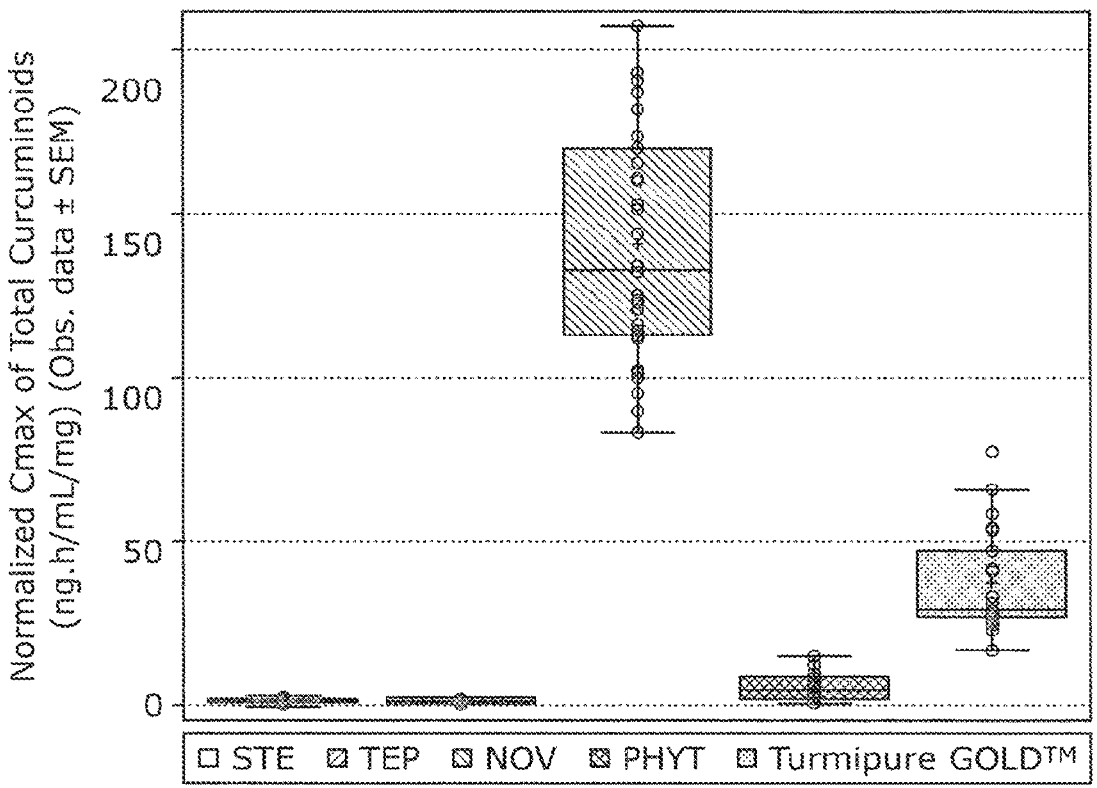
FIG. 30—Graphical representation of the normalised Cmax for the ITT population.
Figure 31:
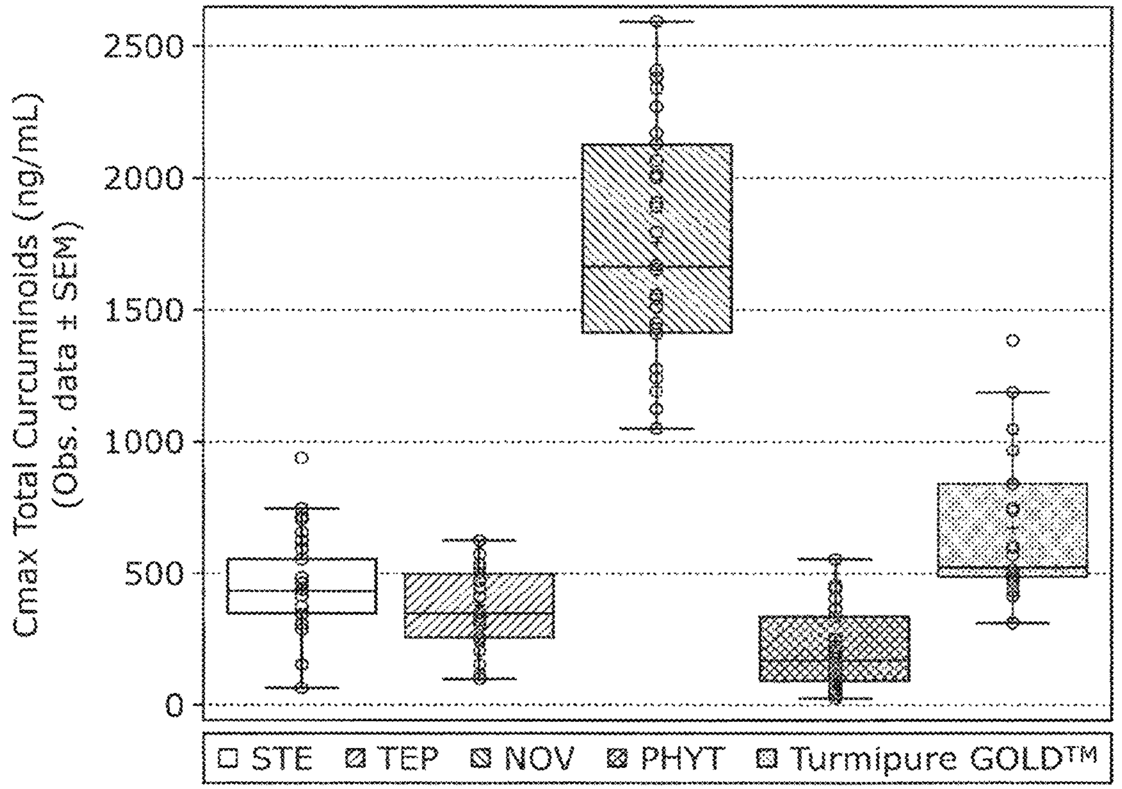
FIG. 31—Graphical representation of the Cmax for the ITT population.
Figure 32:
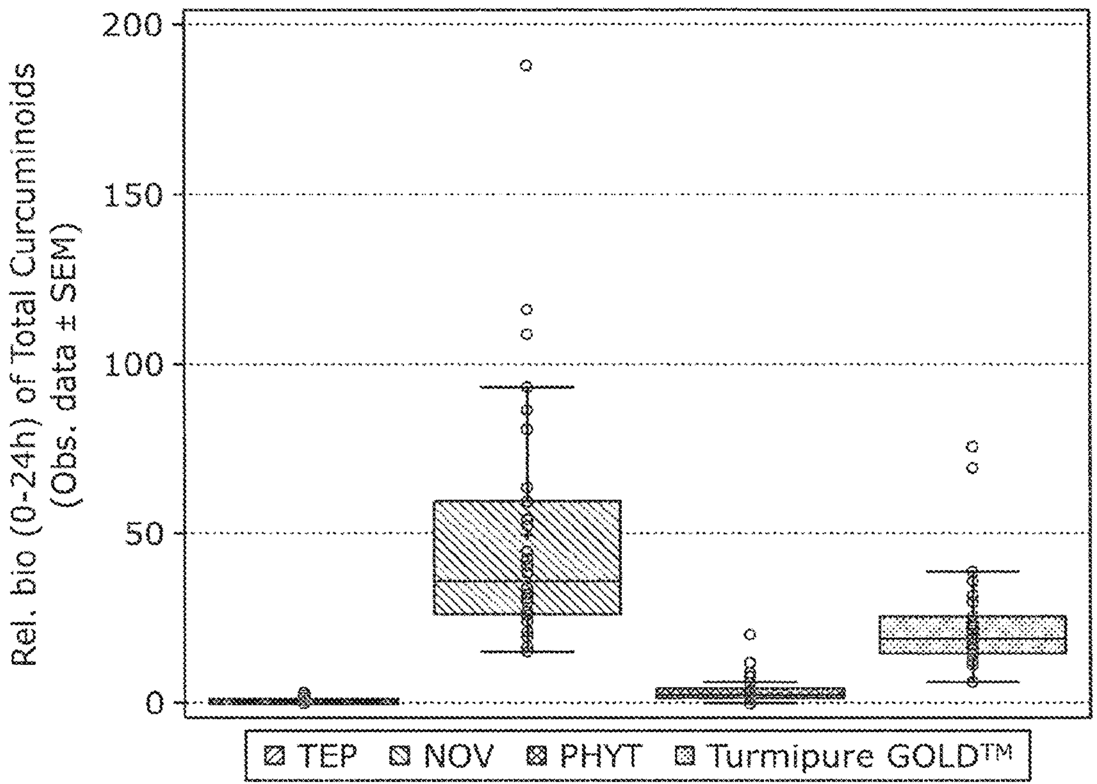
FIG. 32—Graphical representation of the relative bioavailability between 0 and 24 hours for the ITT population.
Figure 33:
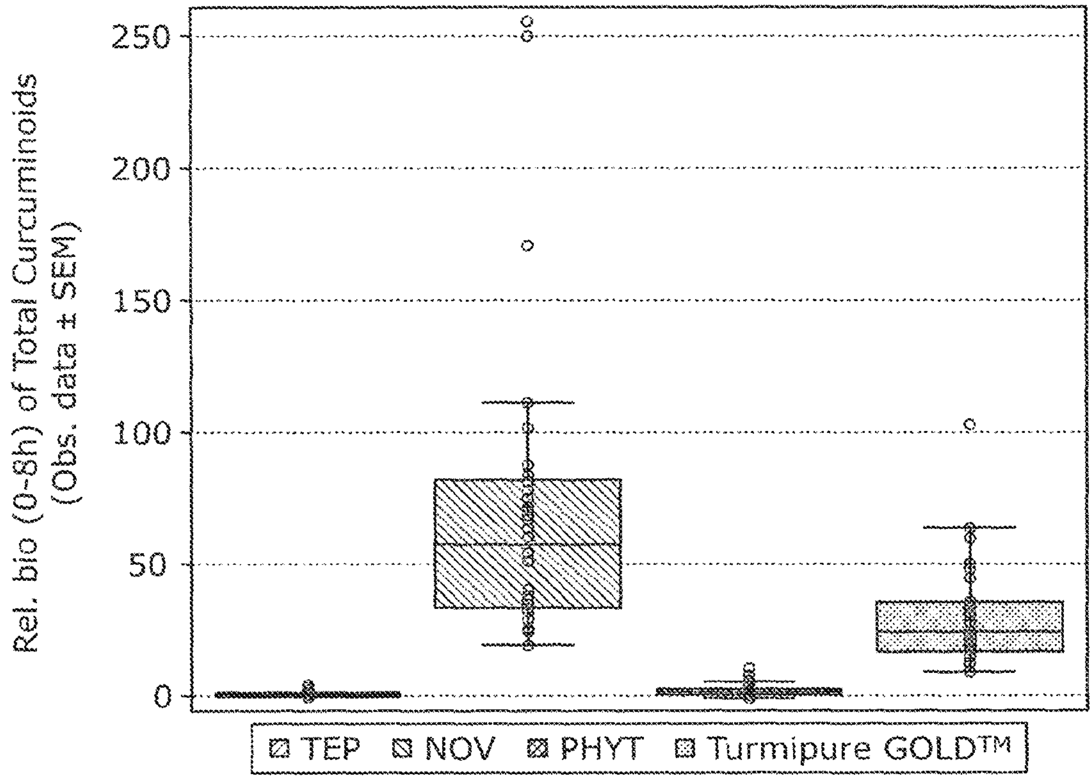
FIG. 33—Graphical representation of the relative bioavailability between 0 and 8 hours for the ITT population.
Figure 34:
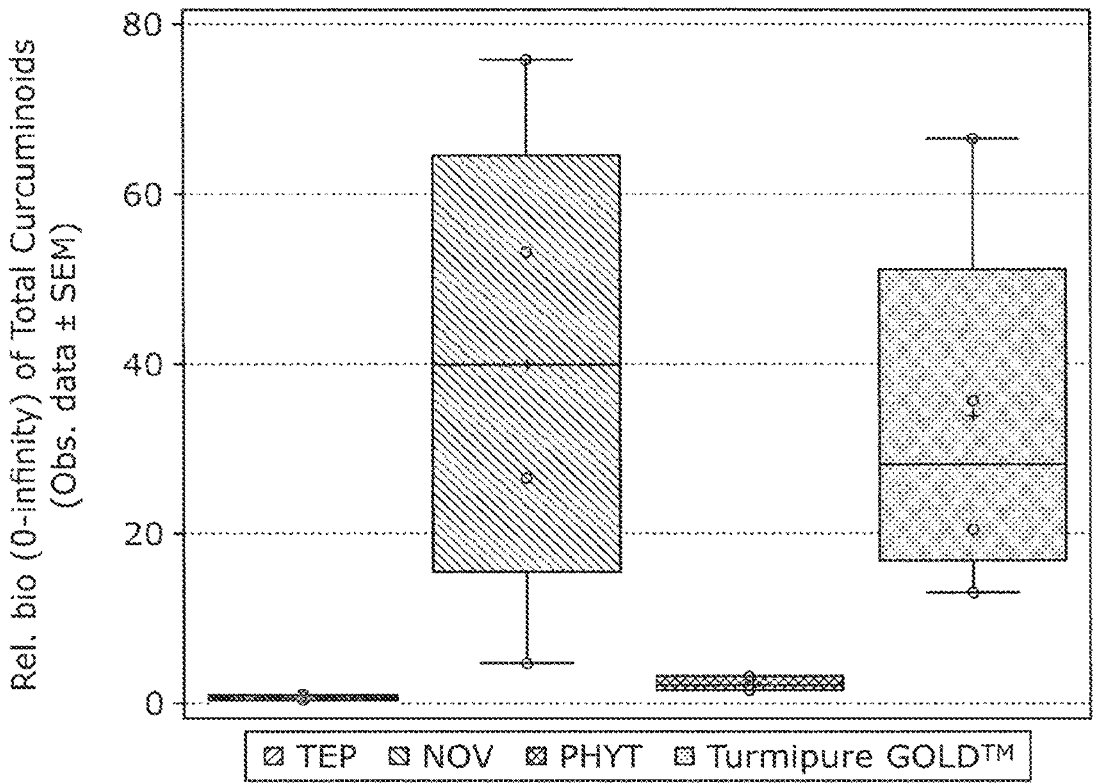
FIG. 34—Graphical representation of the relative bioavailability between 0 and infinity for the ITT population.
Figure 35:
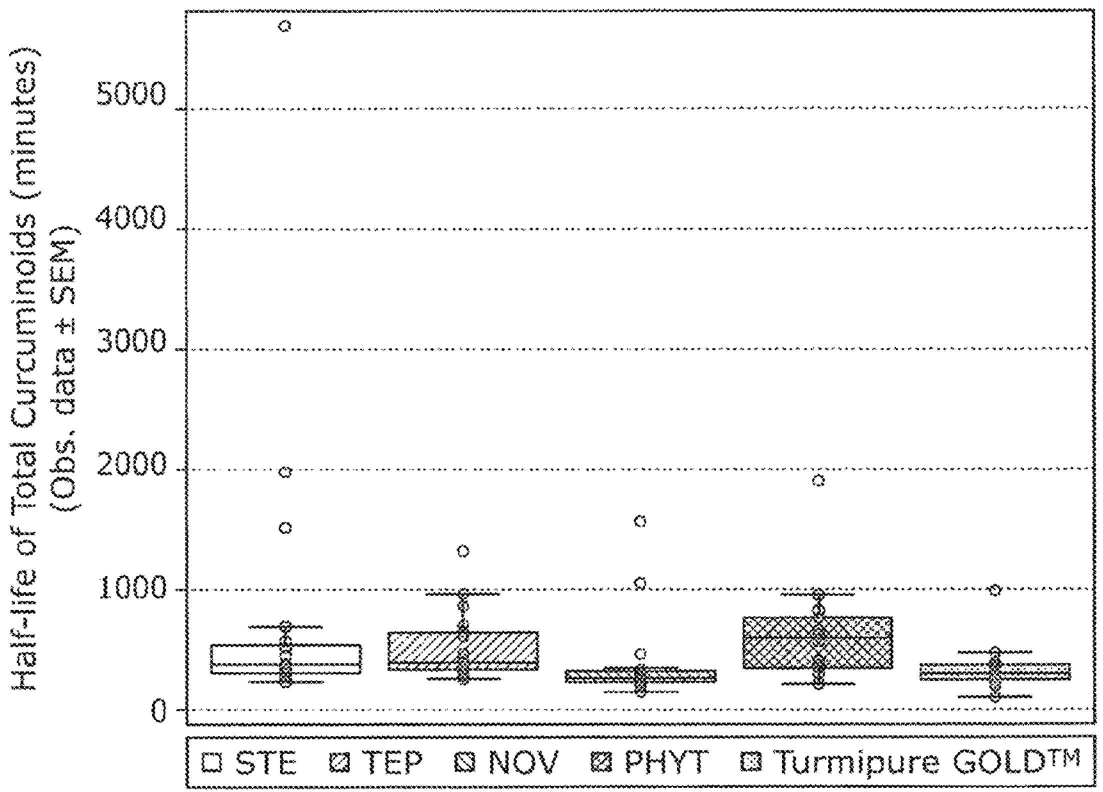
FIG. 35—Graphical representation of the half-life for the ITT population.
Figure 36:
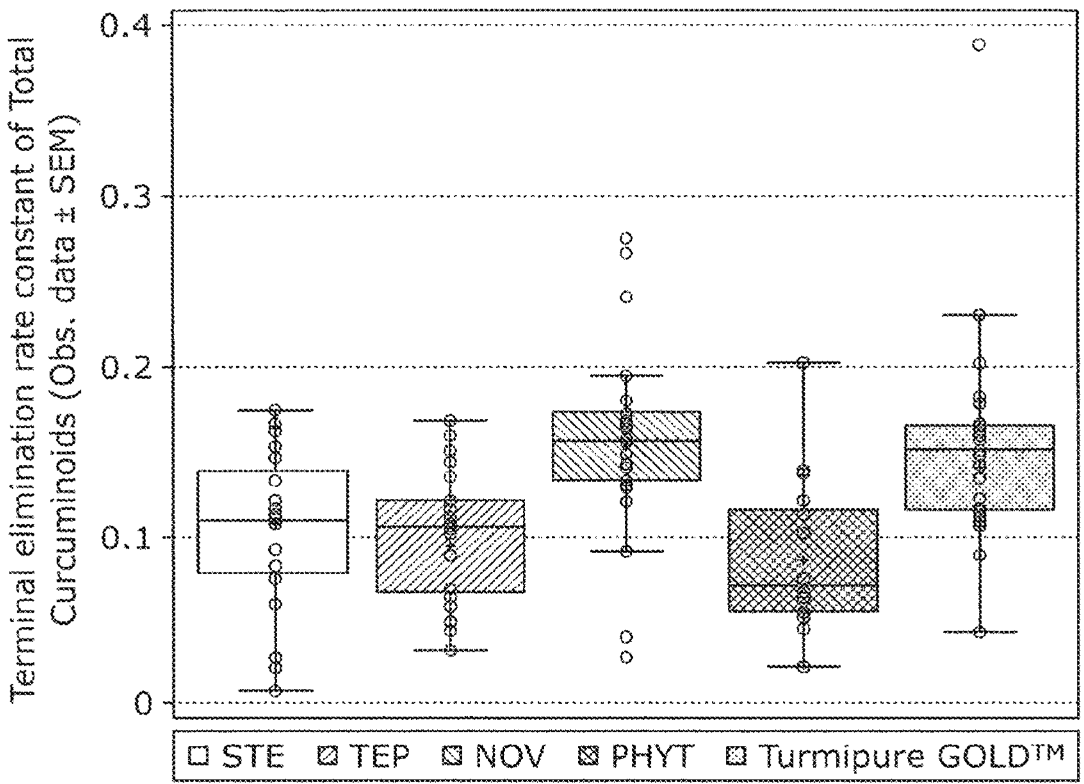
FIG. 36—Graphical representation of terminal elimination rate constant for the ITT population.
Figure 37:
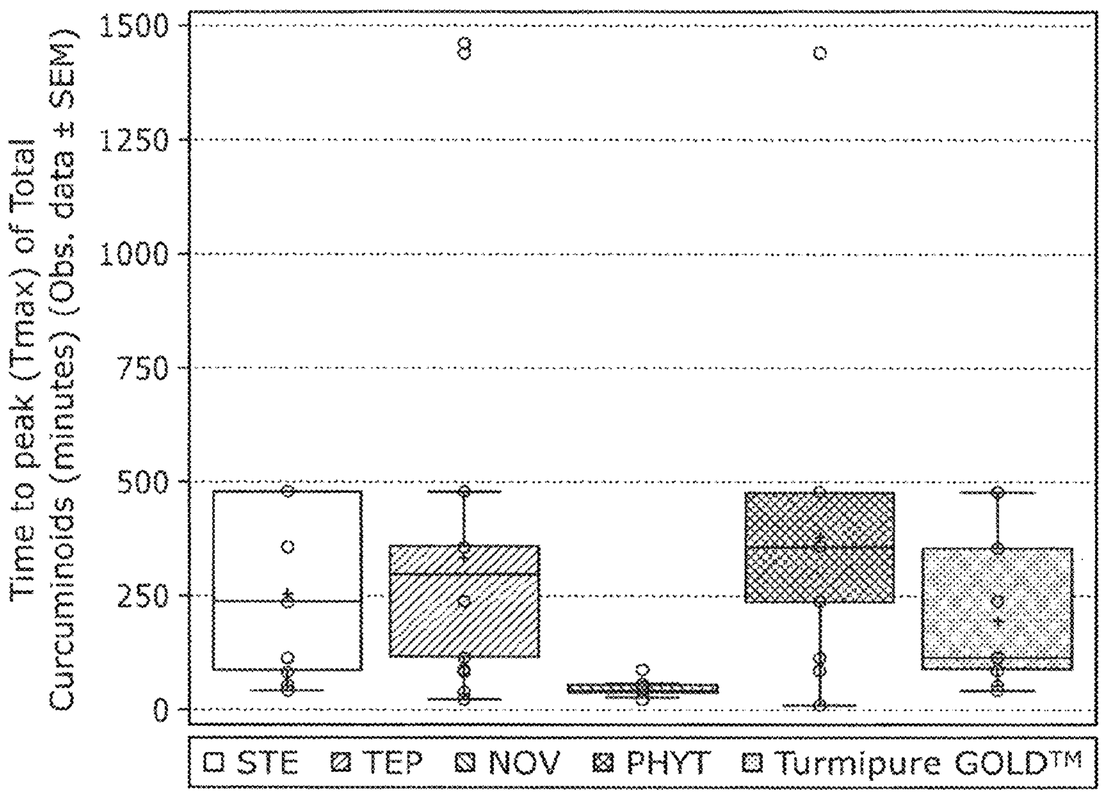
FIG. 37—Graphical representation of the Tmax for the ITT population.

This was confirmed while calculating the corresponding area under the curve AUC(0-8 h), AUC(0-∞) and Cmax (FIGS. 21, 22 and 23 respectively) that were 280% higher, 300% higher and 337% higher for the composition as used in the methods/uses of the invention in comparison to the standard extract respectively and 6.5% higher, 30% higher and 63% higher for the composition as used in the methods/uses of the invention in comparison to the Turmeric phytosome formulation respectively (Table 18). We also showed that curcuminoids and metabolites from the composition as used in the methods/uses of the invention were more rapidly absorbed with a 1.5-fold reduction in Tmax in comparison to standard extract (0.5 h versus 0.75 h) and a 2-fold reduction in Tmax in comparison to the Turmeric Phytosome formulation (0.5 h versus 1 h) respectively (Table 18). The results also showed surprisingly that curcuminoids and metabolites from the composition as used in the methods/uses of the invention were less rapidly excreted with a longer half-life (3.8 h versus 2.8 h) in comparison to the Turmeric Phytosome formulation.

When looking at parent compounds specifically (curcumin, DMC and BDMC in their native form, i.e. unmetabolized), as shown in Table 19, that gives the PK parameters of parent curcuminoids after consumption of 300 mg/kg curcuminoids from standard turmeric extract, Turmeric Phytosome or the composition as used in the methods/uses of the invention, the composition as used in the methods/uses of the invention was surprisingly the only one for which we could calculate the AUC(0-8 h) for parent curcumin. A 3.2-fold increase in Cmax for parent curcumin was obtained for the composition as used in the methods/uses of the invention in comparison to the standard turmeric extract. No Cmax could be calculated for curcumin as no parent curcumin could be found in plasma samples after consumption of the Turmeric phytosome formulation.

It can be concluded from this second in vivo experiment that the composition as used in the methods/uses of the invention with a higher curcuminoids content (12% curcuminoids) prepared according to Form 2 with 14.4% turmeric extract, 26.8% sunflower oil, 2% quillaja extract, and 56.8% modified starch is unexpectedly able to enhance the bioavailability of total curcuminoids and their metabolites but also parent curcumin in comparison to a standard turmeric extract and to the Turmeric phytosome formulation.

The composition as used in the methods/uses of the invention therefore represents an attractive way to enhance the bioavailability of curcuminoids without using soy-derived lecithin in the formulation as opposed to the Turmeric phytosome formulation.

TABLE 18

PK parameters obtained from the non-compartmental analysis using PKSolver software for total curcuminoids and metabolites after consumption of 300 mg/kg curcuminoids from standard turmeric extract, turmeric phytosome or the composition as used in the methods/uses of the invention in the second in vivo study

| | PK parameters-parent curcumin | | |
|---|---|---|---|
| | Standard extract | Turmeric phytosome | The composition as used in the methods/uses of the invention |
| t½ (h) | 3.98 | 2.76 | 3.8 |
| Tmax (h) | 0.75 | 1 | 0.5 |
| Cmax (ppb) | 10.83 | 22.38 | 36.47 (3.4) [1.6] |
| AUC 0-t (ppbm × h) | 31.11 | 81.74 (2.6) | 87.27 (2.8) [1.1] |
| AUC 0-inf (ppb × h) | 41.56 | 95.74 (2.3) | 124.36 (3.0) [1.3] |

The fold increase in AUC or Cmax relative to standard extract is shown into brackets ( ). The fold increase in AUC or Cmax relative to turmeric phytosome formulation is shown in square brackets [ ].

TABLE 19

PK parameters obtained from the non-compartmental analysis using PKSolver software for parent curcuminoids after consumption of 300mg/kg curcuminoids from standard turmeric extract, turmeric phytosome or the composition as used in the methods/uses of the invention in the second in vivo study.

| Standard extract | | Parent compounds (ppb) | | | Total parent |
|---|---|---|---|---|---|
| PK Parameter | Unity | curcumin | DMC | BDMC | compounds (ppb) |
| t½ | h | Missing | Missing | Missing | Missing |
| Tmax | h | 0.25 | 0.25 | 0.25 | 0.25 |
| Cmax | ppb | 5.55 | 25.03 | 64.43 | 114.65 |
| AUC 0-t | ppb * h | Missing | Missing | 16.82 | 29.37 |
| AUC 0-inf_obs | ppb * h | Missing | Missing | Missing | Missing |
| **Turmeric Phytosome** | | **Parent compounds (ppb)** | | | **Total parent** |
| PK Parameter | Unity | curcumin | DMC | BDMC | compounds (ppb) |
| t½ | h | Missing | Missing | Missing | Missing |
| Tmax | h | Missing | Missing | Missing | Missing |
| Cmax | ppb | Missing | Missing | Missing | Missing |
| AUC 0-t | ppb * h | Missing | Missing | Missing | Missing |
| AUC 0-inf_obs | ppb * h | Missing | Missing | Missing | Missing |
| **The composition as used in the methods/uses of the invention** | | **Parent compounds (ppb)** | | | **Total parent compounds** |
| PK Parameter | Unity | curcumin | DMC | BDMC | (ppb) |
| t½ | h | Missing | Missing | Missing | Missing |
| Tmax | h | 0.25 | 0.25 | 0.25 | 0.25 |
| Cmax | ppb | 17.94 | 11.13 | 6.34 | 60.45 |
| AUC 0-t | ppb * h | 10.8778375 | Missing | Missing | 32.13 |
| AUC 0-inf_obs | ppb * h | Missing | Missing | Missing | Missing |

Example 7—A Comparative Pharmacokinetic Study in Healthy Volunteers to Evaluate the Ability of a Composition of the Invention to Enhance the Bioavailability of Curcuminoids This study had two objectives:

1. Primary Objective

To assess plasmatic concentrations profile of total curcuminoids (curcumin, demethoxycurcumin (DMC), bisdemethoxycurcumin (DBMC) and their metabolites) on a 24 hours period after consumption of a single dose of 300 mg of composition of the invention (Turmipure GOLD™ 30% curcuminoids formulation) compared to 1500 mg Standard turmeric powder extract 95% curcuminoids.

2. Secondary Objectives

To assess, plasmatic concentrations profiles of the following parameters, after consumption of a single dose of five studied products containing either 1425 mg (standard turmeric powder extract 95% curcumindoids, Curcumin C3 complex California Gold Nutrition), 200 mg (Curcuma Platinum MannaVital), 90 mg (of a composition of the invention (Turmipure GOLD™ 30% curcuminoids)) or 60 mg (Curcumin Cell'Innov) of active substance:

Total curcuminoids;

Parent compounds (curcumin, DMC, BDMC) and their metabolites: curcumin, glucuronide and sulfate; DMC glucuronide and sulfate; BDMC glucuronide and sulfate; tetrahydrocurcumin (THC) native, glucuronide and sulfate; hexahydrocurcumin (HHC) native, glucuronide and sulfate.

The study was a monocentric, randomized, cross-over and open clinical trial.

The study commenced with a screening/inclusion visit (V0) followed by 5 experimental sessions (V1 to V5) during which the studied products were consumed by subjects (one different product at each session for each randomized subject). The V1 visit, took place a maximum of 3 weeks after V0, and can also constitute the randomization visit.

Each experimental session (V1 to V5) was separated by 1 week minimum and 2 weeks maximum. During each experimental session, subjects underwent kinetic blood sampling during 8 hour periods. The last kinetic blood sample was taken the day after each experimental session, 24 hours after the beginning of the kinetic. Urine collection was also performed during these visits for biobanking.

The subjects first urination was collected the morning of each experimental visit (totality of this first urination), with additional collections at 0 to 8 hours during the kinetic blood sampling on site and 8 to 24 hours when they came home. The last urine collection was brought back the day after the experimental visit (when they came back for the last blood sample, T24H, of the kinetic blood sampling).

Standard meals were provided to volunteers for diner before each experimental session and during the all duration of each kinetic (breakfast, lunch and afternoon collation).

The end of study was the day after the last experimental session V5 (V5-24H).

30 subjects were recruited for this study, according to the following main inclusion and exclusion criteria:

I1: Age between 18 and 45 years (limits included);

I2: BMI between 19 and 25 kg/m$^2$ (limits included);

I3: Weight stable, within ±3 kg in the last three months;

I4: With routine blood chemistry values within the normal range;

I5: For women: Non-menopausal with the same reliable contraception since at least 3 cycles before the beginning of the study and agreeing to keep it during the entire duration of the study (condom with spermicidal gel and estrogen/progestin combination contraception accepted) or menopausal without or with hormone replacement therapy (estrogenic replacement therapy begun from less than 3 months excluded);

I6: Non-smoking or with tobacco consumption≤5 cigarettes/day and agreeing not to smoke during all experimental session (V1 to V5);

I7: Agreeing not to consume food, drink and condiment containing curcumin, or other curcuminoids (DMC, BDMC) during the all duration of the study;

I8: Good general and mental health with in the opinion of the investigator: no clinically significant and relevant abnormalities of medical history or physical examination;

E1: Suffering from a metabolic or endocrine disorder such as diabetes, uncontrolled or controlled thyroidal trouble or other metabolic disorder;

E2: Suffering from a severe chronic disease (e.g. cancer, HIV, renal failure, ongoing hepatic or biliary disorders, chronic inflammatory digestive disease, arthritis or other chronic respiratory trouble, etc.) or gastrointestinal disorders found to be inconsistent with the conduct of the study by the investigator (e.g. celiac disease);

E3: Suffering from liver diseases;

E4: Current disease states that are contraindicated to subjects with dietary supplementation: chronic diarrhea, constipation or abdominal pain, Inflammatory bowel diseases (Crohn's disease or ulcerative colitis), Cirrhosis, chronic laxatives use . . . ;

E5: Suffering from Irritable Bowel Syndrome (IBS) diagnosed by a medical doctor and treated with chronic medication;

E6: Having medical history of current pathology which could affect the study results or expose the subject to an additional risk according to the investigator;

E7: Recent gastroenteritis or food borne illness such as confirmed food poisoning (less than 1 month);

E8: Who made a blood donation in the 3 months before the V0 visit or intending to make it within 3 months ahead;

E9: With a low venous capital not allowing to perform kinetic of blood samples according to the investigator's opinion;

E10: With a known or suspected food allergy or intolerance or hypersensitivity to any of the study products' ingredient and/or of the standard meals (gluten intolerance, celiac disease, etc.);

E11: Pregnant or lactating women or intending to become pregnant within 3 months ahead;

E12: Exhibiting alcohol or drug dependence;

E13: On any chronic drug treatment (for example anticoagulant, antihypertensive treatment, treatment thyroid, asthma treatment, anxiolytic, antidepressant, lipid-lowering treatment, corticosteroids, phlebotonic, veino-tonic, drug with impact on blood circulation . . . ) excepting oral and local contraceptives;

E14: Currently taking (and during the past 3 months) any supplementation from botanical origins;

E15: Having consumed curcumin-containing food supplements (curcumin, turmeric and curry) or foods (curcumin, turmeric, E100, and curry) defined as at least 3 times per week and for 2 weeks prior to testing;

E27: Control record (glycaemia, GGT, ASAT, ALAT, urea, creatinine and complete blood count) with clinically significant abnormality according to the investigator.

Five products, which are dietary supplements in shape of capsules, were tested as part of this study:

1. Standard Turmeric powder extract 95% curcuminoids 1500 mg consumed as capsules (4 capsules; 375 mg powder per capsule) (STE),
2. C3 Complex® 95% curcuminoids (1500 mg)+BioPerine® 95% piperine (15 mg) consumed as commercial product Curcumin C3 complex California Gold Nutrition (3 caps; 500 mg C3 complex powder+5 mg bioperine powder per capsule) (TEP),
3. Meriva® (1000 mg) consumed as commercial product Curcuma Platinum Mannavital 20% curcuminoids (2 caps; 500 mg powder per capsule) (PHYT),
4. Novasol® (1000 mg) consumed as commercial product Curcumin Cell innov 6% curcuminoids (2 caps; 500 mg liquid per capsule) (NOV),
5. A composition as defined herein comprising turmeric extract, sunflower oil, quillaja extract, and arabic gum, consumed as capsule (1 capsule; 300 mg powder per capsule) (TURMIPURE GOLD).

In order to ensure the healthy status of subjects and to check eligibility criteria, a blood sample was taken during V0 visit for control record analysis and pregnancy test for non-menopausal women (βhCG dosage).

The sample was taken after a physical examination and verification of eligibility criteria. A maximum of 10 mL was collected.

Measurement of blood pressure were performed at each visit during the physical examination with an electronic blood pressure monitor (Carescape Dinamap®V100). Heart Rate (HR, in bpm), Systolic Blood Pressure (SBP, in mmHg) and Diastolic Blood Pressure (DBP, in mmHg) were also assessed.

All subjects attended in a 12-hour fasted state.

In preparation for the V1 to V5 visits, after the clinical examination, a venous catheter was placed on elbow crease of the subject. This catheter allowed blood sampling for the kinetic without any additional pricks.

Kinetic sample lasted approximately 8 hours, with all the subjects staying at the clinical investigational center. Ten (10) blood sampling were taken according to the following schedule:

T-10 (baseline),

T15>T30>T45>T60>T90>T120>T240>T360>T480,

A margin of ±30 s was authorized for T15, 1 min for T30 and T45, 2 min for T60 and T90, ±5 min for T120 to T480.

The T0 time point corresponds to study product consumption.

The volunteer was allowed to consume his/her standard lunch about 4 hours after study product consumption (just after at T240 time-point) and standard afternoon meal about 8 hours after study product consumption. Lunch was consumed in 30 minutes maximum. Water was not permitted 1 h before and 1 h after product administration. The catheter was removed after the last time point, T480.

The volunteers were then asked to come again at the clinical investigational site, in a 12-hour fasting state, the day after the visit for the last blood sampling of the kinetic, T24H. Classic venous blood sample material was used (single prick). The biological parameters were assessed with these samplings being analyzed in plasma; thus only EDTA tubes were used (5 mL per sampling).

A calibration curve was prepared in the range 10-600 ng/mL for each 5 curcuminoids (Phytolab, Vestenbergsgreuth, Germany) adding 50 ppb of labelled curcumins (TLC pharmachem, Ontario, Canada) as an internal standard to ensure retention time stability and instrument correction variation. Acetonitrile was used as the diluent for each solution. For free curcuminoid determination, exactly 500 μL of cold methanol:aetonitrile (15:85) mixture containing internal standards solution (50 ng/mL) was loaded over 100 μL of plasma sample into Captiva 96 wells plate (EMR lipids from Agilent, see FIG. 18). After mixing and filtration the curcumins was eluted with cold water:acetonitrile (1:4) mixture and the eluate was injected into LC/MS system. Captiva EMR Lipid plates were designed to effectively remove phospholipids from plasma. For the determination of total conjugated curcuminoid metabolites (glucuronide and sulfate metabolites), 60 μL of plasma sample was mixed with 60 μL of enzyme solution (either glucuronidase at 1 mg/mL, 100 mM phosphate buffer pH 6.8 or sulfatase 10 mg/mL, 100 mM acetate buffer, pH 5.0) for 1 hours at 37° C. with constant agitation (Eppendorf, Thermomixer C, 400 rpm). After this hydrolysis step, the protocol was the same as for free curcuminoids using Captiva 96 wells plate EMR lipid.

EMR-Lipid protocol for the human plasma treatment before injection is as depicted in FIG. 38.

The LC/MS conditions were as follows. The autosampler (5° C.) and LC system was an Agilent Infinity II 1290 integrated system. Agilent 6420 Triple quadrupole mass spectrometer was used during the study, with electrospray ionization. The metabolites were eluted from the BEH C18 column (100×2.1 mm, 1.7 μm; Waters) with a mobile phase consisting of 0.1% formic acid in water in HPLC grade (solvent A) and 0.1% formic acid in acetonitrile (solvent B), at a flow rate of 0.4 mL/min and a column temperature of 35° C. The elution was in gradient from 40-60% B at 0-3 min. The injection volume was 2 μL for standard and samples. For each reference compound, a relevant transition of the precursor-to-product ions was detected with the utilization of the multiple reaction monitoring (MRM) mode. Each of the 5 analytes was determined in MS1 full scan tests and the product ions in MS/MS experiments. MRM transitions of each analyte was optimized using direct infusion and Optimizer B.08.00 workstation software solution (Agilent technologies, Santa Clara, CA, USA). See Table 20 for the optimal selected conditions. The mass spectrometer parameters was set as follows: ESI source both in negative and positive mode; drying gas (N2) flow rate, 10 L/min; gas temperature, 350° C.; nebulizer, 40 psi; and capillary, 4.0 kV. The MS system was fully calibrated prior to running according to manufacturer's guidelines. Data analysis was carried out on Agilent MassHunter Quantitative/Qualitative analysis B.07.00 (Agilent technologies, Santa Clara, CA, USA).

TABLE 20

Retention times (Tr), multiple reaction monitoring (MRM) transitions, and optimized tandem mass spectrometry (MS/MS) detection parameters of 5 curcuminoids and internal standard.

| Cpd Name | Rt (min) | ISTD ? | Prec. Ion Q1 Mass (Da) | Prod. ions Q3 Mass (Da) | Dwell time (ms) | Frag (V) | CE (V) | Polarity |
|---|---|---|---|---|---|---|---|---|
| Curcumin d6 | 3.05 | Yes | 375.2 | 180.0 | 50 | 65 | 24 | Positive |
| | | | | 177.0 | 50 | 120 | 20 | Positive |
| Curcumin | 3.05 | No | 369.1 | 145.0 | 50 | 120 | 36 | Positive |
| | | | | 117.0 | 50 | 120 | 48 | Positive |
| DMC d7 | 2.89 | Yes | 346.1 | 151.0 | 50 | 105 | 32 | Positive |
| DMC | 2.89 | No | 339.1 | 177.0 | 50 | 105 | 20 | Positive |
| | | | | 147.0 | 50 | 105 | 28 | Positive |
| | | | | 91.1 | 50 | 105 | 60 | Positive |
| BDMC d8 | 2.74 | Yes | 317.1 | 151.0 | 50 | 80 | 24 | Positive |
| BDMC | 2.74 | No | 309.1 | 147.0 | 50 | 95 | 24 | Positive |
| | | | | 119.0 | 50 | 95 | 40 | Positive |
| | | | | 91.1 | 50 | 95 | 60 | Positive |
| HHC d6 | 1.34 | Yes | 379.2 | 182.1 | 50 | 110 | 20 | Negative |
| HHC | 1.34 | No | 373.1 | 193.1 | 50 | 100 | 12 | Negative |
| | | | | 179.1 | 50 | 100 | 16 | Negative |
| | | | | 121.0 | 50 | 100 | 56 | Negative |
| THC d6 | 2.84 | Yes | 377.1 | 135.1 | 50 | 105 | 60 | Negative |
| THC | 2.84 | No | 371.1 | 235.1 | 50 | 120 | 12 | Negative |
| | | | | 193.1 | 50 | 120 | 20 | Negative |
| | | | | 135.0 | 50 | 120 | 56 | Negative |

Analysis Population

ITT population: All subjects randomized in the study having consumed at least one dose of the products (n=30)

PP population: Subjects included in the ITT population who completed the study presenting no major protocol deviations (n=30). The following subjects were excluded from the PP population:

Subject SN01-040-V5 for all parameters

SAFETY population: All subjects randomized in the study having consumed at least one dose of the products (n=30)

TABLE 21

Description of the study population at baseline showing mean and standard deviation.

| Number of subjects | Included subjects (N = 30) |
|---|---|
| Women/Men | 16 (53.3)/14 (46.7) |
| Age (years) | 33.6 (6.79) |
| Weight (kg) (V0) | 64.5 (11.09) |
| BMI ($kg/m^2$) (V0) | 22.1 (2.13) |

Software Environment

Statistical analyses were performed by Biofortis using SAS® software version 9.3 (SAS Institute Inc., Cary, NC, USA).

Significance level

For all statistical tests (two-tailed), the 0.05 level of significance was used to justify a claim of a statistically significant effect.

Methods of handling missing data for kinetics

If more than 2 values or 2 consecutive values are missing in the kinetics, the AUC calculation cannot be performed and the kinetics were considered as missing in the statistical analyses (no missing data replacement was performed);

If a data is missing at T-10 time-point, the AUC calculation cannot be performed and the kinetics were considered as missing in the statistical analyses (no missing data replacement was performed);

If a value (except the baseline value and the value at the last time-point) is missing in the kinetics, it was replaced by the value obtained using the CopyMean method developed by Genolini (Genolini, 2013);

If a value at the last time-point (T1440=T24 h) of the kinetics is missing, no missing data replacement was performed.

In case of non-complete kinetics after missing data handling, the AUC cannot be calculated.

→ This method was applied on ITT and PP populations.

Derived Variables

Total curcuminoids=Curcumin+DMC+BDMC+THC+HHC+Curcumin glucuronide+DMC glucuronide+BDMC glucuronide+THC glucuronide+HHC glucuronide+Curcumin sulfate+DMC sulfate+BDMC sulfate+THC sulfate+HHC sulfate If all of these 15 elements are missing, total curcuminoids cannot be calculated. If at least one of these 15 elements is quantified, total curcuminoids were calculated.

Total Parent compounds=sum of curcumin+DMC+BDMC

Total Parent compounds and their relative sulfate and glucuronide metabolites=Curcumin+Curcumin glucuronide+Curcumin sulfate+DMC+DMC glucuronide+DMC sulfate+BDMC+BDMC glucuronide+BDMC sulfate Curcumin and its relative sulfate and glucuronide metabolites=Curcumin+Curcumin glucuronide+Curcumin sulfate DMC and its relative sulfate and glucuronide metabolites=DMC+DMC glucuronide+DMC sulfate BDMC and its relative sulfate and glucuronide metabolites=BDMC+BDMC glucuronide+BDMC sulfate Curcumin and all its relative metabolites=Curcumin+Curcumin glucuronide+Curcumin sulfate+THC+THC glucuronide+THC sulfate+HHC+HHC glucuronide+HHC sulfate Relative bioavailability between 0 to 24 hours=Ratio of the dose-normalized AUC0-24 h for the different tested formulation to the dose-normalized AUC0-24 h obtained for the reference product (turmeric extract 95% curcuminoids)

Relative bioavailability between 0 to 8 hours=Ratio of the dose-normalized AUC0-8 h for the different tested formulation to the dose-normalized AUC0-8 h obtained for the reference product (turmeric extract 95% curcuminoids)

Relative bioavailability between 0 to infinity=Ratio of the dose-normalized AUC0-∞ for the different tested formulation to the dose-normalized AUC0-∞ obtained for the reference product (turmeric extract 95% curcuminoids)

Data Handling of Values Below the Limit of Detection (LOD)

Some values below the limit of detection (LOD) were identified for curcumin (native, glucuronide and sulfate) expressed as <<0.62>> in the database.

→ The number and percentage of values under the LOD were given for each parameter and visit.

Production of Graphical Representations

Figure 39:
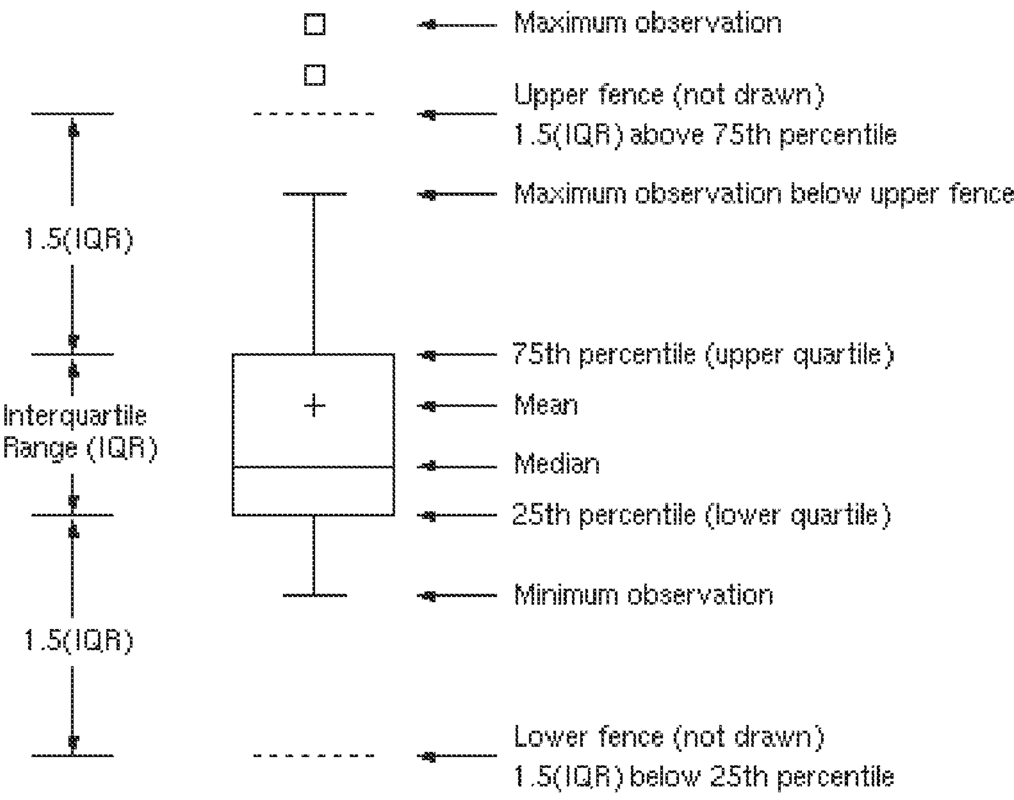
FIG. 39—Diagram of Quantitative variable on observed means: Box-and-whiskers plots for AUC parameters.

Quantitative variable on observed means: Box-and-whiskers plots for AUC parameters (illustrated in FIG. 39.

Checking of Statistical Tests Assumptions

Assumptions of normality and homoscedasticity were investigated by graphical representations of residuals produced by statistical models. In case of strong deviation from normality and/or homoscedasticity, log transformation (log 10) of study endpoints was considered.

Note for production of results:

STE=Standard turmeric powder extract 95% curcuminoids 1500 mg

TEP=Curcumin C3 complex California Gold Nutrition (1500 mg C3 Complex®)

NOV=Curcumin Cell'Innov (1000 mg Novasol®)

PHYT=Curcuma Platinum MannaVital (1000 mg Meriva®)

Turmipure GOLD™=Turmipure Gold 30% curcuminoids 300 mg

Statistical Methodology

Primary endpoint: Dose-normalized AUC between 0 and 24 hours was analyzed using the following mixed model for repeated measurements (SAS® PROC MIXED, statistical model n° 1):

$$Y=\text{Product}+\text{Visit}+\text{Baseline}+\text{Subject}_{random}$$

with:

Y: Dose-normalized AUC between 0 and 24 hours of analyt plasmatic concentration;

Product: Turmipure Gold™, STE, TEP, NOV, PHYT;

Visit: Visit V1 to V5;

Baseline: Parameter's value at T-10 time-point (T0 for AUC calculation);

$\text{Subject}_{random}$: Random factor.

If significant Visit effect ($p<0.05$): secondary analysis realized on first period (visit) in order to assess the product effect.

Comparison between products of interest→ Turmipure Gold™ compared to STE

Additional Analysis: Investigation of Gender Effect

Gender effect was investigated in this study using the following mixed model for repeated measurements (SAS® PROC MIXED, statistical model n° 2):

$$Y=\text{Product}+\text{Visit}+\text{Gender}+\text{Product}*\text{Gender}+\text{Baseline}+\text{Subject}_{random}$$

With:

Y: Endpoint;

Product: Turmipure Gold™, STE, TEP, NOV, PHYT;

Visit: Visit V1 to V5;

Gender: Female or Male;

Product*Gender: interaction between the product and the gender;

Baseline: Parameter's value at T-10 time-point (T0 for AUC calculation);

$\text{Subject}_{random}$: Random factor.

Comparisons between products of interest;

Turmipure GOLD™ compared to STE;

TEP compared to STE;

NOV compared to STE;

PHYT compared to STE;

TEP compared to Turmipure GOLD™;

NOV compared to Turmipure GOLD™;

PHYT compared to Turmipure GOLD™

If significant Visit effect ($p<0.05$): secondary analysis realized on first period (visit) in order to assess the product effect.

If significant Product*Gender interaction effect ($p<0.05$): treatment effect investigated in men and women separately (with production of descriptive statistics and graphic representations)

If significant Product*Gender interaction effect ($p>0.05$): treatment effect investigated globally (women and men together)

Statistical Methodology for Secondary Endpoints (Except for Relative Bioavailability)

Secondary endpoints were analyzed using the following mixed model for repeated measurements (SAS® PROC MIXED, statistical model n° 1):

$$Y=\text{Product}+\text{Visit}+\text{Baseline}+\text{Subject}_{random}$$

If significant Visit effect ($p<0.05$): secondary analysis realized on first period (visit) in order to assess the product effect.

Comparison between products of interest:

Turmipure GOLD™ compared to STE;

TEP compared to STE;

NOV compared to STE;

PHYT compared to STE;

TEP compared to Turmipure GOLD™;

NOV compared to Turmipure GOLD™;

PHYT compared to Turmipure GOLD™

Statistical methodology for relative bioavailability

Secondary endpoints were analyzed using the following mixed model for repeated measurements (SAS® PROC MIXED, statistical model n° 1):

$$Y=\text{Product}+\text{Visit}+\text{Subject}_{random}$$

If significant Visit effect ($p<0.05$): secondary analysis realized on first period (visit) in order to assess the product effect.

Comparison between products of interest:

TEP compared to Turmipure GOLD™;

NOV compared to Turmipure GOLD™;

PHYT compared to Turmipure GOLD™

Summary of the Results of the Primary Endpoints

Table 22 and 23: Initial Analysis of ITT and PP Populations

| ITT population | | | |
|---|---|---|---|
| | Between-group analysis | | |
| Endpoint | Product effect-Statistical significance | Comparison between Products | Statistical significance |
| Dose-normalized of AUC$_{0-24h}$ of Total curcuminoids (log-transformed data) | △ | Turmipure GOLD ™ vs STE (primary endpoint) | △ Turmipure > STE |
| | | TEP vs STE | ○ |
| | | NOV vs STE | △ NOV > STE |
| | | PHYT vs STE | △ PHYT > STE |
| | | TEP vs Turmipure GOLD ™ | △ TEP < Turmipure |
| | | NOV vs Turmipure GOLD ™ | △ NOV > Turmipure |
| | | PHYT vs Turmipure GOLD ™ | △ PHYT < Turmipure |

| PP population | | | |
|---|---|---|---|
| | Between-group analysis | | |
| Endpoint | Product effect-Statistical significance | Comparison between Products | Statistical significance |
| Dose-normalized of AUC$_{0-24h}$ of Total curcuminoids (log-transformed data) | △ | Turmipure GOLD ™ vs STE (primary endpoint) | △ Turmipure > STE |
| | | TEP vs STE | ○ |
| | | NOV vs STE | △ NOV > STE |
| | | PHYT vs STE | △ PHYT > STE |
| | | TEP vs Turmipure GOLD ™ | △ TEP < Turmipure |
| | | NOV vs Turmipure GOLD ™ | △ NOV > Turmipure |
| | | PHYT vs Turmipure GOLD ™ | △ PHYT < Turmipure |

Table 24 and 25: Additional Analysis of ITT and PP Populations (Investigation of Gender Effect)

| ITT population | | | |
|---|---|---|---|
| | Between-group analysis | | |
| Endpoint | Product*Gender effect-Statistical significance | Comparison between Products | Statistical significance |
| Dose-normalized of AUC$_{0-24h}$ of Total curcuminoids (log-transformed data) | ○ | Turmipure GOLD ™ vs STE (primary endpoint) | △ Turmipure > STE |
| | | TEP vs STE | ○ |
| | | NOV vs STE | △ NOV > STE |
| | | PHYT vs STE | △ PHYT > STE |
| | | TEP vs Turmipure GOLD ™ | △ TEP <Turmipure |
| | | NOV vs Turmipure GOLD ™ | △ NOV >Turmipure |
| | | PHYT vs Turmipure GOLD ™ | △ PHYT <Turmipure |

| PP population | | | |
|---|---|---|---|
| | Between-group analysis | | |
| Endpoint | Product*Gender effect-Statistical significance | Comparison between Products | Statistical significance |
| Dose-normalized of AUC$_{0-24h}$ of Total | ○ | Turmipure GOLD ™ vs STE (primary endpoint) | △ Turmipure > STE |

-continued

| PP population | | | |
|---|---|---|---|
| | Between-group analysis | | |
| Endpoint | Product*Gender effect-Statistical significance | Comparison between Products | Statistical significance |
| curcuminoids (log-transformed data) | | TEP vs STE | ○ |
| | | NOV vs STE | △ NOV > STE |
| | | PHYT vs STE | △ PHYT > STE |
| | | TEP vs Turmipure GOLD ™ | △ TEP <Turmipure |
| | | NOV vs Turmipure GOLD ™ | △ NOV >Turmipure |
| | | PHYT vs Turmipure GOLD ™ | △ PHYT <Turmipure |

△p-value < 0.05 (statistically signifcant);
○p-value > 0.05 (statistically non-significant

TABLE 26

| Dose-normalized of $AUC_{0-24h}$ of Total curcuminoids | | | | | | |
|---|---|---|---|---|---|---|
| Variable | Statistics | STE product (n = 30) | TEP product (n = 30) | NOV product (n = 30) | PHYT product (n = 30) | Turmipure GOLD ™ product (n = 30) |
| Dose-normalized $AUC_{0-24H}$ of Total curcuminoids (ng · h/mL/mg) | N | 30 | 30 | 30 | 29 | 30 |
| | N Miss | 0 | 0 | 0 | 1 | 0 |
| | Mean (SD) | 3.7 (1.75) | 3.2 (1.69) | 136.1 (37.40) | 13.0 (9.65) | 72.9 (25.49) |
| | (Min; Max) | (0.7; 9.7) | (0.8; 8.7) | (69.8; 220.8) | (1.7; 42.0) | (16.4; 139.6) |
| | Median (Q1; Q3) | 3.7 (2.5; 4.3) | 3.0 (2.1; 4.1) | 141.8 (105.6; 157.8) | 10.7 (6.2; 17.0) | 69.7 (55.2; 87.8) |

From the above analysis, it was concluded that for the ITT population:

Between-Group Analysis (all Genders Taken Together)
- No significant visit is identified (p=0.2245)→ Consequently, the analysis was performed on all visits.
- Significant Product effect (p<0.0001):
  - Primary endpoint: There is a statistically significant difference between Turmipure GOLD™ and STE (adjusted p<0.0001; diff[adjusted CI95%]=1.32 [1.18; 1.46]).
  - Others comparisons:
    - TEP vs STE (adjusted p=0.6948)
    - NOV vs STE (adjusted p<0.0001; diff[adjusted CI95%]=1.62 [1.48; 1.76])→ NOV>STE
    - PHYT vs STE (adjusted p<0.0001; diff[adjusted CI95%]=0.48 [0.34; 0.62])→ PHYT>STE
    - TEP vs Turmipure GOLD™ (adjusted p<0.0001; diff[adjusted CI95%]=−1.39 [−1.53;−1.25])→ TEP<Turmipure GOLD™
    - NOV vs Turmipure GOLD™ (adjusted p<0.0001; diff[adjusted CI95%]=0.29 [0.15; 0.43])→ NOV>Turmipure GOLD™
    - PHYT vs Turmipure GOLD™ (adjusted p<0.0001; diff[adjusted CI95%]=−0.84 [−0.99;−0.70])→ PHYT<Turmipure GOLD™

Additional Analysis: Investigation of Gender Effect
- No significant Visit (p=0.2456) and Product*Gender interaction (p=0.3804) effects: Analysis performed all gender taken together and on all visits.
- Significant Product effect (p<0.0001):
  - TEP vs STE (adjusted p=0.7091)
  - NOV vs STE (adjusted p<0.0001; diff[adjusted CI95%] =1.61 [1.47; 1.75])→ NOV>STE
    - PHYT vs STE (adjusted p<0.0001; diff[adjusted CI95%]=0.48 [0.34; 0.62])→ PHYT>STE
    - Turmipure GOLD™ vS STE (adjusted p<0.0001; diff [adjusted CI95%]=1.32 [1.18; 1.46])→ Turmipure GOLD™>STE
    - TEP vs Turmipure GOLD™ (adjusted p<0.0001; diff [adjusted CI95%]=−1.39 [−1.52;−1.25])→ TEP<Turmipure GOLD™
    - NOV vs Turmipure GOLD™ (adjusted p<0.0001; diff [adjusted CI95%]=0.29 [0.15; 0.43])→ NOV>Turmipure GOLD™
    - PHYT vs Turmipure GOLD™ (adjusted p<0.0001; diff[adjusted CI95%]=−0.84 [−0.98;−0.70])→ PHYT<Turmipure GOLD™

For the PP Population:
- Between-group analysis (all genders taken together)
  - Results are similar to results observed on ITT population.
  - Additional analysis: Investigation of Gender effect
  - Results are similar to results observed on ITT population.

Summary of the Results of the Secondary Endpoints

The results of the secondary endpoints are shown in the tables below for both the ITT (Tables 27 to 43) and PP (Tables 44 to 60) Populations respectively. The graphical representation of the data is provided in FIGS. 24 to 37.

The following key applies to each table, indicating the statistical significance of each result.

| | |
|---|---|
| ☐ p-value < 0.05 (statistically significant); | ⊠ p-value ≥ 0.10 (statistically non significant); |

*Analysis performed on V1 visit only (n = 30)

TABLE 27

Analysis of total curcuminoids (ng/mL) between products in the ITT population.

| Endpoint | Visit effect | Product effect | Between-group analysis-Satisfied significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24h [ng · h/mL] [Log10] | / | p < 0.0001 | / | / | p < 0.0001; NOV > STE | p < 0.0001; PHYT < STE | p = 0.0012; TEP < Turmipure | p = 0.0449; NOV > Turmipure | p < 0.0001; PHYT < Turmipure |
| DN of AUC0-8h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8h (ng · h/mL) [Log10] | / | p < 0.0001 | p = 0.0013; Turmipure > STE | / | p < 0.0001; NOV > STE | p < 0.0001; PHYT < STE | p < 0.0001; TEP < Turmipure | p < 0.0051; NOV > Turmipure | p < 0.0001; PHYT < Turmipure |
| DN of AUCa-infinity (ng · h/mL/mg) [Log10] | p = 0.0278* | p < 0.0001 | p = 0.0004; Turmipure > STE | / | p < 0.0001; NOV > STE | / | p < 0.0001; TEP < Turmipure | / | p < 0.0001; PHYT < Turmipure |
| AUC0-infinity (ng · h/mL) [Log10] | p = 0.0278* | p < 0.0001 | / | / | / | / | / | / | / |
| Normalized Cmax (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| Cmax (ng · h/mL) [Log10] | / | p < 0.0001 | p = 0.0010; Turmipure > STE | / | p < 0.0001; NOV > STE | p < 0.0001; PHYT < STE | p < 0.0001; TEP < Turmipure | p < 0.0001; NOV > Turmipure | p < 0.0001; PHYT < Turmipure |
| Ret. bio. between 0 and 24 h [Log10] | / | p < 0.0001 | ⊠ | ⊠ | ⊠ | ⊠ | p < 0.0001; TEP < Turmipure | p < 0.0001; NOV > Turmipure | p < 0.0001; PHYT < Turmipure |
| Ret. bio. between 0 and 8 h [Log10] | / | p < 0.0001 | ⊠ | ⊠ | ⊠ | ⊠ | p < 0.0001; TEP < Turmipure | p < 0.0001; NOV > Turmipure | p < 0.0001; PHYT < Turmipure |
| Ret. bio. between 0 and infinity [Log10] | p = 0.0169* | p < 0.0001 | ⊠ | ⊠ | ⊠ | ⊠ | p = 0.0008; TEP < Turmipure | | p = 0.0110; PHYT < Turmipure |
| Half-life (minutes) [Log10] | / | p < 0.0001 | p = 0.0097; Turmipure < STE | / | p = 0.0084; NOV < STE | / | p = 0.0442; TEP > Turmipure | / | p = 0.0018; PHYT > Turmipure |
| Terminal elimination rate constant [Log10] | / | p < 0.0001 | p = 0.0097; Turmipure > STE | / | p = 0.0084; NOV > STE | / | p = 0.0442; TEP < Turmipure | / | p = 0.0018; PHYT < Turmipure |
| Tmax minutes [Log10] | / | p < 0.0001 | / | / | p < 0.0001; NOV > STE | p < 0.0279; PHYT > STE | / | p < 0.0001; NOV < Turmipure | p < 0.0002; PHYT > Turmipure |

TABLE 28

Analysis of total curcumin (ng/mL) between products in the ITT population.

| Endpoint | Visit effect | Product effect | Between-group analysis-Satisfied significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24h (ng · h/mL/mg) [Log10] | / | p < 0.0001 | p = 0.0012; Turmipure > STE | / | / | / | p = 0.0007; TEP < Turmipure | / | / |
| AUC0-24h [ng · h/mL] [Log10] | / | / | / | / | / | / | / | / | / |
| DN of AUC0-8h (ng · h/mL/mg) [Log10] | p = 0.0276* | / | / | / | / | / | / | / | / |
| AUC0-8h (ng · h/mL) [Log10] | / | / | / | / | / | / | / | / | / |
| DN of AUCa-infinity (ng · h/mL/mg) [Log10] | / | p = 0.0012 | p = 0.0024; Turmipure > STE | / | / | / | p = 0.0073; TEP < Turmipure | / | / |
| AUC0-infinity (ng · h/mL) [Log10] | / | / | / | / | / | / | / | / | / |
| Normalized Cmax (ng · h/mL/mg) [Log10] | p = 0.0407* | / | / | / | / | / | / | / | / |
| Cmax (ng · h/mL) [Log10] | / | / | / | / | / | / | / | / | / |
| Ret. bio. between 0 and 24 h [Log10] | / | / | X | X | X | X | / | / | / |
| Ret. bio. between 0 and 8 h [Log10] | / | p = 0.0177 | X | X | X | X | p = 0.0260; TEP < Turmipure | / | / |
| Ret. bio. between 0 and infinity [Log10] | X | X | X | X | X | X | X | X | X |
| Half-life (minutes) [Log10] | / | / | / | / | / | / | / | / | / |
| Terminal elimination rate constant [Log10] | / | / | / | / | / | / | / | / | / |
| Tmax minutes [Log10] | / | / | / | / | / | / | / | / | / |

TABLE 29

Analysis of total curcumin (ng/mL) between products in the ITT population.

| Endpoint | Visit effect | Product effect | Between-group analysis-Satisfied significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24h [ng · h/mL] [Log10] | / | p < 0.0001 | / | / | p < 0.0001; NOV > STE | p = 0.0002; PHYT > STE | / | p < 0.0001; NOV > Turmipure | p = 0.0002; PHYT < Turmipure |
| DN of AUC0-8h (ng · h/mL/mg) | / | p < 0.0001 | p < 0.0001; Turmipure > | / | p < 0.0001; NOV > | p = 0.0125; PHYT > STE | p < 0.0001; TEP < | p < 0.0001; NOV > | p < 0.0001; PHYT < Turmipure |

TABLE 29-continued

Analysis of total curcumin (ng/mL) between products in the ITT population.

| Endpoint | Visit effect | Product effect | Between-group analysis-Satisfied significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| [Log10] | | | STE | | STE | | Turmipure | Turmipure | |
| AUC0-8h (ng · h/mL) [Log10] | | p < 0.0001 | | | p < 0.0001; NOV > STE | p < 0.0001; PHYT > STE | | p < 0.0001; NOV > Turmipure | p < 0.0001; PHYT < Turmipure |
| DN of AUCa-infinity (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | |
| AUC0-infinity (ng · h/mL) [Log10] | | p = 0.0294 | | | | | | p < 0.0001; NOV > Turmipure | |
| Normalized Cmax (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p = 0.0253; NOV > Turmipure | p < 0.0001; PHYT < Turmipure |
| Cmax (ng · h/mL) [Log10] | | p < 0.0001 | | | p < 0.0001; NOV > STE | p = 0.0248; PHYT > STE | | p < 0.0001; NOV > Turmipure | p = 0.0002; PHYT < Turmipure |
| Ret. bio. between 0 and 24 h [Log10] | | p < 0.0001 | X | X | X | X | p < 0.0001; TEP < Turmipure | p < 0.0001; NOV > Turmipure | p < 0.0001; PHYT < Turmipure |
| Ret. bio. between 0 and 8 h [Log10] | | p < 0.0001 | X | X | X | X | p < 0.0001; TEP < Turmipure | p < 0.0001; NOV > Turmipure | p < 0.0001; PHYT < Turmipure |
| Ret. bio. between 0 and infinity [Log10] | | p < 0.0001 | X | X | X | X | p < 0.0001; TEP < Turmipure | p < 0.0001; NOV > Turmipure | |
| Half-life (minutes) [Log10] | | p < 0.0001 | p = 0.0103; Turmipure > STE | | p = 0.0001; NOV > STE | | | | |
| Terminal elimination rate constant [Log10] | | p < 0.0001 | p = 0.0103; Turmipure > STE | | p = 0.0001; NOV > STE | | | | |
| Tmax minutes [Log10] | | p < 0.0001 | | | p = 0.0044; NOV > STE | | | p = 0.0329; NOV > Turmipure | |

TABLE 30

Analysis of curcumin sulfate (ng/mL) between products in the ITT population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| DN of AUC0-24 h (ng · h/mL/mg) [Log10] | p = 0.0037* | p < 0.0001 | p < 0.0001; Turmipure > STE | | p < 0.0001; NOV > STE | p < 0.0001; PHYT > STE | p < 0.0001; TEP < Turmipure | | p = 0.0017; PHYT < Turmipure |
| AUC0-24 h (ng · h/mL) [Log10] | p = 0.0037* | | | | | | | | |
| DN of AUC0-8 h (ng · h/mL/mg) [Log10] | p = 0.0029* | p < 0.0001 | p < 0.0001; Turmipure > STE | | p < 0.0001; NOV > STE | p < 0.0001; PHYT > STE | p < 0.0001; TEP < Turmipure | p = 0.0041; NOV > Turmipure | p < 0.0001; PHYT < Turmipure |
| AUC0-8 h (ng · h/mL) [Log10] | p = 0.0293* | p = 0.0005 | | | | | | | |

TABLE 30-continued

Analysis of curcumin sulfate (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-infinity (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | / | p < 0.0001; PHYT < Turmipure |
| AUC0-infinity (ng · h/mL) [Log10] | / | / | / | / | / | / | / | / | / |
| Normalized Cmax (ng/mL/mg) [Log10] | p = 0.0003* | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p = 0.0005; PHYT < Turmipure |
| Cmax (ng/mL) [Log10] | p = 0.0003* | p < 0.0001 | / | / | p = 0.0020; NOV > STE | / | / | p = 0.0026; NOV > Turmipure | / |
| Rel. bio. between 0 and 24 h [Log10] | p = 0.0260* | p < 0.0001 | X | X | X | X | p < 0.0001; TEP < Turmipure | / | p = 0.0015; PHYT < Turmipure |
| Rel. bio. between 0 and 8 h [Log10] | / | p < 0.0001 | X | X | X | X | p < 0.0001; TEP < Turmipure | p = 0.0002; NOV > Turmipure | p < 0.0001; PHYT < Turmipure |
| Rel. bio. between 0 and infinity [Log10] | p = 0.0100* | p = 0.0143 | X | X | X | X | / | / | / |
| Half-life (minutes) [Log10] | / | / | / | / | / | / | / | / | / |
| Terminal elimination rate constant [Log10] | / | / | / | / | / | / | / | / | / |
| Tmax (minutes) [Log10] | / | p < 0.0001 | / | / | p < 0.0001; NOV < STE | / | p = 0.00295; TEP > Turmipure | p < 0.0001, NOV < Turmipure | p = 0.0043; PHYT > Turmipure |

TABLE 31

Analysis of curcumin and its relative sulfate and glucuronide metabolites (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | / | p < 0.0001 | / | / | p = 0.0173; NOV > STE | p < 0.0001; PHYT > STE | / | p = 0.0031; NOV > Turmipure | p < 0.0001; PHYT < Turmipure |
| DN of AUC0-8 h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8 h (ng · h/mL) [Log10] | / | p < 0.0001 | / | / | p < 0.0001; NOV > STE | p < 0.0001; PHYT < STE | p < 0.0265; TEP < Turmipure | p < 0.0001; NOV > Turmipure | p < 0.0001; PHYT < Turmipure |
| DN of AUC0-infinity (ng · h/mL/mg) [Log10] | p = 0.0033* | p < 0.0001 | p < 0.0001; Turmipure > STE | / | p < 0.0001; NOV > STE | p = 0.0158; PHYT > STE | p < 0.0001; TEP < Turmipure | / | p = 0.0333; PHYT < Turmipure |
| AUC0-infinity (ng · h/mL) [Log10] | p = 0.0033* | / | / | / | / | / | / | / | / |

TABLE 31-continued

Analysis of curcumin and its relative sulfate and glucuronide metabolites (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | p = 0.0408* | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p = 0.0018; PHYT < Turmipure |
| Cmax (ng/mL) [Log10] | p = 0.0408* | p < 0.0001 | | | p < 0.0001; NOV > STE | | | p < 0.0001; NOV > Turmipure | |
| Rel. bio. between 0 and 24 h [Log10] | | p < 0.0001 | | | | | p < 0.0001; TEP < Turmipure | p < 0.0001; NOV > Turmipure | p = 0.0001; PHYT < Turmipure |
| Rel. bio. between 0 and 8 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and infinity [Log10] | p = 0.0065* | p = 0.0002 | | | | | p = 0.0190; TEP < Turmipure | | |
| Half-life (minutes) [Log10] | | p = 0.0010 | | | | | | | p = 0.0062; PHYT > Turmipure |
| Terminal elimination rate constant [Log10] | | p = 0.0010 | | | | | | | p = 0.0062; PHYT < Turmipure |
| Tmax (minutes) [Log10] | | p < 0.0001 | | | p < 0.0001; NOV < STE | | | p < 0.0001; NOV < Turmipure | p = 0.0418; PHYT > Turmipure |

TABLE 32

Analysis of DMC glucuronide (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | |
| AUC0-24 h (ng · h/mL) [Log10] | | p < 0.0001 | | | p = 0.0010; NOV > STE | | | p < 0.0001; NOV > Turmipure | |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p = 0.0131; PHYT < Turmipure |
| AUC0-8 h (ng · h/mL) [Log10] | | p < 0.0001 | | | p < 0.0001; NOV > STE | | | p < 0.0001; NOV > Turmipure | |
| DN of AUC0-infinity (ng · h/mL/mg) [Log10] | | p < 0.0001 | p < 0.0001; Turmipure > STE | | p < 0.0001; NOV > STE | p = 0.0135; PHYT > STE | p < 0.0001; TEP < Turmipure | p = 0.0187; NOV > Turmipure | |
| AUC0-infinity (ng · h/mL) [Log10] | | | | | | | | | |

TABLE 32-continued

| Analysis of DMC glucuronide (ng/mL) between products in the ITT population. | | | | | | | | | |
|---|---|---|---|---|---|---|---|---|---|
| | | | Between-group analysis-Statistical significance of comparisons between products (adjusted p-value, Tukey adjustment) | | | | | | |
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | | p < 0.0001 | p < 0.0001; Turmipure > STE | | p < 0.0001; NOV > STE | p = 0.0066; PHYT > STE | p < 0.0001; TEP < Turmipure | p < 0.0001; NOV > Turmipure | p = 0.0301; PHYT < Turmipure |
| Cmax (ng/mL) [Log10] | | p < 0.0001 | | | p < 0.0001; NOV > STE | | | p < 0.0001; NOV > Turmipure | |
| Rel. bio. between 0 and 24 h [Log10] | | p < 0.0001 | | | | | p < 0.0001; TEP < Turmipure | p < 0.0001; NOV > Turmipure | |
| Rel. bio. between 0 and 8 h [Log10] | | p < 0.0001 | | | | | p < 0.0001; TEP < Turmipure | p < 0.0001; NOV > Turmipure | p = 0.0207; PHYT < Turmipure |
| Rel. bio. between 0 and infinity [Log10] | | p < 0.0001 | | | | | p < 0.0001; TEP < Turmipure | | |
| Half-life (minutes) [Log10] | | p = 0.0035 | | | | | | | |
| Terminal elimination rate constant [Log10] | | p = 0.0002 | | | p = 0.0008; NOV > STE | | | p = 0.0282; NOV > Turmipure | |
| Tmax (minutes) [Log10] | | p = 0.0108 | | | | | | | |

TABLE 33

| Analysis of DMC sulfate (ng/mL) between products in the ITT population. | | | | | | | | | |
|---|---|---|---|---|---|---|---|---|---|
| | | | Between-group analysis-Statistical significance of comparisons between products (adjusted p-value, Tukey adjustment) | | | | | | |
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | | p = 0.0003; PHYT < Turmipure |
| AUC0-24 h (ng · h/mL) [Log10] | | p = 0.0051 | | | p = 0.0068 NOV < STE | | | | |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | | p < 0.0001; PHYT < Turmipure |
| AUC0-8 h (ng · h/mL) [Log10] | | | | | | | | | |
| DN of AUC0-infinity (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | | p = 0.0101; PHYT < Turmipure |
| AUC0-infinity (ng · h/mL) [Log10] | | p = 0.0016 | | | p = 0.0019; NOV < STE | | | | |
| Normalized Cmax (ng/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p = 0.0106; NOV > Turmipure | p < 0.0001; PHYT < Turmipure |
| Cmax (ng/mL) [Log10] | | | | | | | | | |

TABLE 33-continued

Analysis of DMC sulfate (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Rel. bio. between 0 and 24 h [Log10] | | p < 0.0001 | | | | | p < 0.0001; TEP < Turmipure | | p = 0.0007; PHYT < Turmipure |
| Rel. bio. between 0 and 8 h [Log10] | | p < 0.0001 | | | | | p < 0.0001; TEP < Turmipure | | p < 0.0001; PHYT < Turmipure |
| Rel. bio. between 0 and infinity [Log10] | | p < 0.0001 | | | | | p < 0.0001; TEP < Turmipure | | |
| Half-life (minutes) [Log10] | | | | | | | | | |
| Terminal elimination rate constant [Log10] | | | | | | | | | |
| Tmax (minutes) [Log10] | | p < 0.0001 | | | p < 0.0001; NOV < STE | | | p = 0.0022; NOV < Turmipure | |

TABLE 34

Analysis of DMC and its relative sulfate and glucuronide metabolites (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p = 0.0293; NOV > Turmipure | p = 0.0005; PHYT < Turmipure |
| AUC0-24 h (ng · h/mL) [Log10] | | | | | | | | | |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8 h (ng · h/mL) [Log10] | | p = 0.0002 | | | p = 0.0112; NOV > STE | | | p = 0.0075; NOV > Turmipure | |
| DN of AUC0-infinity (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | | p < 0.0001; PHYT < Turmipure |
| AUC0-infinity (ng · h/mL) [Log10] | | p = 0.0150 | | | | | | | |
| Normalized Cmax (ng/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p = 0.0011; PHYT < Turmipure |
| Cmax (ng/mL) [Log10] | | p < 0.0001 | | | p < 0.0001; NOV > STE | | | p < 0.0001; NOV > Turmipure | |
| Rel. bio. between 0 and 24 h [Log10] | | p < 0.0001 | | | | | p < 0.0001; TEP < Turmipure | | p = 0.0052; PHYT < Turmipure |
| Rel. bio. between 0 and 8 h [Log10] | | p < 0.0001 | | | | | p < 0.0001; TEP < Turmipure | p = 0.0004; NOV > Turmipure | p < 0.0001; PHYT < Turmipure |

TABLE 34-continued

Analysis of DMC and its relative sulfate and glucuronide metabolites (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Rel. bio. between 0 and infinity [Log10] | — | p < 0.0001 | X | X | X | X | p < 0.0001; TEP < Turmipure | — | p = 0.0006; PHYT < Turmipure |
| Half-life (minutes) [Log10] | — | p = 0.0004 | — | — | p = 0.0019; NOV < STE | — | — | p = 0.0018; NOV < Turmipure | — |
| Terminal elimination rate constant [Log10] | — | p = 0.0004 | — | — | p = 0.0019; NOV > STE | — | — | p = 0.0018; NOV > Turmipure | — |
| Tmax (minutes) [Log10] | — | p < 0.0001 | — | — | p < 0001; NOV < STE | p = 0.0117; PHYT > STE | — | p = 0.0060; NOV < Turmipure | p = 0.0003; PHYT > Turmipure |

TABLE 35

Analysis of BDMC glucuronide (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | — | p < 0.0001 | — | — | p < 0.0001; NOV > STE | — | — | p = 0.0001; NOV > Turmipure | — |
| AUC0-24 h (ng · h/mL) [Log10] | — | p = 0.0003 | p = 0.0003; Turmipure < STE | — | — | — | — | p = 0.0040; NOV > Turmipure | — |
| DN of AUC0-8 h (ng · h/mL/mg) [Log10] | — | p < 0.0001 | — | — | p < 0.0001; NOV > STE | — | — | p < 0.0001; NOV > Turmipure | — |
| AUC0-8 h (ng · h/mL) [Log10] | — | p < 0.0001 | p < 0.0003; Turmipure < STE | p = 0.0290; TEP < STE | — | p = 0.0001; PHYT < STE | p < 0.0153; TEP > Turmipure | p < 0.0001; NOV > Turmipure | — |
| DN of AUC0-infinity (ng · h/mL/mg) [Log10] | — | p < 0.0001 | — | — | p = 0.0006; NOV > STE | — | — | p = 0.0010; NOV > Turmipure | — |
| AUC0-infinity (ng · h/mL) [Log10] | — | p = 0.0009 | p = 0.0060; Turmipure < STE | — | — | p = 0.0263; PHYT < STE | p = 0.0202; TEP > Turmipure | p = 0.0439; NOV > Turmipure | — |
| Normalized Cmax (ng/mL/mg) [Log10] | — | p < 0.0001 | — | — | p < 0.0001; NOV > STE | — | p = 0.0007; TEP < Turmipure | p < 0.0001; NOV > Turmipure | — |
| Cmax (ng/mL) [Log10] | — | p < 0.0001 | p < 0.0001; Turmipure < STE | p = 0.0031; TEP < STE | — | p < 0.0001; PHYT < STE | — | p < 0.0001; NOV > Turmipure | — |
| Rel. bio. between 0 and 24 h [Log10] | — | p < 0.0001 | X | X | X | X | p = 0.0291; TEP < Turmipure | p = 0.0005; NOV > Turmipure | — |
| Rel. bio. between 0 and 8 h [Log10] | — | p < 0.0001 | X | X | X | X | — | p < 0.0001; NOV > Turmipure | — |
| Rel. bio. between 0 and infinity [Log10] | — | p = 0.0275 | X | X | X | X | — | — | — |
| Half-life (minutes) [Log10] | — | p < 0.0001 | p = 0.0020; Turmipure < STE | — | — | p = 0.0043; PHYT < STE | p = 0.0116; TEP > Turmipure | p = 0.0075; NOV > Turmipure | — |
| Terminal elimination rate constant | — | p < 0.0001 | p = 0.0020; Turmipure < | p = 0.0252; TEP < | — | p = 0.0015; PHYT < | — | p < 0.0001; NOV > | — |

TABLE 35-continued

Analysis of BDMC glucuronide (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| [Log10] Tmax (minutes) [Log10] | | p = 0.0275 | STE | STE | | STE | | Turmipure p = 0.0116; NOV > Turmipure | |

TABLE 36

Analysis of BDMC sulfate (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p = 0.0055 | | | | | p = 0.0237; TEP < Turmipure | | |
| AUC0-24 h (ng · h/mL) [Log10] | | p < 0.0001 | p < 0.0001; Turmipure < STE | | p < 0.0001; NOV < STE | p < 0.0008; PHYT < STE | p < 0.0001; TEP > Turmipure | | p = 0.0280; PHYT > Turmipure |
| DN of AUC0-8 h (ng · h/mL/mg) [Log10] | | p < 0.0001 | | | p = 0.0101; NOV > STE | | p < 0.0001; TEP < Turmipure | | |
| AUC0-8 h (ng · h/mL) [Log10] | | p < 0.0001 | p < 0.0001; Turmipure < STE | | p < 0.0001; NOV < STE | p < 0.0001; PHYT < STE | p < 0.0001; TEP > Turmipure | | |
| DN of AUC0-infinity (ng · h/mL/mg) [Log10] | | | | | | | | | |
| AUC0-infinity (ng · h/mL) [Log10] | | p < 0.0001 | p < 0.0001; Turmipure < STE | | p = 0.0002; NOV < STE | p = 0.0059; PHYT < STE | p < 0.0001; TEP > Turmipure | | |
| Normalized Cmax (ng/mL/mg) [Log10] | p = 0.0424* | p = 0.0248 | | | | | | | |
| Cmax (ng/mL) [Log10] | p = 0.0300* | p = 0.0029 | p = 0.0109; Turmipure < STE | | p = 0.0392; NOV < STE | p = 0.0109; PHYT < STE | | | |
| Rel. bio. between 0 and 24 h [Log10] | | p = 0.0320 | | | | | | | |
| Rel. bio. between 0 and 8 h [Log10] | | p = 0.0002 | | | | | p = 0.0024; TEP < Turmipure | | |
| Rel. bio. between 0 and infinity [Log10] | | | | | | | | | |
| Half-life (minutes) [Log10] | | p < 0.0001 | p < 0.0001; Turmipure < STE | | | p = 0.0416; PHYT < STE | p < 0.0001; TEP > Turmipure | | |
| Terminal elimination rate constant [Log10] | | p = 0.0012 | | | p = 0.0021; NOV > STE | | | | |
| Tmax (minutes) [Log10] | | p = 0.0219 | | | | | | | p = 0.0367; PHYT > Turmipure |

TABLE 37

Analysis of BDMC and its relative sulfate and glucuronide metabolites (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | | | p = 0.0040; NOV > STE | | p = 0.0015; TEP < Turmipure | | |
| AUC0-24 h (ng · h/mL) [Log10] | | p < 0.0001 | p < 0.0001; Turmipure < STE | | p < 0.0001; NOV < STE | p = 0.0004; PHYT < STE | p < 0.0001; TEP > Turmipure | | p = 0.0111; PHYT > Turmipure |
| DN of AUC0-8 h (ng · h/mL/mg) [Log10] | | p < 0.0001 | p < 0.0001; Turmipure > STE | | p < 0.0001; NOV > STE | | p < 0.0001; TEP < Turmipure | p = 0.0452; NOV > Turmipure | |
| AUC0-8 h (ng · h/mL) [Log10] | | p < 0.0001 | p < 0.0001; Turmipure < STE | | p < 0.0001; NOV < STE | p < 0.0001; PHYT < STE | p < 0.0001; TEP > Turmipure | p = 0.0064; NOV > Turmipure | |
| DN of AUC0-infinity (ng · h/mL/mg) [Log10] | | p = 0.0033 | | | | p = 0.0350; PHYT > STE | | | |
| AUC0-infinity (ng · h/mL) [Log10] | | p < 0.0001 | p < 0.0001; Turmipure < STE | | p = 0.0003; NOV < STE | | p < 0.0001; TEP > Turmipure | | p = 0.0168; PHYT > Turmipure |
| Normalized Cmax (ng/mL/mg) [Log10] | | p < 0.0001 | p < 0.0001; Turmipure > STE | | p < 0.0001; NOV > STE | | p < 0.0001; TEP < Turmipure | p < 0.0001; NOV > Turmipure | p = 0.0054; PHYT < Turmipure |
| Cmax (ng/mL) [Log10] | | p < 0.0001 | p < 0.0001; Turmipure < STE | p = 0.0010; TEP < STE | p = 0.0086; NOV < STE | p < 0.0001; PHYT < STE | p < 0.0001; TEP > Turmipure | p < 0.0001; NOV > Turmipure | |
| Rel. bio. between 0 and 24 h [Log10] | | p = 0.0004 | X | X | X | X | p = 0.0303; TEP < Turmipure | | |
| Rel. bio. between 0 and 8 h [Log10] | | p < 0.0001 | X | X | X | X | p < 0.0001; TEP < Turmipure | | |
| Rel. bio. between 0 and infinity [Log10] | | p = 0.0453 | X | X | X | X | | | |
| Half-life (minutes) [Log10] | | p < 0.0001 | p = 0.0025; Turmipure < STE | | p = 0.0201; NOV < STE | | p < 0.0001; TEP > Turmipure | | p = 0.0310; PHYT > Turmipure |
| Terminal elimination rate constant [Log10] | | p < 0.0001 | | | p < 0.0001; NOV > STE | | | p = 0.0003; NOV > Turmipure | |
| Tmax (minutes) [Log10] | | p = 0.0133 | | | | | | | p = 0.0107; PHYT > Turmipure |

TABLE 38

Analysis of THC glucuronide (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | | p < 0.0001; TEP < Turmipure | p < 0.0001; NOV > Turmipure | p < 0.0001; PHYT < Turmipure |
| AUC0-24 h (ng · h/mL) [Log10] | | p < 0.0001 | | | p = 0.0212; NOV > STE | p < 0.0001; PHYT < STE | p = 0.0289; TEP < Turmipure | | p < 0.0001; PHYT < Turmipure |
| DN of AUC0-8 h (ng · h/mL/mg) [Log10] | | p < 0.0001 | p < 0.0001; Turmipure > STE | | p < 0.0001; NOV > STE | | p < 0.0001; TEP < Turmipure | p < 0.0001; NOV > Turmipure | p < 0.0001; PHYT < Turmipure |

TABLE 38-continued

Analysis of THC glucuronide (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| AUC0-8 h (ng · h/mL) [Log10] | | p < 0.0001 | | | p = 0.0009; NOV > STE | p < 0.0001; PHYT < STE | p = 0.0020; TEP < Turmipure | | p < 0.0001; PHYT < Turmipure |
| DN of AUC0-infinity (ng · h/mL/mg) [Log10] | | p < 0.0001 | p < 0.0001; Turmipure > STE | | p < 0.0001; NOV > STE | p = 0.0387; PHYT < STE | p < 0.0001; TEP < Turmipure | | p < 0.0001; PHYT < Turmipure |
| AUC0-infinity (ng · h/mL) [Log10] | | p < 0.0001 | | | | p < 0.0001; PHYT < STE | p = 0.0171; TEP < Turmipure | | p < 0.0001; PHYT < Turmipure |
| Normalized Cmax (ng/mL/ mg) [Log10] | | p < 0.0001 | p < 0.0001; Turmipure > STE | | p < 0.0001; NOV > STE | p = 0.0173; PHYT > STE | p < 0.0001; TEP < Turmipure | p < 0.0001; NOV > Turmipure | p < 0.0001; PHYT < Turmipure |
| Cmax (ng/mL) [Log10] | | p < 0.0001 | | | p < 0.0001; NOV > STE | p < 0.0001; PHYT < STE | p = 0.0359; TEP < Turmipure | | p < 0.0001; PHYT < Turmipure |
| Rel. bio. between 0 and 24 h [Log10] | | p < 0.0001 | | | | | p < 0.0001; TEP < Turmipure | p = 0.0030; NOV > Turmipure | p < 0.0001; PHYT < Turmipure |
| Rel. bio. between 0 and 8 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and infinity [Log10] | | p < 0.0001 | | | | | p < 0.0001; TEP < Turmipure | | p < 0.0001; PHYT < Turmipure |
| Half-life (minutes) [Log10] | | p < 0.0001 | | | | p < 0.0001; PHYT < STE | | | p < 0.0001; PHYT < Turmipure |
| Terminal elimination rate constant [Log10] | | p < 0.0001 | | | | | | | |
| Tmax (minutes) [Log10] | | p < 0.0001 | | | | p = 0.0004; PHYT < STE | | | p = 0.0003; PHYT < Turmipure |

TABLE 39

Analysis of THC sulfate (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | p = 0.0057* | | | | | | | | |
| AUC0-24 h (ng · h/mL) [Log10] | p = 0.0328* | | | | | | | | |
| DN of AUC0-8 h (ng · h/mL/mg) [Log10] | p = 0.0109* | | | | | | | | |
| AUC0-8 h (ng · h/mL) [Log10] | | p < 0.0001 | | | | p = 0.0067; PHYT < STE | | | p = 0.0003; PHYT < Turmipure |

TABLE 39-continued

Analysis of THC sulfate (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-infinity (ng · h/mL/mg) [Log10] | | p = 0.0013 | | | p = 0.0327; NOV > STE | | | | |
| AUC0-infinity (ng · h/mL) [Log10] | | p = 0.0134 | | | | | | | |
| Normalized Cmax (ng/mL/mg) [Log10] | p = 0.0007* | p = 0.0438 | | | | | | | |
| Cmax (ng/mL) [Log10] | | p = 0.0006 | | | | p = 0.0315; PHYT < STE | | | p = 0.0005; PHYT < Turmipure |
| Rel. bio. between 0 and 24 h [Log10] | | p = 0.0022 | | | | | | | |
| Rel. bio. between 0 and 8 h [Log10] | | p < 0.0001 | | | | | p = 0.0039; TEP < Turmipure | | p = 0.0119; PHYT < Turmipure |
| Rel. bio. between 0 and infinity [Log10] | | | | | | | | | |
| Half-life (minutes) [Log10] | | p = 0.0134 | | | | | | | |
| Terminal elimination rate constant [Log10] | | p = 0.0412 | | | | | | | p = 0.0184; PHYT < Turmipure |
| Tmax (minutes) [Log10] | p = 0.0309* | | | | | | | | |

TABLE 40

Analysis of HHC glucuronide (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p = 0.0013; NOV > Turmipure | p < 0.0001; PHYT < Turmipure |
| AUC0-24 h (ng · h/mL) [Log10] | | p < 0.0001 | p = 0.0002; Turmipure > STE | | p < 0.0001; NOV > STE | p < 0.0001; PHYT < STE | p < 0.0001; TEP < Turmipure | | p < 0.0001; PHYT < Turmipure |
| DN of AUC0-8 h (ng · h/mL/mg) [Log10] | | p < 0.0001 | p < 0.0001; Turmipure > STE | | p < 0.0001; NOV > STE | | p < 0.0001; TEP < Turmipure | p < 0.0001; NOV > Turmipure | p < 0.0001; PHYT < Turmipure |
| AUC0-8 h (ng · h/mL) [Log10] | | p < 0.0001 | p = 0.0015; Turmipure > STE | | p < 0.0001; NOV > STE | p < 0.0001; PHYT < STE | p < 0.0001; TEP < Turmipure | | p < 0.0001; PHYT < Turmipure |
| DN of AUC0-infinity (ng · h/mL/mg) [Log10] | | p < 0.0001 | p < 0.0001; Turmipure > STE | | p < 0.0001; NOV > STE | p = 0.0352; PHYT > STE | p < 0.0001; TEP < Turmipure | p = 0.0235; NOV > Turmipure | p < 0.0001; PHYT < Turmipure |
| AUC0-infinity (ng · h/mL) [Log10] | | p < 0.0001 | | | p = 0.0133; NOV > STE | p < 0.0001; PHYT < STE | p = 0.0192; TEP < Turmipure | | p < 0.0001; PHYT < Turmipure |
| Normalized Cmax (ng/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| Cmax (ng/mL) [Log10] | | p < 0.0001 | p = 0.0002; Turmipure > STE | | p < 0.0001; NOV > STE | p < 0.0001; PHYT < STE | p < 0.0001; TEP < Turmipure | p < 0.0001; NOV > Turmipure | p < 0.0001; PHYT < Turmipure |

TABLE 40-continued

Analysis of HHC glucuronide (ng/mL) between products in the ITT population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| Rel. bio. between 0 and 24 h [Log10] | / | p < 0.0001 | X | X | X | X | p < 0.0001; TEP < Turmipure | p = 0.0007; NOV > Turmipure | p < 0.0001; PHYT < Turmipure |
| Rel. bio. between 0 and 8 h [Log10] | / | p < 0.0001 | X | X | X | X | p < 0.0001; TEP < Turmipure | p < 0.0001; NOV > Turmipure | p < 0.0001; PHYT < Turmipure |
| Rel. bio. between 0 and infinity [Log10] | / | p < 0.0001 | X | X | X | X | p < 0.0001; TEP < Turmipure | / | p < 0.0001; PHYT < Turmipure |
| Half-life (minutes) [Log10] | / | / | / | / | / | / | / | / | / |
| Terminal elimination rate constant [Log10] | / | / | / | / | / | / | / | / | / |
| Tmax (minutes) [Log10] | / | p < 0.0001 | / | / | p < 0.0001; NOV < STE | p = 0.0399; PHYT > STE | / | p < 0.0001; NOV < Turmipure | p < 0.0001; PHYT > Turmipure |

TABLE 41

Analysis of HHC sulfate (ng/mL) between products in the ITT population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| DN of AUC0-24 h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | / | p < 0.0001 | p = 0.0010; Turmipure > STE | / | p < 0.0001; NOV > STE | p < 0.0001; PHYT < STE | p < 0.0001; TEP < Turmipure | / | p < 0.0001; PHYT < Turmipure |
| DN of AUC0-8 h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p = 0.0002; NOV > Turmipure | p < 0.0001; PHYT < Turmipure |
| AUC0-8 h (ng · h/mL) [Log10] | / | p < 0.0001 | p = 0.0002; Turmipure > STE | / | p < 0.0001; NOV > STE | p < 0.0001; PHYT < STE | p < 0.0001; TEP < Turmipure | / | p < 0.0001; PHYT < Turmipure |
| DN of AUC0-infinity (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p = 0.0006; NOV > Turmipure | p < 0.0001; PHYT < Turmipure |
| AUC0-infinity (ng · h/mL) [Log10] | / | p < 0.0001 | / | / | p = 0.0313; NOV > STE | p < 0.0001; PHYT < STE | p = 0.0228; TEP < Turmipure | / | p < 0.0001; PHYT < Turmipure |
| Normalized Cmax (ng/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| Cmax (ng/mL) [Log10] | / | p < 0.0001 | p < 0.0001; Turmipure > STE | / | p < 0.0001; NOV > STE | p < 0.0001; PHYT < STE | p < 0.0001; TEP < Turmipure | p < 0.0001; NOV > Turmipure | p < 0.0001; PHYT < Turmipure |
| Rel. bio. between 0 and 24 h [Log10] | / | p < 0.0001 | X | X | X | X | p < 0.0001; TEP < Turmipure | p < 0.0001; NOV > Turmipure | p < 0.0001; PHYT < Turmipure |
| Rel. bio. between 0 and 8 h [Log10] | / | p < 0.0001 | X | X | X | X | p < 0.0001; TEP < Turmipure | p = 0.0008; NOV > Turmipure | p < 0.0001; PHYT < Turmipure |
| Rel. bio. between 0 and infinity [Log10] | / | p < 0.0001 | X | X | X | X | p < 0.0001; TEP < Turmipure | p = 0.0009; NOV > Turmipure | p < 0.0001; PHYT < Turmipure |

TABLE 41-continued

Analysis of HHC sulfate (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Half-life (minutes) [Log10] | | p < 0.0001 | p = 0.0011; Turmipure < STE | | p = 0.0011; NOV < STE | | p = 0.0038; TEP > Turmipure | | |
| Terminal elimination rate constant [Log10] | | p < 0.0001 | p = 0.0011; Turmipure > STE | | p = 0.0011; NOV > STE | | p = 0.0038; TEP < Turmipure | | |
| Tmax (minutes) [Log10] | | p < 0.0001 | | | p < 0.0001; NOV < STE | p < 0.0001; PHYT > STE | | p = 0.0009; NOV < Turmipure | p < 0.0001; PHYT > Turmipure |

TABLE 42

Analysis of curcumin and all its relative metabolites (ng/mL) between products in the ITT population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | | p < 0.0001 | p = 0.0424; Turmipure > STE | | p < 0.0001; NOV > STE | p < 0.0001; PHYT < STE | p = 0.0005; TEP < Turmipure | | p < 0.0001; PHYT < Turmipure |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8 h (ng · h/mL) [Log10] | | p < 0.0001 | p = 0.0002; Turmipure > STE | | p < 0.0001; NOV > STE | p < 0.0001; PHYT < STE | p < 0.0001; TEP < Turmipure | p = 0.0073; NOV > Turmipure | p < 0.0001; PHYT < Turmipure |
| DN of AUC0-infinity (ng · h/mL/mg) [Log10] | p = 0.0328* | p < 0.0001 | p = 0.0003; Turmipure > STE | | p < 0.0001; NOV > STE | | p < 0.0001; TEP < Turmipure | | p = 0.0054; PHYT < Turmipure |
| AUC0-infinity (ng · h/mL) [Log10] | p = 0.0328* | p = 0.0128 | | | | p = 0.0475; PHYT < STE | | | |
| Normalized Cmax (ng/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| Cmax (ng/mL) [Log10] | | p < 0.0001 | p = 0.0009; Turmipure > STE | | p < 0.0001; NOV > STE | p < 0.0001; PHYT < STE | p < 0.0001; TEP < Turmipure | p < 0.0001; NOV > Turmipure | p < 0.0001; PHYT < Turmipure |
| Rel. bio. between 0 and 24 h [Log10] | | p < 0.0001 | X | X | X | X | p < 0.0001; TEP < Turmipure | p < 0.0001; NOV > Turmipure | p < 0.0001; PHYT < Turmipure |
| Rel. bio. between 0 and 8 h [Log10] | | p < 0.0001 | X | X | X | X | p < 0.0001; TEP < Turmipure | p < 0.0001; NOV > Turmipure | p < 0.0001; PHYT < Turmipure |
| Rel. bio. between 0 and infinity [Log10] | p = 0.0102* | p = 0.0002 | X | X | X | X | p = 0.0007; TEP < Turmipure | | p = 0.0050; PHYT < Turmipure |
| Half-life (minutes) [Log10] | | p < 0.0001 | p = 0.0036; Turmipure > STE | | p = 0.0015; NOV < STE | | p = 0.0111; TEP > Turmipure | | p = 0.0002; PHYT > Turmipure |
| Terminal elimination rate constant [Log10] | | p < 0.0001 | p = 0.0036; Turmipure > STE | | p = 0.0015; NOV > STE | | p = 0.0111; TEP < Turmipure | | p = 0.0002; PHYT < Turmipure |

TABLE 42-continued

Analysis of curcumin and all its relative metabolites (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Tmax (minutes) [Log10] | | p < 0.0001 | | | p < 0.0001; NOV < STE | p = 0.0297; PHYT > STE | | p < 0.0001; NOV < Turmipure | p = 0.0005; PHYT > Turmipure |

TABLE 43

Analysis of total parent compounds and their relative sulfate and glucuronide metabolites (ng/mL) between products in the ITT population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | | p < 0.0001 | | | | p < 0.0001; PHYT < STE | | p = 0.0057; NOV > Turmipure | p = 0.0005; PHYT < Turmipure |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8 h (ng · h/mL) [Log10] | | p < 0.0001 | | | p < 0.0001; NOV > STE | p < 0.0001; PHYT < STE | | p < 0.0001; NOV > Turmipure | p < 0.0001; PHYT < Turmipure |
| DN of AUC0-infinity (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p = 0.0142; NOV > Turmipure | p < 0.0001; PHYT < Turmipure |
| AUC0-infinity (ng · h/mL) [Log10] | | p = 0.0086 | | | | p = 0.0047; PHYT < STE | | | |
| Normalized Cmax (ng/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| Cmax (ng/mL) [Log10] | | p < 0.0001 | | | p < 0.0001; NOV > STE | p = 0.0022; PHYT < STE | | p < 0.0001; NOV > Turmipure | p = 0.0055; PHYT < Turmipure |
| Rel. bio. between 0 and 24 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and 8 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and infinity [Log10] | p = 0.0397* | p = 0.0151 | | | | | p = 0.0447; TEP < Turmipure | | |
| Half-life (minutes) [Log10] | | p = 0.0015 | p = 0.0122; Turmipure < STE | | p = 0.0032; NOV < STE | | | | |
| Terminal elimination rate constant [Log10] | | p = 0.0015 | p = 0.0122; Turmipure > STE | | p = 0.0032; NOV > STE | | | | |
| Tmax (minutes) [Log10] | | p < 0.0001 | | | p < 0.0001; NOV < STE | p = 0.0020; PHYT > STE | | p < 0.0001; NOV < Turmipure | p = 0.0099; PHYT > Turmipure |

TABLE 44

Analysis of total curcunninoids (ng/mL) between products in the PP population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | | p < 0.0001 | | | p < 0.0001; NOV > STE | p < 0.0001; PHYT < STE | p = 0.0014; TEP < Turmipure | | p < 0.0001; PHYT < Turmipure |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8 h (ng · h/mL) [Log10] | | p < 0.0001 | p = 0.0012; Turmipure > STE | | p < 0.0001; NOV > STE | p < 0.0001; PHYT < STE | p < 0.0001; TEP < Turmipure | p = 0.0048; NOV > Turmipure | p < 0.0001; PHYT < Turmipure |
| DN of AUC0-infinity (ng · h/mL/mg) [Log10] | p = 0.0222* | p < 0.0001 | p = 0.0003; Turmipure > STE | | p < 0.0001; NOV > STE | | p < 0.0001; TEP < Turmipure | | p = 0.0066; PHYT < Turmipure |
| AUC0-infinity (ng · h/mL) [Log10] | | p = 0.0007 | | | | p = 0.0032; PHYT < STE | | | p = 0.0014; PHYT < Turmipure |
| Normalized Cmax (ng/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| Cmax (ng/mL) [Log10] | | p < 0.0001 | p = 0.0009; Turmipure > STE | | p < 0.0001; NOV > STE | p < 0.0001; PHYT < STE | p < 0.0001; TEP < Turmipure | p < 0.0001; NOV > Turmipure | p < 0.0001; PHYT < Turmipure |
| Rel. bio. between 0 and 24 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and 8 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and infinity [Log10] | | p < 0.0001 | | | | | p < 0.0001; TEP < Turmipure | p < 0.0001; NOV > Turmipure | p < 0.0001; PHYT < Turmipure |
| Half-life (minutes) [Log10] | | p < 0.0001 | p = 0.0062; Turmipure < STE | | p = 0.0023; NOV < STE | | p = 0.0335; TEP > Turmipure | | p = 0.0010; PHYT > Turmipure |
| Terminal elimination rate constant [Log10] | | p < 0.0001 | p = 0.0138; Turmipure > STE | | p = 0.0034; NOV > STE | | p = 0.0058; TEP < Turmipure | | p = 0.0006; PHYT < Turmipure |
| Tmax (minutes) [Log10] | | p < 0.0001 | | | p < 0.0001; NOV < STE | p = 0.0282; PHYT > STE | | p < 0.0001; NOV < Turmipure | p = 0.0002; PHYT > Turmipure |

TABLE 45

Analysis of curcumin (ng/mL) between products in the PP population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p = 0.0002 | p = 0.0009; Turmipure > STE | | p = 0.0446; NOV > STE | | p = 0.0010; TEP < Turmipure | | |
| AUC0-24 h (ng · h/mL/mg) [Log10] | | | | | | | | | |

TABLE 45-continued

Analysis of curcumin (ng/mL) between products in the PP population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| DN of AUC0-8 h (ng · h/mL/mg) [Log10] | p = 0.0107* | | | | | | | | |
| AUC0-4 h (ng · h/mL/mg) [Log10] | | | | | | | | | |
| DN of AUC0-infinity (ng · h/mL/mg) [Log10] | p = 0.0209* | | | | | | | | |
| AUC0-infinity (ng · h/mL/mg) [Log10] | | | | | | | | | |
| Normalized Cmax (ng · h/mL/mg) [Log10] | p = 0.0128* | | | | | | | | |
| Cmax (ng/mL) [Log10] | | | | | | | | | |
| Rel. bio. between 0 and 24 h [Log10] | | | | | | | | | |
| Rel. bio between 0 and 8 h [Log10] | | p = 0.0138 | | | | | p = 0.0281; TEP < Turmipure | | |
| Rel. bio. between 0 and infinity [Log10] | | | | | | | | | |
| Half-life (minutes) [Log10] | | | | | | | | | |
| Terminal elimination rate constant [Log10] | | | | | | | | | |
| Tmax (minutes) [Log10] | | | | | | | | | |

TABLE 46

Analysis of curcumin glucuronide (ng/mL) between products in the PP population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | | p < 0.0001 | | | p < 0.0001; NOV > STE | p = 0.0002; PHYT < STE | | p < 0.0001; NOV > Turmipure | p = 0.0002; PHYT < Turmipure |
| DN of AUC0-8 h (ng · h/mL/mg) [Log10] | | p < 0.0001 | p < 0.0001; Turmipure > STE | | p < 0.0001; NOV > STE | p = 0.0120; PHYT > STE | p < 0.0001; TEP < Turmipure | p < 0.0001; NOV > Turmipure | p < 0.0001; PHYT < Turmipure |
| AUC0-8 h (ng · h/mL) [Log10] | | p < 0.0001 | | | p < 0.0001; NOV > STE | p < 0.0001; PHYT > STE | | p < 0.0001; NOV > Turmipure | p < 0.0001; PHYT < Turmipure |
| DN of | | p < 0.0001 | p < 0.0001; | | p < 0.0001; | p < 0.0001; | p < 0.0001; | p < 0.0001; | |

TABLE 46-continued

Analysis of curcumin glucuronide (ng/mL) between products in the PP population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| AUC0-infinity (ng · h/mL/mg) [Log10] | | | Turmipure > STE | | NOV > STE | PHYT > STE | TEP < Turmipure | NOV > Turmipure | |
| AUC0-infinity (ng · h/mL) [Log10] | | | | | | | | | |
| Normalized Cmax (ng/mL/mg) [Log10] | | p < 0.0001 | p < 0.0001; Turmipure > STE | | p < 0.0001; NOV > STE | | p < 0.0001; TEP < Turmipure | p < 0.0001; NOV > Turmipure | p = 0.0042; PHYT < Turmipure |
| Cmax (ng/mL) [Log10] | | p < 0.0001 | | | p < 0.0001; NOV > STE | p = 0.0401; PHYT < STE | | p < 0.0001; NOV > Turmipure | p = 0.0004; PHYT < Turmipure |
| Rel. bio. between 0 and 24 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and 8 h [Log10] | | p < 0.0001 | | | | | p < 0.0001; TEP < Turmipure | p < 0.0001; NOV > Turmipure | p < 0.0001; PHYT < Turmipure |
| Rel bio. between 0 and infinity [Log10] | | p < 0.0001 | | | | | p < 0.0001; TEP < Turmipure | p < 0.0001; NOV > Turmipure | |
| Half-life (minutes) [Log10] | | p < 0.0001 | p = 0.0157; Turmipure < STE | | p = 0.0002; NOV < STE | | | | p = 0.0132; PHYT > Turmipure |
| Terminal elimination rate constant [Log10] | | p < 0.0001 | p = 0.0015; Turmipure > STE | | p < 0.0001; NOV > STE | | | | p = 0.0123; PHYT < Turmipure |
| Tmax (minutes) [Log10] | | p < 0.0001 | | | p = 0.0047; NOV < STE | | | p = 0.0355; NOV < Turmipure | |

TABLE 47

Analysis of curcumin sulfate (ng/mL) between products in the PP population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| DN of AUC0-24 h (ng · h/mL/mg) [Log10] | p = 0.027* | p < 0.0001 | p < 0.0001; Turmipure > STE | | p < 0.0001; NOV > STE | p = 0.0001; PHYT > STE | p < 0.0001; TEP < Turmipure | p = 0.0068; NOV > Turmipure | p = 0.0003; PHYT < Turmipure |
| AUC0-24 h (ng · h/mL) [Log10] | p = 0.0024* | | | | | | | | |
| DN of AUC0-8 h (ng · h/mL/mg) [Log10] | p = 0.028* | p < 0.0001 | p < 0.0001; Turmipure > STE | | p < 0.0001; NOV > STE | p = 0.0385; PHYT > STE | p < 0.0001; TEP < Turmipure | p < 0.001; NOV > Turmipure | p < 0.0001; PHYT < Turmipure |
| AUC0-8 h (ng · h/mL) [Log10] | p = 0.0153* | p = 0.0001 | | | | | | | |
| DN of AUC0-infinity (ng · h/mL/mg) [Log10] | p = 0.0380* | p < 0.0001 | p < 0.0013; Turmipure > STE | | p = 0.0001; NOV > STE | | p = 0.0014; TEP < Turmipure | | |

TABLE 47-continued

Analysis of curcumin sulfate (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| AUC0-infinity (ng · h/mL) [Log10] | / | / | / | / | / | / | / | / | / |
| Normalized Cmax (ng/mL/mg) [Log10] | p = 0.0017* | p < 0.0001 | p = 0.0008; Turmipure > STE | / | p < 0.0001; NOV > STE | / | p = 0.0011; TEP < Turmipure | p < 0.0001; NOV > Turmipure | p = 0.0253; PHYT < Turmipure |
| Cmax (ng/mL) [Log10] | p = 0.0001* | p < 0.0001 | / | / | p = 0.0017; NOV > STE | / | / | p = 0.0022; NOV > Turmipure | / |
| Rel. bio. between 0 and 24 h [Log10] | / | p < 0.0001 | X | X | X | X | p < 0.0001; TEP < Turmipure | p < 0.0001; NOV > Turmipure | p < 0.0001; PHYT < Turmipure |
| Rel. bio. between 0 and 8 h [Log10] | / | p < 0.0001 | X | X | X | X | p < 0.0001; TEP < Turmipure | p < 0.0001; NOV > Turmipure | p < 0.0001; PHYT < Turmipure |
| Rel bio. between 0 and infinity [Log10] | p = 0.0094* | p < 0.0216 | X | X | X | X | / | / | / |
| Half-life (minutes) [Log10] | / | / | / | / | / | / | / | / | / |
| Terminal elimination rate constant [Log10] | / | p = 0.0122 | / | / | / | / | / | / | / |
| Tmax (minutes) [Log10] | / | p < 0.0001 | / | / | p < 0.0001; NOV > STE | / | p = 0.0097; TEP > Turmipure | p < 0.0001; NOV < Turmipure | p = 0.0033; PHYT > Turmipure |

TABLE 48

Analysis of curcumin and its relative sulfate and glucuronide matabolites (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | p = 0.0435* | p < 0.0001 | p < 0.0001; Turmipure > STE | / | p < 0.0001; NOV > STE | p < 0.0001; PHYT > STE | p < 0.0001; TEP < Turmipure | p = 0.008; NOV > Turmipure | p < 0.0001; PHYT < Turmipure |
| AUC0-24 h (ng · h/mL) [Log10] | p = 0.0388* | p = 0.0326 | / | / | / | / | / | / | / |
| DN of AUC0-8 h (ng · h/mL/mg) [Log10] | p = 0.0294* | p < 0.0001 | p < 0.0001; Turmipure > STE | / | p < 0.0001; NOV > STE | p = 0.026; PHYT > STE | p < 0.0001; TEP < Turmipure | p < 0.0001; NOV > Turmipure | p < 0.0001; PHYT < Turmipure |
| AUC0-8 h (ng · h/mL) [Log10] | / | p < 0.0001 | / | / | p < 0.0001; NOV > STE | p < 0.0001; PHYT > STE | / | p < 0.0001; NOV > Turmipure | p < 0.0001; PHYT < Turmipure |
| DN of AUC0-infinity (ng · h/mL/mg) [Log10] | p = 0.0025* | p < 0.0001 | p < 0.0001; Turmipure > STE | / | p < 0.0001; NOV > STE | p < 0.0338; PHYT > STE | p < 0.0001; TEP < Turmipure | p = 0.0493; NOV > Turmipure | p = 0.0126; PHYT < Turmipure |
| AUC0-infinity (ng · h/mL) [Log10] | p = 0.0013* | / | / | / | / | / | / | / | / |

TABLE 48-continued

Analysis of curcumin and its relative sulfate and glucuronide matabolites (ng/mL) between products in the PP population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | p = 0.0164* | p < 0.0001 | p = 0.018; Turmipure > STE | / | p < 0.0001; NOV > STE | / | p = 0.0015; TEP < Turmipure | p < 0.0001; NOV > Turmipure | / |
| Cmax (ng/mL) [Log10] | p = 0.0191* | p < 0.0001 | / | / | p < 0.0001; NOV > STE | / | / | p < 0.0001; NOV > Turmipure | / |
| Rel. bio. between 0 and 24 h [Log10] | / | p < 0.0001 | X | X | X | X | p 0.0001; TEP < Turmipure | p < 0.0001; NOV > Turmipure | p < 0.0001; PHYT < Turmipure |
| Rel. bio. between 0 and 8 h [Log10] | / | p < 0.0001 | X | X | X | X | p < 0.0001; TEP < Turmipure | p < 0.0001; NOV > Turmipure | p < 0.0001; PHYT < Turmipure |
| Rel bio. between 0 and infinity [Log10] | p = 0.0047* | p < 0.0035 | X | X | X | X | p = 0.0274; TEP < Turmipure | / | / |
| Half-life (minutes) [Log10] | / | p < 0.0012 | / | / | / | / | / | / | p =0.0067; PHYT < Turmipure |
| Terminal elimination rate constant [Log10] | / | p < 0.0001 | / | / | p = 0.0202; NOV > STE | / | / | / | p = 0.0027; PHYT < Turmipure |
| Tmax (minutes) [Log10] | / | p < 0.0001 | / | / | p < 0.0001; NOV < STE | / | / | p < 0.0001; NOV < Turmipure | / |

TABLE 49

Analysis of DMC glucuronide (ng/mL) between products in the PP population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | / |
| AUC0-24 h (ng · h/mL) [Log10] | / | p < 0.0001 | / | / | p = 0.0011; NOV > STE | / | / | p < 0.0001; NOV > Turmipure | / |
| DN of AUC0-8 h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p = 0.0138; PHYT < Turmipure |
| AUC0-8 h (ng · h/mL) [Log10] | / | p < 0.0001 | / | / | p < 0.0001; NOV > STE | / | / | p < 0.0001; NOV > Turmipure | / |
| DN of AUC0-infinity (ng · h/mL/mg) [Log10] | / | p < 0.0001 | p < 0.0001; Turmipure > STE | / | p < 0.0001; NOV > STE | p = 0.0143; PHYT > STE | p < 0.0001; TEP < Turmipure | p = 0.0107; NOV > Turmipure | / |
| AUC0-infinity (ng · h/mL) [Log10] | / | | / | / | / | / | / | / | / |
| Normalized Cmax | / | p < 0.0001 | p < 0.0001; Turmipure > | / | p < 0.0001; NOV > | p = 0.0068; PHYT > | p < 0.0001; TEP < | p < 0.0001; NOV > | p = 0.0312; PHYT < |

TABLE 49-continued

Analysis of DMC glucuronide (ng/mL) between products in the PP population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| (ng/mL/mg) [Log10] | | | STE | | STE | STE | Turmipure | Turmipure | Turmipure |
| Cmax (ng/mL) [Log10] | / | $p < 0.0001$ | / | / | $p < 0.0001$; NOV > STE | / | / | $p < 0.0001$; NOV > Turmipure | / |
| Rel. bio. between 0 and 24 h [Log10] | / | $p < 0.0001$ | X | X | X | X | $p < 0.0001$; TEP < Turmipure | $p < 0.0001$; NOV > Turmipure | / |
| Rel. bio. between 0 and 8 h [Log10] | / | $p < 0.0001$ | X | X | X | X | $p < 0.0001$; TEP < Turmipure | $p < 0.0001$; NOV > Turmipure | $p = 0.0216$; PHYT < Turmipure |
| Rel bio. between 0 and infinity [Log10] | / | $p < 0.0001$ | X | X | X | X | $p = 0.0003$; TEP < Turmipure | / | / |
| Half-life (minutes) [Log10] | / | $p = 0.0050$ | / | / | / | / | / | / | / |
| Terminal elimination rate constant [Log10] | / | $p = 0.0002$ | / | / | $p = 0.0006$; NOV > STE | / | / | $p = 0.0276$; NOV > Turmipure | / |
| Tmax (minutes) [Log10] | / | $p = 0.0086$ | / | / | / | / | / | / | / |

TABLE 50

Analysis of DMC sulfate (ng/mL) between products in the PP population.

| | | | Between-group analysis-Statistical significance of comparisons between products (adjusted p-value, Tukey adjustment) | | | | | | |
|---|---|---|---|---|---|---|---|---|---|
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | $p < 0.0001$ | $p < 0.0001$; Turmipure > STE | / | $p < 0.0001$; NOV > STE | $p < 0.0001$; PHYT > STE | $p < 0.0001$; TEP < Turmipure | / | $p < 0.0001$; PHYT < Turmipure |
| AUC0-24 h (ng · h/mL) [Log10] | / | $p = 0.0051$ | / | / | $p = 0.0068$; NOV < STE | / | / | / | / |
| DN of AUC0-8 h (ng · h/mL/mg) [Log10] | $p = 0.0310$* | $p < 0.0001$ | $p < 0.0001$; Turmipure > STE | / | $p < 0.0001$; NOV > STE | $p = 0.0092$; PHYT > STE | $p < 0.0001$; TEP < Turmipure | / | $p = 0.0231$; PHYT < Turmipure |
| AUC0-8 h (ng · h/mL) [Log10] | / | / | / | / | / | / | / | / | / |
| DN of AUC0-infinity (ng · h/mL/mg) [Log10] | / | $p < 0.0001$ | $p < 0.0001$; Turmipure > STE | / | $p < 0.0001$; NOV > STE | $p < 0.0001$; PHYT > STE | $p < 0.0001$; TEP < Turmipure | / | $p = 0.0021$; PHYT < Turmipure |
| AUC0-infinity (ng · h/mL) [Log10] | | $p = 0.0018$ | / | / | $p = 0.0021$; NOV < STE | / | / | / | / |

TABLE 50-continued

Analysis of DMC sulfate (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p = 0.0016; NOV > Turmipure | p = 0.082; PHYT < Turmipure |
| Cmax (ng/mL) [Log10] | | | | | | | | | |
| Rel. bio. between 0 and 24 h [Log10] | | p < 0.0001 | | | | | p < 0.0001; TEP < Turmipure | | p = 0.0015; PHYT < Turmipure |
| Rel. bio. between 0 and 8 h [Log10] | | p < 0.0001 | | | | | p < 0.0001; TEP < Turmipure | | p < 0.0001; PHYT < Turmipure |
| Rel bio. between 0 and infinity [Log10] | | p < 0.0001 | | | | | p < 0.0001; TEP < Turmipure | | |
| Half-life (minutes) [Log10] | | | | | | | | | |
| Terminal elimination rate constant [Log10] | | | | | | | | | |
| Tmax (minutes) [Log10] | | p < 0.0001 | | | p < 0.0001; NOV < STE | | | p = 0.0023; NOV < Turmipure | |

TABLE 51

Analysis of DMC and its relative sulfate and glucuronide metabolites (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p = 0.0035; NOV > Turmipure | p < 0.0001; PHYT < Turmipure |
| AUC0-24 h (ng · h/mL) [Log10] | | | | | | | | | |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8 h (ng · h/mL) [Log10] | | p < 0.0001 | | | p = 0.0078; NOV > STE | | | p = 0.0057; NOV > Turmipure | |
| DN of AUC0-infinity (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | | p < 0.0001; PHYT < Turmipure |
| AUC0-infinity (ng · h/mL) [Log10] | | p = 0.0138 | | | | | | | |

TABLE 51-continued

Analysis of DMC and its relative sulfate and glucuronide metabolites (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p = 0.0072; PHYT < Turmipure |
| Cmax (ng/mL) [Log10] | / | p < 0.0001 | / | / | p < 0.0001; NOV > STE | / | / | p < 0.0001; NOV > Turmipure | / |
| Rel. bio. between 0 and 24 h [Log10] | / | p < 0.0001 | X | X | X | X | p < 0.0001; TEP < Turmipure | p < 0.0001; NOV > Turmipure | p = 0.0191; PHYT < Turmipure |
| Rel. bio. between 0 and 8 h [Log10] | / | p < 0.0001 | X | X | X | X | p < 0.0001; TEP < Turmipure | p < 0.0001; NOV > Turmipure | p < 0.0001; PHYT < Turmipure |
| Rel bio. between 0 and infinity [Log10] | / | p < 0.0001 | X | X | X | X | p < 0.0001; TEP < Turmipure | / | p = 0.0047; PHYT < Turmipure |
| Half-life (minutes) [Log10] | / | p = 0.0004 | / | / | p = 0.0016; NOV < STE | / | / | p = 0.0018; NOV < Turmipure | / |
| Terminal elimination rate constant [Log10] | / | p = 0.0002 | / | / | p = 0.0040; NOV > STE | / | / | p = 0.0002; NOV > Turmipure | / |
| Tmax (minutes) [Log10] | / | p < 0.0001 | / | / | p < 0.0001; NOV < STE | p = 0.0073; PHYT > STE | p = 0.0150; TEP > Turmipure | p = 0.0030; NOV < Turmipure | p = 0.0032; PHYT > Turmipure |

TABLE 52

Analysis of BDMC glucuronide (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | p < 0.0001 | / | / | p < 0.0001; NOV > STE | / | / | p = 0.0001; NOV > Turmipure | / |
| AUC0-24 h (ng · h/mL) [Log10] | / | p = 0.0003 | p = 0.0003; Turmipure < STE | / | / | / | / | p = 0.0041; NOV > Turmipure | / |
| DN of AUC0-8 h (ng · h/mL/mg) [Log10] | / | p < 0.0001 | / | / | p < 0.0001; NOV > STE | / | / | p < 0.0001; NOV > Turmipure | / |
| AUC0-8 h (ng · h/mL) [Log10] | / | p < 0.0001 | p < 0.0001; Turmipure < STE | p = 0.0367; TEP < STE | / | p < 0.0001; PHYT < STE | p = 0.0156; TEP > Turmipure | p < 0.0001; NOV > Turmipure | / |
| DN of AUC0-infinity (ng · h/mL/mg) [Log10] | / | p < 0.0001 | / | / | p = 0.0006; NOV > STE | / | / | p = 0.0009; NOV > Turmipure | / |

TABLE 52-continued

Analysis of BDMC glucuronide (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| AUC0-infinity (ng · h/mL) [Log10] | / | p = 0.0003 | p = 0.0069; Turmipure < STE | / | / | p = 0.0475; PHYT < STE | p = 0.0202; TEP > Turmipure | p = 0.0422; NOV > Turmipure | / |
| Normalized Cmax (ng/mL/mg) [Log10] | / | p < 0.0001 | / | / | p < 0.0001; NOV > STE | / | p = 0.0009; TEP < Turmipure | p < 0.0001; NOV > Turmipure | / |
| Cmax (ng/mL) [Log10] | / | p < 0.0001 | p < 0.0001; Turmipure < STE | p = 0.0035; TEP < STE | / | p < 0.0001; PHYT < STE | / | p < 0.0001; NOV > Turmipure | / |
| Rel. bio. between 0 and 24 h [Log10] | / | p < 0.0001 | X | X | X | X | p = 0.0337; TEP < Turmipure | p = 0.005; NOV > Turmipure | / |
| Rel. bio. between 0 and 8 h [Log10] | / | p < 0.0001 | X | X | X | X | / | p < 0.0001; NOV > Turmipure | / |
| Rel bio. between 0 and infinity [Log10] | / | p = 0.0383 | X | X | X | X | / | | / |
| Half-life (minutes) [Log10] | / | p < 0.0001 | p = 0.0024; Turmipure < STE | / | / | p = 0.0003; PHYT < STE | p = 0.0117; TEP > Turmipure | p = 0.0072; NOV > Turmipure | / |
| Terminal elimination rate constant [Log10] | / | p < 0.0001 | p = 0.0050; Turmipure < STE | p = 0.0174; TEP < STE | / | p = 0.0003; PHYT < STE | / | p < 0.0001; NOV > Turmipure | / |
| Tmax (minutes) [Log10] | / | p = 0.0079 | / | / | / | / | / | p = 1.0176; NOV > Turmipure | / |

TABLE 53

Analysis of BDMC sulfate (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | p = 0.0012 | / | / | / | / | p = 0.0031; TEP < Turmipure | / | / |
| AUC0-24 h (ng · h/mL) [Log10] | / | p < 0.0001 | p < 0.0001; Turmipure < STE | / | p < 0.0001; NOV < STE | p < 0.0001; PHYT < STE | p < 0.0001; TEP > Turmipure | / | p = 0.0057; PHYT > Turmipure |
| DN of AUC0-8 h (ng · h/mL/mg) [Log10] | / | p < 0.0001 | / | / | p = 0.0191; NOV > STE | / | p < 0.0001; TEP < Turmipure | / | / |
| AUC0-8 h (ng · h/mL) [Log10] | / | p < 0.0001 | p < 0.0001; Turmipure < STE | / | p < 0.0001; NOV < STE | p < 0.0001; PHYT < STE | p < 0.0001; TEP > Turmipure | / | / |
| DN of AUC0-infinity (ng · h/mL/mg) [Log10] | / | / | / | / | / | / | / | / | / |

TABLE 53-continued

| Analysis of BDMC sulfate (ng/mL) between products in the PP population. | | | | | | | | | |
|---|---|---|---|---|---|---|---|---|---|
| | | | Between-group analysis-Statistical significance of comparisons between products (adjusted p-value, Tukey adjustment) | | | | | | |
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| AUC0-infinity (ng · h/mL) [Log10] | p = 0.0496* | p = 0.0165 | p = 0.0305; Turmipure < STE | / | / | / | / | / | / |
| Normalized Cmax (ng/mL/mg) [Log10] | p = 0.0213* | p = 0.0248 | / | / | / | / | / | / | / |
| Cmax (ng/mL) [Log10] | p = 0.0185* | p = 0.0029 | p = 0.0109; Turmipure < STE | / | p = 0.00392; NOV < STE | p = 0.0109; PHYT < STE | / | / | / |
| Rel. bio. between 0 and 24 h [Log10] | / | p = 0.0085 | X | X | X | X | / | / | / |
| Rel. bio. between 0 and 8 h [Log10] | / | p = 0.0003 | X | X | X | X | p = 0.033; TEP < Turmipure | / | / |
| Rel bio. between 0 and infinity [Log10] | / | / | X | X | X | X | / | / | / |
| Half-life (minutes) [Log10] | / | p < 0.0001 | p < 0.0001; Turmipure < STE | / | / | p = 0.0389; PHYT < STE | p < 0.0001; TEP > Turmipure | / | / |
| Terminal elimination rate constant [Log10] | / | p = 0.0013 | / | / | p = 0.0024; NOV > STE | / | / | / | / |
| Tmax (minutes) [Log10] | / | p = 0.0182 | / | / | / | / | p = 0.0474; TEP > Turmipure | / | p = 0.0147; PHYT > Turmipure |

TABLE 54

| Analysis of BDMC and its relative sulfate and glucuronide metabolites (ng/mL) between products in the PP population. | | | | | | | | | |
|---|---|---|---|---|---|---|---|---|---|
| | | | Between-group analysis-Statistical significance of comparisons between products (adjusted p-value, Tukey adjustment) | | | | | | |
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | p < 0.0001 | / | / | p = 0.0053; NOV > STE | / | p = 0.0002; TEP < Turmipure | / | / |
| AUC0-24 h (ng · h/mL) [Log10] | / | p < 0.0001 | p < 0.0001; Turmipure < STE | / | p < 0.0001; NOV < STE | p = 0.0002; PHYT < STE | p < 0.0001; TEP > Turmipure | / | p = 0.013; PHYT > Turmipure |
| DN of AUC0-8 h (ng · h/mL/mg) [Log10] | / | p < 0.0001 | p = 0.0189; Turmipure > STE | / | p < 0.0001; NOV < STE | / | p < 0.0001; TEP < Turmipure | p =0.0453; NOV > Turmipure | / |
| AUC0-8 h (ng · h/mL) [Log10] | / | p < 0.0001 | p < 0.0001; Turmipure < STE | / | p < 0.0001; NOV < STE | p < 0.0001; PHYT < STE | p < 0.0001; TEP < Turmipure | p = 0.0065; NOV > Turmipure | / |
| DN of AUC0-infinity (ng · h/mL/mg) [Log10] | / | p = 0.0041 | / | / | / | p = 0.0338; PHYT > STE | / | / | / |
| AUC0-infinity (ng · h/mL) [Log10] | / | | p < 0.0001; Turmipure < STE | / | p =0.0003; NOV < STE | / | p < 0.0001; TEP > Turmipure | / | p = 0.0157; PHYT > Turmipure |

TABLE 54-continued

Analysis of BDMC and its relative sulfate and glucuronide metabolites (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | / | p < 0.0001 | p < 0.0001; Turmipure > STE | p = 0.0212; TEP < STE | p < 0.0001; NOV > STE | / | p < 0.0001; TEP > Turmipure | p < 0.0001; NOV > Turmipure | p = 0.0005; PHYT < Turmipure |
| Cmax (ng/mL) [Log10] | / | p < 0.0001 | p < 0.0001; Turmipure < STE | p < 0.0001; TEP < STE | p < 0.0001; NOV > STE | p < 0.0001; PHYT < STE | p < 0.0001; TEP > Turmipure | p < 0.0001; NOV > Turmipure | / |
| Rel. bio. between 0 and 24 h [Log10] | / | p < 0.0001 | X | X | X | X | p =0.042; TEP < Turmipure | / | / |
| Rel. bio. between 0 and 8 h [Log10] | / | p < 0.0001 | X | X | X | X | p < 0.0001; TEP < Turmipure | / | / |
| Rel bio. between 0 and infinity [Log10] | / | / | X | X | X | X | / | / | / |
| Half-life (minutes) [Log10] | / | p < 0.0001 | p = 0.0025; Turmipure < STE | / | p = 0.0227; NOV < STE | / | p < 0.0001; TEP > Turmipure | / | p = 0.0309; PHYT > Turmipure |
| Terminal elimination rate constant [Log10] | / | p < 0.0001 | / | / | p < 0.0001; NOV > STE | / | / | p = 0.0007; NOV > Turmipure | / |
| Tmax (minutes) [Log10] | / | p < 0.0001; | / | / | / | p = 0.0299; PHYT > STE | / | / | p = 0.0048; PHYT > Turmipure |

TABLE 55

Analysis of THC glucuronide (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | p < 0.0001; | p < 0.0001; Turmipure > STE | | p < 0.0001; NOV > STE | / | p < 0.0001; TEP < Turmipure | p < 0.0001; NOV > Turmipure | p < 0.0001; PHYT < Turmipure |
| AUC0-24 h (ng · h/mL) [Log10] | / | p < 0.0001; | / | / | p = 0.0211; NOV > STE | p < 0.0001; PHYT < STE | p = 0.0215; TEP < Turmipure | / | p < 0.0001; PHYT < Turmipure |
| DN of AUC0-8 h (ng · h/mL/mg) [Log10] | / | p < 0.0001; | p < 0.0001; Turmipure > STE | / | p < 0.0001; NOV > STE | / | p < 0.0001; TEP < Turmipure | p < 0.0001; NOV > Turmipure | p < 0.0001; PHYT < Turmipure |
| AUC0-8 h (ng · h/mL) [Log10] | / | p < 0.0001; | / | / | p = 0.0009; NOV > STE | p < 0.0001; PHYT < STE | p = 0.0016; TEP < Turmipure | / | p < 0.0001; PHYT < Turmipure |
| DN of AUC0-infinity (ng · h/mL/mg) [Log10] | / | p < 0.0001; | p < 0.0001; Turmipure > STE | / | p < 0.0001; NOV > STE | p = 0.0387; PHYT < STE | p < 0.0001; TEP < Turmipure | / | p < 0.0001; PHYT < Turmipure |
| AUC0-infinity (ng · h/mL) [Log10] | / | | / | / | / | p < 0.0001; PHYT < STE | p = 0.0171; TEP < Turmipure | / | p < 0.0001; PHYT < Turmipure |

TABLE 55-continued

| Analysis of THC glucuronide (ng/mL) between products in the PP population. | | | | | | | | | |
|---|---|---|---|---|---|---|---|---|---|
| | | | Between-group analysis-Statistical significance of comparisons between products (adjusted p-value, Tukey adjustment) | | | | | | |
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | / | p < 0.0001; | p < 0.0001; Turmipure > STE | / | p < 0.0001; NOV > STE | p = 0.0182; PHYT > STE | p < 0.0001; TEP < Turmipure | p < 0.0001; NOV > Turmipure | p < 0.0001; PHYT < Turmipure |
| Cmax (ng/mL) [Log10] | / | p < 0.0001; | / | / | p < 0.0001; NOV > STE | p < 0.0001; PHYT > STE | p = 0.0288; TEP < Turmipure | / | p < 0.0001; PHYT < Turmipure |
| Rel. bio. between 0 and 24 h [Log10] | / | p < 0.0001; | X | X | X | X | p < 0.0001; TEP < Turmipure | p = 0.0029; NOV > Turmipure | p < 0.0001; PHYT < Turmipure |
| Rel. bio. between 0 and 8 h [Log10] | / | p < 0.0001; | X | X | X | X | p < 0.0001; TEP < Turmipure | p < 0.0001; NOV > Turmipure | p < 0.0001; PHYT < Turmipure |
| Rel bio. between 0 and infinity [Log10] | / | p < 0.0001; | X | X | X | X | p < 0.0001; TEP < Turmipure | / | p < 0.0001; PHYT < Turmipure |
| Half-life (minutes) [Log10] | / | p < 0.0001; | / | / | / | p < 0.0001; PHYT < STE | / | / | p < 0.0001; PHYT < Turmipure |
| Terminal elimination rate constant [Log10] | / | p = 0.0054 | / | / | / | / | / | / | / |
| Tmax (minutes) [Log10] | / | p < 0.0001; | / | / | / | p = 0.0003; PHYT < STE | / | / | p = 0.0003; PHYT < Turmipure |

TABLE 56

| Analysis of THC sulfate (ng/mL) between products in the PP population. | | | | | | | | | |
|---|---|---|---|---|---|---|---|---|---|
| | | | Between-group analysis-Statistical significance of comparisons between products (adjusted p-value, Tukey adjustment) | | | | | | |
| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | p = 0.0006* | / | / | / | / | / | / | / | / |
| AUC0-24 h (ng · h/mL) [Log10] | p = 0.0306* | / | / | / | / | / | / | / | / |
| DN of AUC0-8 h (ng · h/mL/mg) [Log10] | p = 0.0115* | / | / | / | / | / | / | / | / |
| AUC0-8 h (ng · h/mL) [Log10] | / | p < 0.0001 | / | / | | p 0.0064; PHYT < STE | / | / | p = 0.0003; PHYT < Turmipure |
| DN of AUC0-infinity (ng · h/mL/mg) [Log10] | / | p = 0.0009 | / | / | p =0.0196; NOV > STE | / | / | / | / |
| AUC0-infinity (ng · h/mL) [Log10] | / | p = 0.0105 | / | / | / | / | / | / | / |

TABLE 56-continued

Analysis of THC sulfate (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | $p = 0.0008$* | $p = 0.0439$ | | | | | | | |
| Cmax (ng/mL) [Log10] | | $p = 0.0005$ | | | | $p = 0.0284$;<br>PHYT < STE | | | $p = 0.0005$;<br>PHYT < Turmipure |
| Rel. bio. between 0 and 24 h [Log10] | | $p = 0.0022$ | | | | | | | |
| Rel. bio. between 0 and 8 h [Log10] | | $p < 0.0001$ | | | | | $p = 0.0041$;<br>TEP < Turmipure | | $p = 0.0121$;<br>PHYT < Turmipure |
| Rel bio. between 0 and infinity [Log10] | | | | | | | | | |
| Half-life (minutes) [Log10] | | $p = 0.0098$ | | | | | | | |
| Terminal elimination rate constant [Log10] | | $p = 0.0349$ | | | | | | | $p = 0.0151$;<br>PHYT < Turmipure |
| Tmax (minutes) [Log10] | $p = 0.0261$* | | | | | | | | |

TABLE 57

Analysis of HHC glucuronide (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | | $p < 0.0001$ | $p < 0.0001$;<br>Turmipure > STE | | $p < 0.0001$;<br>NOV > STE | $p < 0.0001$;<br>PHYT > STE | $p < 0.0001$;<br>TEP < Turmipure | $p < 0.0001$;<br>NOV > Turmipure | $p < 0.0001$;<br>PHYT < Turmipure |
| AUC0-24 h (ng · h/mL) [Log10] | | $p < 0.0001$ | $p = 0.0080$;<br>Turmipure > STE | | $p < 0.0001$;<br>NOV > STE | $p < 0.0001$;<br>PHYT < STE | $p < 0.0001$;<br>TEP < Turmipure | | $p < 0.0001$;<br>PHYT < Turmipure |
| DN of AUC0-8 h (ng · h/mL/mg) [Log10] | | $p < 0.0001$ | $p < 0.0001$;<br>Turmipure > STE | | $p < 0.0001$;<br>NOV > STE | | $p < 0.0001$;<br>TEP < Turmipure | $p < 0.0001$;<br>NOV > Turmipure | $p < 0.0001$;<br>PHYT < Turmipure |
| AUC0-8 h (ng · h/mL) [Log10] | | $p < 0.0001$ | $p = 0.0016$;<br>Turmipure > STE | | $p < 0.0001$;<br>NOV < STE | $p < 0.0001$;<br>PHYT < STE | $p < 0.0001$;<br>TEP < Turmipure | | $p < 0.0001$;<br>PHYT < Turmipure |
| DN of AUC0-infinity (ng · h/mL/mg) [Log10] | | $p < 0.0001$ | $p < 0.0001$;<br>Turmipure > STE | | $p < 0.0001$;<br>NOV > STE | | $p < 0.0001$;<br>TEP < Turmipure | $p = 0.0005$;<br>NOV > Turmipure | $p < 0.0001$;<br>PHYT < Turmipure |
| AUC0-infinity (ng · h/mL) [Log10] | | $p < 0.0001$ | | | $p = 0.0098$;<br>NOV > STE | $p < 0.0001$;<br>PHYT < STE | $p = 0.0032$;<br>TEP < Turmipure | | $p < 0.0001$;<br>PHYT < Turmipure |

TABLE 57-continued

Analysis of HHC glucuronide (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turnipure GOLD ™ vs STE | TEP vs STE | NOV vs STE | PHYT vs STE | TEP vs Turnipure GOLD ™ | NOV vs Turnipure GOLD ™ | PHYT vs Turnipure GOLD ™ |
| Normalized Cmax (ng/mL/mg) [Log10] | | p < 0.0001 | p < 0.0001; Turnipure > STE | | p < 0.0001; NOV > STE | | p < 0.0001; TEP < Turnipure | p < 0.0001; NOV > Turnipure | p < 0.0001; PHYT < Turnipure |
| Cmax (ng/mL) [Log10] | | p < 0.0001 | p = 0.0002; Turnipure > STE | | p < 0.0001; NOV > STE | p < 0.0001; PHYT < STE | p < 0.0001; TEP < Turnipure | p < 0.0001; NOV > Turnipure | p < 0.0001; PHYT < Turnipure |
| Rel. bio. between 0 and 24 h [Log10] | p = 0.0491* | p < 0.0001 | | | | | p < 0.0001; TEP < Turnipure | | p < 0.0001; PHYT < Turnipure |
| Rel. bio. between 0 and 8 h [Log10] | | p < 0.0001 | | | | | p < 0.0001; TEP < Turnipure | p < 0.0001; NOV > Turnipure | p < 0.0001; PHYT < Turnipure |
| Rel bio. between 0 and infinity [Log10] | | p < 0.0001 | | | | | p < 0.0001; TEP < Turnipure | p = 0.0337; NOV > Turnipure | p < 0.0001; PHYT < Turnipure |
| Half-life (minutes) [Log10] | | | | | | | | | |
| Terminal elimination rate constant [Log10] | | | | | | | | | |
| Tmax (minutes) [Log10] | | p < 0.0001 | | | p < 0.0001; NOV < STE | p = 0.0395; PHYT > STE | | p < 0.0001; NOV < Turnipure | p < 0.0001; PHYT < Turnipure |

TABLE 58

Analysis of HHC sulfate (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turnipure GOLD ™ vs STE | TEP vs STE | NOV vs STE | PHYT vs STE | TEP vs Turnipure GOLD ™ | NOV vs Turnipure GOLD ™ | PHYT vs Turnipure GOLD ™ |
| DN of AUC0-24 h (ng · h/mL/mg) [Log10] | | p < 0.0001 | p < 0.0001; Turnipure > STE | | p < 0.0001; NOV > STE | p < 0.0001; PHYT > STE | p < 0.0001; TEP < Turnipure | p < 0.0001; NOV > Turnipure | p < 0.0001; PHYT < Turnipure |
| AUC0-24 h (ng · h/mL) [Log10] | | p < 0.0001 | p = 0.0010; Turnipure > STE | | p < 0.0001; NOV > STE | p < 0.0001; PHYT < STE | p < 0.0001; TEP < Turnipure | | p < 0.0001; PHYT < Turnipure |
| DN of AUC0-8 h (ng · h/mL/mg) [Log10] | | p < 0.0001 | p < 0.0001; Turnipure > STE | | p < 0.0001; NOV > STE | p < 0.0001; PHYT > STE | p < 0.0001; TEP < Turnipure | p < 0.0001; NOV > Turnipure | p < 0.0001; PHYT < Turnipure |
| AUC0-8 h (ng · h/mL) [Log10] | | p < 0.0001 | p < 0.0001; Turnipure > STE | | p < 0.0001; NOV > STE | p < 0.0001; PHYT < STE | p < 0.0001; TEP < Turnipure | | p < 0.0001; PHYT < Turnipure |
| DN of AUC0-infinity (ng · h/mL/mg) [Log10] | | p < 0.0001 | p < 0.0001; Turnipure > STE | | p < 0.0001; NOV > STE | p < 0.0001; PHYT > STE | p < 0.0001; TEP < Turnipure | p < 0.0001; NOV > Turnipure | p < 0.0001; PHYT < Turnipure |

TABLE 58-continued

Analysis of HHC sulfate (ng/mL) between products in the PP population.

| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| | | | Between-group analysis-Statistical significance of comparisons between products (adjusted p-value, Tukey adjustment) | | | | | | |
| AUC0-infinity (ng · h/mL) [Log10] | | p < 0.0001 | | | p = 0.0322; NOV > STE | p < 0.0001; PHYT < STE | p = 0.0166; TEP < Turmipure | | p < 0.0001; PHYT < Turmipure |
| Normalized Cmax (ng/mL/mg) [Log10] | | p < 0.0001 | p < 0.0001; Turmipure > STE | | p < 0.0001; NOV > STE | p = 0.0252; PHYT > STE | p < 0.0001; TEP < Turmipure | p < 0.0001; NOV > Turmipure | p < 0.0001; PHYT < Turmipure |
| Cmax (ng/mL) [Log10] | | p < 0.0001 | p < 0.0001; Turmipure > STE | | p < 0.0001; NOV > STE | p < 0.0001; PHYT < STE | p < 0.0001; TEP < Turmipure | p < 0.0001; NOV > Turmipure | p < 0.0001; PHYT < Turmipure |
| Rel. bio. between 0 and 24 h [Log10] | | p < 0.0001 | | | | | p < 0.0001; TEP < Turmipure | p < 0.0001; NOV > Turmipure | p < 0.0001; PHYT < Turmipure |
| Rel. bio. between 0 and 8 h [Log10] | | p < 0.0001 | | | | | p < 0.0001; TEP < Turmipure | p < 0.0001; NOV > Turmipure | p < 0.0001; PHYT < Turmipure |
| Rel bio. between 0 and infinity [Log10] | | p < 0.0001 | | | | | p < 0.0001; TEP < Turmipure | p < 0.0001; NOV > Turmipure | p < 0.0001; PHYT < Turmipure |
| Half-life (minutes) [Log10] | | p < 0.0001 | p = 0.0011; Turmipure < STE | | p = 0.0012; NOV < STE | | p = 0.0075; TEP < Turmipure | | |
| Terminal elimination rate constant [Log10] | | p = 0.0012 | p = 0.0116; Turmipure > STE | | p = 0.0129; NOV > STE | | p = 0.0468; TEP < Turmipure | | |
| Tmax (minutes) [Log10] | | p < 0.0001 | | | p < 0.0001; NOV < STE | p < 0.0001; PHYT > STE | | p = 0.0009; NOV < Turmipure | p < 0.0001; PHYT < Turmipure |

TABLE 59

Analysis of curcumin and all its relative metabolites (ng/mL) between products in the PP population.

| Endpoint | Visit effect | Product effect | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| | | | Between-group analysis-Statistical significance of comparisons between products (adjusted p-value, Tukey adjustment) | | | | | | |
| DN of AUC0-24 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | | p < 0.0001 | p = 0.0435; Turmipure > STE | | p < 0.0001; NOV > STE | p < 0.0001; PHYT < STE | p = 0.0005; TEP < Turmipure | | p < 0.0001; PHYT < Turmipure |
| DN of AUC0-8 h (ng · h/mL/mg) [Log10] | | p < 0.0001 | p < 0.0001; Turmipure > STE | | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-8 h (ng · h/mL) [Log10] | | p < 0.0001 | p = 0.0007; Turmipure > STE | | p < 0.0001; NOV > STE | p < 0.0001; PHYT < STE | p < 0.0001; TEP < Turmipure | p = 0.0070; NOV > Turmipure | p < 0.0001; PHYT < Turmipure |
| DN of AUC0-infinity (ng · h/mL/mg) [Log10] | p = 0.0203* | p < 0.0001 | p = 0.0002; Turmipure > STE | | p < 0.0001; NOV > STE | | p = 0.0981; TEP < Turmipure | | p = 0.0034; PHYT < Turmipure |
| AUC0-infinity (ng · h/mL) [Log10] | | p < 0.0001 | | p = 0.0268; TEP | p = 0.0481; NOV > STE | p < 0.0001; PHYT < STE | p = 0.0011; TEP < Turmipure | | p < 0.0001; PHYT < Turmipure |

TABLE 59-continued

Analysis of curcumin and all its relative metabolites (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| Normalized Cmax (ng/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| Cmax (ng/mL) [Log10] | / | p < 0.0001 | p = 0.0009; Turmipure > STE | / | p < 0.0001; NOV > STE | p < 0.0001; PHYT < STE | p < 0.0001; TEP < Turmipure | p < 0.0001; NOV > Turmipure | p < 0.0001; PHYT < Turmipure |
| Rel. bio. between 0 and 24 h [Log10] | / | p < 0.0001 | X | X | X | X | p < 0.0001; TEP < Turmipure | p < 0.0001; NOV > Turmipure | p < 0.0001; PHYT < Turmipure |
| Rel. bio. between 0 and 8 h [Log10] | / | p < 0.0001 | X | X | X | X | p < 0.0001; TEP < Turmipure | p < 0.0001; NOV > Turmipure | p < 0.0001; PHYT < Turmipure |
| Rel bio. between 0 and infinity [Log10] | / | p < 0.0001 | X | X | X | X | p < 0.0001; TEP < Turmipure | p < 0.0001; NOV > Turmipure | p < 0.0001; PHYT < Turmipure |
| Half-life (minutes) [Log10] | / | p < 0.0001 | p = 0.0036; Turmipure < STE | / | p = 0.0015; NOV < STE | / | p = 0.0112; TEP > Turmipure | / | p = 0.0002; PHYT > Turmipure |
| Terminal elimination rate constant [Log10] | / | p < 0.0001 | p = 0.0037; Turmipure > STE | / | p = 0.0009; NOV > STE | / | p = 0.0014; TEP < Turmipure | / | p < 0.0001; PHYT < Turmipure |
| Tmax (minutes) [Log10] | / | p < 0.0001 | / | / | p < 0.0001; NOV < STE | p = 0.0298; PHYT > STE | / | p < 0.0001; NOV < Turmipure | p = 0.0005; PHYT > Turmipure |

TABLE 60

Analysis of total parent compounds and their relative sulfate and glucuronide metabolites (ng/mL) between products in the PP population.

| Endpoint | Visit effect | Product effect | Between-group analysis-Statistical significance of comparisons between products (adjusted p-value, Tukey adjustment) | | | | | | |
|---|---|---|---|---|---|---|---|---|---|
| | | | Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
| DN of AUC0-24 h (ng · h/mL/mg) [Log10] | / | p < 0.0001 | p < 0.0001; Turmipure > STE | / | p < 0.0001; NOV > STE | p < 0.0001; PHYT > STE | p < 0.0001; TEP < Turmipure | p < 0.0001; NOV > Turmipure | p < 0.0001; PHYT < Turmipure |
| AUC0-24 h (ng · h/mL) [Log10] | / | p < 0.0001 | / | / | / | p < 0.0001; PHYT < STE | / | p = 0.0002; NOV > Turmipure | p = 0.0003; PHYT < Turmipure |
| DN of AUC0-8 h (ng · h/mL/mg) [Log10] | p = 0.0310* | p < 0.0001 | p < 0.0001; Turmipure > STE | / | p < 0.0001; NOV > STE | p = 0.0002; PHYT > STE | p < 0.0001; TEP < Turmipure | p < 0.0001; NOV > Turmipure | p < 0.0001; PHYT < Turmipure |
| AUC0-8 h (ng · h/mL) [Log10] | / | p < 0.0001 | / | / | p < 0.0001; NOV > STE | p < 0.0001; PHYT < STE | / | p < 0.0001; NOV > Turmipure | p < 0.0001; PHYT < Turmipure |
| DN of AUC0-infinity (ng · h/mL/mg) [Log10] | / | p < 0.0001 | p < 0.0001; Turmipure > STE | / | p < 0.0001; NOV > STE | p = 0.0003; PHYT > STE | p < 0.0001; TEP < Turmipure | p < 0.0001; NOV > Turmipure | p < 0.0001; PHYT < Turmipure |
| AUC0-infinity (ng · h/mL) [Log10] | / | p = 0.0072 | / | / | / | p = 0.0042; PHYT < STE | / | / | / |
| Normalized Cmax | p = 0.0226* | p < 0.0001 | p = 0.0018; Turmipure > | / | p < 0.0001; NOV > | / | p = 0.0014; TEP < | p < 0.0001; NOV > | / |

TABLE 60-continued

Analysis of total parent compounds and their relative sulfate and glucuronide metabolites (ng/mL) between products in the PP population.

| Endpoint | Visit effect | Product effect | Between-group analysis-Statistical significance of comparisons between products (adjusted p-value, Tukey adjustment) Turmipure GOLD ™ vs STE | TEP vs STE | NOV vs STE | PHYT vs STE | TEP vs Turmipure GOLD ™ | NOV vs Turmipure GOLD ™ | PHYT vs Turmipure GOLD ™ |
|---|---|---|---|---|---|---|---|---|---|
| (ng/mL/mg) [Log10] | | | STE | | STE | | Turmipure | Turmipure | |
| Cmax (ng/mL) [Log10] | | p < 0.0001 | | | p < 0.0001; NOV > STE | p = 0.0020; PHYT < STE | | p < 0.0001; NOV > Turmipure | p 0.0056; PHYT < Turmipure |
| Rel. bio. between 0 and 24 h [Log10] | | p < 0.0001 | X | X | X | X | p < 0.0001; TEP < Turmipure | p < 0.0001; NOV > Turmipure | p < 0.0001; PHYT < Turmipure |
| Rel. bio. between 0 and 8 h [Log10] | | p < 0.0001 | X | X | X | X | p < 0.0001; TEP < Turmipure | p < 0.0001; NOV > Turmipure | p < 0.0001; PHYT < Turmipure |
| Rel bio. between 0 and infinity [Log10] | p = 0.0352* | p = 0.0213 | X | X | X | X | | | |
| Half-life (minutes) [Log10] | | p = 0.0019 | p = 0.0125; Turmipure < STE | | p = 0.0040; NOV < STE | | | | |
| Terminal elimination rate constant [Log10] | | p = 0.0003 | p = 0.0161; Turmipure > STE | | p = 0.0056; NOV > STE | | | | p = 0.0135; PHYT < Turmipure |
| Tmax (minutes) [Log10] | | p < 0.0001 | | | p < 0.0001; NOV < STE | p = 0.0008; PHYT > STE | | p < 0.0001; NOV < Turmipure | p = 0.0047; PHYT > Turmipure |

Serious Adverse Events:

Subject SN01-009: Cervical pain/road accident between V0 and V1 visits (under no study product) (locomotor/rheumatologic body system, event not related to a medical history, moderate intensity, no action on the study product, event not related to the research and the study product, event not associated with corrective treatments, recovery without sequelae).

Treatment emergent AEs with severe intensity:

Subject SN01-007: Lumbago between V2 and V3 visits (under Turmipure GOLD™ product) (locomotor/rheumatologic body system, event not related to a medical history, severe intensity, no action on the study product, event not related to the research and the study product, event not associated with corrective treatments, recovery without sequelae).

AEs related to the study products:

Subject SN01-008: Headache the day of V3 visit (under Turmipure GOLD™ product) (neurologic/psychiatric body system, event not related to a medical history, moderate intensity, no action on the study product, possible event related to the research and the study product, event associated with a corrective treatment (paracetamol), recovery without sequelae).

Subject SN01-030: Headache the day of V1 visit (under Turmipure GOLD™ product) (neurologic/psychiatric body system, event not related to a medical history, mild intensity, no action on the study product, possible event related to the research and the study product, event associated with a corrective treatment (paracetamol), recovery without sequelae).

Subject SN01-032: Headache the day of V2 visit (under NOV product) (neurologic/psychiatric body system, event not related to a medical history, mild intensity, no action on the study product, possible event related to the research and the study product, event not associated with corrective treatments, recovery without sequelae).

The results observed on PP population are similar to those on ITT population.

Mean±SD for Total curcuminoids (ITT population) is shown below.

TABLE 61

Mean ± SD for Total curcuminoids (ITT population)

| | STE product | TEP product | NOV product | PHYT product | Turmipure GOLD ™ product |
|---|---|---|---|---|---|
| Dose-normalized AUC(0-24 h) (ng · h/mL/mg) | 3.7 (1.75) | 3.2 (1.69) | 136.1 (37.40) | 13.0 (9.65) | 72.9 (25.49) |
| AUC(0-24 h) (ng · h/mL/mg) | 5075.6 (2407.80) | 4382.3 (2328.43) | 8538.8 (2345.94) | 2327.1 (1727.61) | 6519.7 (2280.33) |
| Dose-normalized AUC(0-8 h) (ng · h/mL/mg) | 1.6 (0.81) | 1.2 (0.52) | 81.8 (19.17) | 4.1 (3.83) | 38.1 (12.74) |
| AUC(0-8 h) (ng · h/mL/mg) | 2204.2 (1111.03) | 1725.7 (723.46) | 5132.6 (1202.41) | 737.6 (686.44) | 3410.0 (1139.65) |

TABLE 61-continued

| Mean ± SD for Total curcuminoids (ITT population) | | | | | |
|---|---|---|---|---|---|
| | STE product | TEP product | NOV product | PHYT product | Turmipure GOLD ™ product |
| Dose-normalized AUC (0-infinity) (ng · h/mL/mg) | 5.3 (5.80) | 3.2 (1.68) | 149.4 (64.93) | 14.6 (15.02) | 78.3 (37.82) |
| AUC(0-infinity) (ng · h/mL/mg) | 7273.2 (7969.82) | 4370.3 (2317.23) | 9369.3 (4072.30) | 2618.8 (2689.04) | 7001.1 (3382.63) |
| Normalized Cmax (ng/mL/mg) | 0.3 (0.14) | 0.3 (0.10) | 28.1 (7.23) | 1.2 (0.80) | 7.6 (3.06) |
| Cmax (ng/mL) | 444.7 (192.96) | 372.8 (141.70) | 1762.9 (453.72) | 209.1 (144.10) | 678.0 (273.35) |
| Relative bioavailability between 0 and 24 h | 1.0 (0.00) | 1.1 (0.79) | 49.7 (37.78) | 4.2 (4.15) | 24.2 (15.48) |
| Relative bioavailability between 0 and 8 h | 1.0 (0.00) | 1.1 (1.07) | 72.2 (58.68) | 2.9 (2.50) | 30.6 (20.00) |
| Relative bioavailability between 0 and infinity | 1.0 (0.00) | 1.0 (0.75) | 49.3 (37.74) | 3.7 (4.13) | 22.9 (15.28) |
| Half-life (minutes) | 788.4 (1233.91) | 505.2 (265.35) | 337.3 (278.83) | 640.1 (399.12) | 318.3 (154.44) |
| Terminal elimination rate constant | 0.1 (0.05) | 0.1 (0.04) | 0.2 (0.05) | 0.1 (0.05) | 0.2 (0.06) |
| Time to peak (minutes) | 256.5 (181.69) | 330.3 (341.21) | 61.0 (18.45) | 375.0 (249.39) | 189.5 (147.52) |

CONCLUSION

The results demonstrate that there are few differences between the bioavailability of the compounds found in TEP and STE (only 5 differences).

The composition within the scope of the present invention (Turmipure GOLD™) was found to provide better bioavailability of compounds than STE, TEP and PHYT, and was able to provide a similar bioavailability to NOV despite being administered at a lower dose (300 mg compared to 1000 mg) and using only natural ingredients with no synthetic carriers (such as polysorbate 80).

More specifically, Novasol was used at 1000 mg whereas the composition of the present invention (Turmipure GOLD™) was at 300 mg. As Turmipure yields an effect of 6520 (AUC in ng·h/mL) at 300 mg, if it were used at the same dosage as Novasol (1000 mg), it would yield an effect of 21733 (AUC in ng·h/mL), which is much higher than the effect of Novasol at the same dosage (8539).

The invention claimed is:

1. A composition comprising:

(i) at least about 20% curcuminoids by weight of the composition;

(ii) gum arabic in an amount from 40 to 60% by weight of the composition; and (iii) an extract obtained or obtainable from quillaja, wherein the composition comprises particles having an average diameter of from about 100 nm to about 10000 nm.

2. The composition according to claim 1, wherein the extract obtained or obtainable from quillaja is present in an amount from about 0.1 to about 5% by weight of the composition.

3. The composition according to claim 1, wherein the extract obtained or obtainable from quillaja comprises at least 50% saponins.

4. The composition according to claim 1, wherein the particles have an average diameter of from about 1000 nm to about 7000 nm.

5. The composition according to claim 4 further comprising plant and/or vegetable oil.

6. The composition according to claim 4, wherein the extract obtained or obtainable from quillaja is present in an amount from about 0.1 to about 5% by weight of the composition.

7. The composition according to claim 4, wherein the extract obtained or obtainable from quillaja comprises at least 50% saponins.

8. The composition according to claim 1 further comprising plant and/or vegetable oil.

9. The composition according to claim 8, wherein the extract obtained or obtainable from quillaja is present in an amount from about 0.1 to about 5% by weight of the composition.

10. A nutraceutical formulation, a dietary or food product for humans or animals, a nutritional supplement, a fragrance or flavouring, a pharmaceutical or veterinary formulation, an oenological or cosmetic formulation comprising the composition of claim 1.

11. The nutraceutical formulation, dietary or food product for humans or animals, nutritional supplement, fragrance or flavouring, pharmaceutical or veterinary formulation, oenological formulation or cosmetic formulation of claim 10, further comprising pharmaceutical ingredients, veterinary ingredients, food acceptable ingredients and mixtures thereof.

12. A nutraceutical formulation, a dietary or food product for humans or animals, a nutritional supplement, a fragrance or flavouring, a pharmaceutical or veterinary formulation, an oenological or cosmetic formulation consisting of the composition of claim 4.

13. A process for the preparation of a curcuminoid composition as defined in claim 1, wherein the process comprises the steps of:

(i) preparing an aqueous solution of curcuminoids;

(ii) mixing the aqueous solution from (i) with an aqueous gum arabic solution and extract obtained or obtainable from quillaja and optionally a plant and/or vegetable oil to provide an emulsion; and optionally (iii) drying the product of (ii) to provide a composition comprising particles having an average diameter of from about 100 nm to about 10000 nm.

14. The method according to claim 13, wherein the curcuminoids are selected from the group consisting of curcumin and its phase I or phase II metabolites, demethoxycurcumin and its phase I or phase II metabolites, bisdemethoxycurcumin and its phase I or phase II metabolites and mixtures thereof.

15. A method for improving bioaccessibility, bioavailability, bioefficacy and/or bioactivity of curcuminoids in mammals comprising the administration of said curcuminoids in the form of a composition according to claim 1.

16. The method according to claim 15 wherein the improvement in bioaccessibility, bioavailability, bioefficacy, and/or bioactivity of curcuminoids in mammals is due to improved gastrointestinal resistance of the curcuminoids and/or improved absorption of curcuminoids by intestinal cells and/or improved blood circulation.

* * * * *